United States Patent
Roy Chaudhuri et al.

(10) Patent No.: US 11,965,167 B2
(45) Date of Patent: Apr. 23, 2024

(54) MATERIALS AND METHODS FOR PROTEIN PRODUCTION

(71) Applicant: Impossible Foods Inc., Redwood City, CA (US)

(72) Inventors: Biswajoy Roy Chaudhuri, San Mateo, CA (US); Smita Shankar, Millbrae, CA (US)

(73) Assignee: Impossible Foods Inc., Redwood City, CA (US)

(*) Notice: Subject to any disclaimer, the term of this patent is extended or adjusted under 35 U.S.C. 154(b) by 313 days.

(21) Appl. No.: 16/858,443

(22) Filed: Apr. 24, 2020

(65) Prior Publication Data

US 2020/0340000 A1 Oct. 29, 2020

Related U.S. Application Data

(60) Provisional application No. 62/838,770, filed on Apr. 25, 2019.

(51) Int. Cl.
*C12N 15/00* (2006.01)
*C12N 15/52* (2006.01)

(52) U.S. Cl.
CPC ...... *C12N 15/52* (2013.01); *C12Y 203/01037* (2013.01)

(58) Field of Classification Search
CPC .............. C12N 2800/80; C12N 15/102; C12N 2310/3519; C12N 9/0061; C12N 15/8201; C12Y 203/01037; C12P 21/00
USPC .......................... 435/252.3, 320.1, 69.6, 69.7
See application file for complete search history.

(56) References Cited

U.S. PATENT DOCUMENTS

| | | | |
|---|---|---|---|
| 3,013,863 A | 12/1961 | May |
| 4,683,195 A | 7/1987 | Mullis |
| 4,683,202 A | 7/1987 | Mullis |
| 4,800,159 A | 1/1989 | Mullis |
| 4,886,753 A | 12/1989 | Marcker |
| 4,965,188 A | 10/1990 | Mullis |
| 5,204,253 A | 4/1993 | Sanford |
| 5,538,880 A | 7/1996 | Lundquist |
| 5,753,465 A | 5/1998 | Chien et al. |
| 5,824,511 A | 10/1998 | Mattoon et al. |
| 6,013,863 A | 1/2000 | Lundquist |
| 6,261,827 B1 | 7/2001 | Elrod |
| 6,329,571 B1 | 12/2001 | Hiei |
| 7,230,157 B1 | 6/2007 | Zuo |
| 8,021,695 B2 | 9/2011 | Gruber |
| 8,143,023 B2 | 3/2012 | Takagi et al. |
| 8,236,528 B2 | 8/2012 | Tsutsumi |
| 9,085,766 B2 | 7/2015 | Crane et al. |
| 9,938,326 B2 | 4/2018 | Akeda et al. |
| 9,938,327 B2 | 4/2018 | Shankar |
| 10,273,492 B2 | 4/2019 | Shankar |
| 10,689,656 B2 | 6/2020 | Shankar et al. |
| 2002/0194643 A1 | 12/2002 | Merot |
| 2004/0093643 A1 | 5/2004 | Ensley |
| 2006/0053515 A1 | 3/2006 | Geigenberger |
| 2007/0031832 A1 | 2/2007 | Watt |
| 2008/0085996 A1 | 4/2008 | Kuvshinov |
| 2008/0166757 A1 | 7/2008 | Bron |
| 2009/0328249 A1 | 12/2009 | Paget |
| 2010/0064384 A1 | 3/2010 | Zank |
| 2011/0129874 A1 | 6/2011 | Tsutsumi et al. |
| 2011/0287467 A1 | 11/2011 | Crane |
| 2012/0195883 A1 | 8/2012 | Huang |
| 2014/0325710 A1 | 10/2014 | Abad |
| 2015/0299716 A1 | 10/2015 | Zhou |
| 2016/0024512 A1 | 1/2016 | Armstrong |
| 2016/0130602 A1 | 5/2016 | Inzé |
| 2016/0340411 A1 | 11/2016 | Fraser |
| 2017/0188612 A1 | 7/2017 | Varadan |
| 2017/0342131 A1 | 11/2017 | Fraser |
| 2017/0342132 A1 | 11/2017 | Fraser |
| 2017/0349637 A1 | 12/2017 | Shankar |
| 2017/0349906 A1 | 12/2017 | Shankar |
| 2018/0127764 A1 | 5/2018 | Shankar |

(Continued)

FOREIGN PATENT DOCUMENTS

| | | |
|---|---|---|
| CN | 1974758 | 6/2007 |
| CN | 105483146 | 4/2016 |

(Continued)

OTHER PUBLICATIONS

DEvos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
[No Author Listed] Impossible Foods Inc. "GRAS Notification for Soybean Leghemoglobin Protein Derived from Pichia Pastoris." GRAS notice 000737, Retrieved from internet <URL:https://www.fda.gov/downloads/Food/IngredientsPackagingLabeling/GRAS/NoticeInventory/default.htm, 1063 pages, dated Oct. 2, 2017.
Abler and Scandalios, "Isolation and characterization of a genomic sequence encoding the maize Cat3 ctalase gene," Plant Mol. Biol., 1993, 22(6):1031-1038.

(Continued)

*Primary Examiner* — Robert B Mondesi
*Assistant Examiner* — Mohammad Y Meah
(74) *Attorney, Agent, or Firm* — Fish & Richardson P.C.

(57) ABSTRACT

This document relates to materials and methods for the production of protein. In one aspect, this document provides a first exogenous nucleic acid construct including a nucleotide sequence encoding an aminolevulinate synthase (ALAS) protein operably linked to a first promoter element, wherein the ALAS includes at least a first heme responsive motif (HRM), and wherein the ALAS includes a mutation in the first HRM, and a second exogenous nucleic acid construct comprising a nucleotide sequence encoding a heme-binding protein, wherein the second exogenous nucleic acid construct including a nucleotide sequence encoding the heme-binding protein is operably linked to the first promoter element or is operably linked to a second promoter element.

19 Claims, 32 Drawing Sheets

Specification includes a Sequence Listing.

(56) References Cited

U.S. PATENT DOCUMENTS

| | | |
|---|---|---|
| 2018/0371469 A1 | 12/2018 | Shankar |
| 2019/0292217 A1 | 9/2019 | Davis |
| 2019/0292555 A1 | 9/2019 | Davis |
| 2022/0290166 A1 | 9/2022 | Shankar et al. |

FOREIGN PATENT DOCUMENTS

| | | |
|---|---|---|
| CN | 108517327 | 9/2018 |
| EP | 2058398 | 5/2009 |
| EP | 2669375 | 12/2013 |
| JP | A-10-42873 | 2/1998 |
| JP | 2008017774 | 1/2008 |
| JP | A-2008-17733 | 1/2008 |
| JP | A-2009-505657 | 2/2009 |
| RU | 2520748 | 6/2014 |
| WO | WO 1998012913 | 4/1998 |
| WO | WO 2001098480 | 12/2001 |
| WO | WO 2003085113 | 10/2003 |
| WO | WO 2004057946 | 7/2004 |
| WO | WO 2004099405 | 11/2004 |
| WO | WO 2008090211 | 7/2008 |
| WO | WO 2009009142 | 1/2009 |
| WO | WO 2010063652 | 6/2010 |
| WO | WO 2012083424 | 6/2012 |
| WO | WO 2013010042 | 1/2013 |
| WO | WO 2014008729 | 1/2014 |
| WO | WO 2014110532 | 7/2014 |
| WO | WO 2014110539 | 7/2014 |
| WO | WO 2015153666 | 10/2015 |
| WO | WO 2016054375 | 4/2016 |
| WO | 2016183163 | 11/2016 |
| WO | WO 2018102656 | 6/2018 |
| WO | WO 2018102721 | 6/2018 |

OTHER PUBLICATIONS

Aoyama and Chua, "A glucocorticoid-mediated transcriptional induction system in transgenic plants," Plant J., 1997, 11(3):605-612.
Azmir, et al., "Techniques for extraction of bioactive compounds from plant materials," J. Food Engineering, 2013, 117(4):426-436.
Balaji, et al., "Expression of anti-tumor necrosis factor alpha (TNFα) single-chain variable fragment (scFv) in Spirodela punctata plants transformed with Agrobacterium tumefaciens," Biotechnology and Applied Biochemistry, 2016, 63(3):354-361.
Barata, et al., "Targeting of the soybean leghemoglobin to tobacco chloroplasts: effects on aerobic metabolism in transgenic plants," Plant Science, 2000, 155:193-202.
Benfey and Chua, "The cauliflower mosaic virus 35S promoter; combinatorial regulation of transcription in plants," Science, 1990, 250:959-966.
Benfey, et al., "The CaMV 35S enhancer contains at least two domains which can confer different developmental and tissue-specific expression patterns," The EMBO Journal, 1989, 8(8):2195-2202.
Böhner and Gatz, "Characterisation of novel target promoters for the dexamethasone-inducible/tetracycline-repressible regulator TGV using luciferase and isopentenyl transferase as sensitive reporter genes," Mol. Gen. Genet., 2001, 264:860-870.
Böhner, et al., "Transcriptional activator TGV mediates dexamethasone-inducible and tetracycline-inactivatabale gene expression," Plant J., 1999, 19:87-95.
Bruce, et al., "Expression profiling of the maize flavonoid pathway genes controlled by estradiol-inducible transcription factors CRC and P," Plant Cell, 2000, 12:65-79.
Caddick, et al., "An ethanol inducible gene switch for plants used to manipulate carbon metabolism," Nat. Biotechnol., 1998, 16:177-180.
Chaparro-Giraldo, et al., "Soybean leghemoglobin targeted to potato chloroplasts influences growth and development of transgenic plants," Plant Cell Reports, 2000, 19:961-965.

Chen, et al., "Regulated expression of genes encoding soybean B-conglycinins in transgenic plants," Dev. Genet., 1989, 10(2):112-122.
Chenna, et al., "Multiple sequence alignment with the Clustal series of programs" Nucleic Acids Res., 2003, 31(13):3497-3500.
Chiruvolu, et al., "Recombinant protein production in an alcohol oxidase-defective strain of Pichia pastoris in fedbatch fermentations," Enzyme Microb. Technol., 1997, 21:277-83.
Comai, et al., "Expression of a Brassic anapus malate synthase gene in transgenic tomato plants during the transition from late embryogeny to germination," Plant Physiol., 1992, 98:53-61.
Conceicao and Krebbers, "A cotyledon regulatory region is responsible for the different spatial expression patterns of Arabidopsis 2S albumin genes," Plant, 1994, 5:493-505.
Craft, et al., "New pOp/LhG4 vectors for stringent glucocorticoid-dependent transgene expression in Arabidopsis," Plant J., 2005, 41:899-918.
Cregg, et al., "Recombinant protein expression in Pichia pastoris," Molecular Biotechnology, 2000, 16:23-52.
Cuellar-Bermudez, et al., "Extraction and purification of high-value metabolites from microalgae: essential lipids, astaxanthin and phycobiliproteins," Microb. Biotechnol., 2015, 8(2):190-209.
Czarnecki and Grimm, "Post-translational control of tetrapyrrole biosynthesis in plants, algae, and cyanobacteria," J. Exp. Bot., 2012, 63(4):1675-1687.
Dailey et al., "Examination of mitochondrial protein targeting of haem synthetic enzymes: in vivo identification of three functional haem-responsive motifs in 5-aminolaevulinate synthase" Biochem J., 2005, 386(Pt 2):381-386.
Datta, et al., "Nucleotide sequence of a gene encoding soybean repetitive proline-rich protein 3," Plant Mol. Biol., 1990, 14(2):285-286.
Dayhoff et al., "A Model of Evolutionary Change in Proteins," Atlas of Protein Sequence and Structure, 1978, 5(Suppl. 3):345-352.
Ding, et al., "High-level expression of basic fibroblast growth factor in transgenic soybean seeds and characterization of its biological activity," Biotechnol. Lett., 2006, 28(12):869-875.
Eskelin, et al., "Production of a recombinant full-length collagen type I α-1 and of a 45-kDa collagen type I α-1 fragment in barley seeds," Plant Biotechnology Journal, 2009, 7:657-672.
Fraser et al., "Safety evaluation of soy leghemoglobin protein preparation derived from pichia pastoris, intended for use as a flavor catalyst in plant-based meat," International Journal of Toxicology, 2018, 37(3):241-262.
Gatz, et al., "Stringent repression and homogeneous de-repression by tetracycline of a modified CaMV 35S promoter in intact transgenic tobacco plants," Plant J., 1992, 2:397-404.
GenBank Accession No. AAA33980.1, "leghemoglobin [Glycine max]," Apr. 27, 1993, 1 page.
GenBank Accession No. AB365355.1, "Candida boidinii TRM1 gene for Zn(II)2Cys6-type transcription factor Trm1, complete cds," dated Mar. 22, 2008, 3 pages.
GenBank Accession No. AB548760.1, "Candida boidinii TRM2 gene for C2H2-type transcription factor Trm2, complete cds," dated Jul. 17, 2010, 3 pages.
GenBank Accession No. ABD57365.1, "methanol expression regulator I [Komagataella pastoris]," dated Mar. 4, 2006, 2 pages.
GenBank Accession No. AEOI02000005.1, bases 858873 to 862352, "Ogataea parapolymorpha DL-1 chr3, whole genome shotgun sequence," dated Dec. 3, 2013, 186 pages.
GenBank Accession No. AF066054.1, "Pichia pastoris formaldehyde dehydrogenase (FLD1) gene, complete cds," dated Sep. 17, 1998, 2 pages.
GenBank Accession No. AJ313360.1, "Hansenula polymorpha partial ORF1 DNA and MOX gene promoter region," dated Jul. 25, 2016, 2 pages.
GenBank Accession No. AJA60352.1, "ferrochelatase [Bradyrhizobium japonicum]," dated Feb. 24, 2015, 2 pages.
GenBank Accession No. AY288296.1, "Pichia pastoris 3-phosphoglycerate kinase (PGK1) gene, complete cds," dated Jul. 22, 2005, 2 pages.
GenBank Accession No. BAF99700.1, "Zn(II)2Cys6-type transcription factor Trm1 [Candida boidinii]," dated Mar. 22, 2008, 2 pages.

(56) References Cited

OTHER PUBLICATIONS

GenBank Accession No. BAJ07608.1, "C2H2-type transcription factor Trm2 [Candida boidinii]," dated Jul. 17, 2010, 1 page.
GenBank Accession No. CAY70887.1, "Hypothetical protein PAS_chr3_0836 [Komagataella phaffii GS115]," dated Feb. 27, 2015, 2 pages.
GenBank Accession No. DQ395124.1, "Pichia pastoris methanol expression regulator I gene, complete cds," dated Mar. 4, 2006, 2 pages.
GenBank Accession No. E06147.1, "Promoter of Candida alcohol oxidase gene," dated Nov. 4, 2005, 2 pages.
GenBank Accession No. ESX01253.1, "Regulatory protein ADR1 [Ogataea parapolymorpha DL-1]," dated Dec. 3, 2013, 2 pages.
GenBank Accession No. FJ752551.1, "Pichia pastoris dihydroxyacetone synthase 1 (DAS1) gene, complete cds" dated Mar. 21, 2009, 2 pages.
GenBank Accession No. J02798.1, "*Brassica napus* 1.7S napin seed storage protein (napA) gene, complete cds," dated Oct. 11, 2001, 2 pages.
GenBank Accession No. KJ755994.1, "Komagataella pastoris strain GS115 FLD1 gene, promoter region and 5' UTR," dated Jul. 30, 2014, 1 page.
GenBank Accession No. L05934.1, "*Zea mays* catalase (Cat3) gene, complete cds," dated Oct. 22, 1993, 3 pages.
GenBank Accession No. NM_173881.2, "Bos taurus myoglobin (MB), mRNA," dated Feb. 23, 2019, 2 pages.
GenBank Accession No. U62648.1, "Pichia pastoris glyceraldehyde-3-phosphate dehydrogenase (GAP) gene, complete cds," dated Mar. 7, 1997, 2 pages.
GenBank Accession No. U93215.3, "*Arabidopsis thaliana* chromosome 2 BAC T6B20 genomic sequence, complete sequence," dated Feb. 27, 2002, 32 pages.
GenBank Accession No. U96967.1, "Pichia pastoris strain NRRL Y-11430 alcohol oxidase (AOX1) gene, complete cds," dated Oct. 30, 2001, 2 pages.
GenBank Accession No. X02425.1, "Hansenula polymorpha MOX gene for methanol oxidase" dated Oct. 23, 2008, 3 pages.
GenBank Accession No. X79871.1, "P.pastoris AOX2 gene, promoter region," dated Jul. 26, 2016, 2 pages.
GenBank Accession No. XM_002490678.1, "Komagataella phaffii GS115 Hypothetical protein (PAS_chr1-4_0586), partial Mrna," dated Jul. 22, 2009, 2 pages.
GenBank Accession No. XP_014509945.1, "ferrochelatase-2, chloroplastic isoform X1 [*Vigna radiata* var. radiata]," dated Nov. 10, 2015, 1 page.
GenBank Accession No. YSAAODIA, "Candida boidinii methanol oxidase (AOD1) gene, complete cds," dated Apr. 27, 1993, 2 pages.
González-Domínguez et al., "Haem Regulation of the Mitochondrial Import of the Kluyveromyces Lactis 5-aminolaevulinate Synthase: An Organelle Approach," Yeast, 2001, 18(1):41-48.
Haddadi, "Investigation of crops cultivation systems: a review," Agricultural Advances, 2016, 5(3):269-274.
Hajdukiewicz, et al., "The small, versatile pPZP family of Agrobacterium binary vectors for plant transformation," Plant Mol. Biol., 1994, 25(6):989-994.
Harada, et al., "Spatially regulated genes expressed during seed germination and postgerminative development are activated during embryogeny," Mol. Gen. Genet., 1988, 212(3):466-473.
Hargrove, et al., "Characterization of recombinant soybean leghemoglobin a and apolar distal histidine mutants," J. Mol. Biol., 1997, 266:1032-1042.
Hoffman, et al., "Identification of rate-limiting steps in yeast heme biosynthesis," Biochem. Biophys. Res. Commun., 2003, 310(4):1247-1253.
Horvath, et al., "The production of recombinant proteins in transgenic barley grains," PNAS, 2000, 97:1914-1919.
Hyldig-Nielsen, et al., "The primary structures of two leghemoglobin genes from soybean," Nucleic Acids Res., 1982, 10:689-701.

Inan & Meagher, "Non-repressing carbon sources for alcohol oxidase (AOX1) promoter of Pichia pastoris," J. Biosci. Bioeng., 2001, 92:585-589.
Jokipii-Lukkari, et al., "Intrinsic non-symbiotic and truncated haemoglobins and heterologous Vitreoscilla haemoglobin expression in plants," Journal of Experimental Botany, 2009, 60(2):409-422.
Josefsson, et al., "Structure of a gene encoding the 1.7 S storage protein, napin, from *Brassica napus*," J. Biol. Chem., 1987, 262:12196-12201.
Kaltwasser, et al., "Construction and application of epitope- and green fluorescent protein-tagging integration vectors for Bacillus subtilis," Applied and Environmental Microbiology, 2002, 68:2624-2628.
Keddie, et al., "A seed-specific Brassica napus oleosin promoter interacts with a G-box-specific protein and may be bi-directional," Plant Mol. Biol., 1994, 24(2):327-340.
Keegstra and Cline, "Protein import and routing systems of chloroplasts," Plant Cell, 1999, 11:557- 579.
Koo, et al., "Ecdysone agonist-inducible expression of a coat protein gene from tobacco mosaic virus confers viral resistance in transgenic *Arabidopsis*," Plant J., 2004, 37:439-448.
Krainer, et al., "Optimizing cofactor availability for the production of recombinant heme peroxidase in Pichia pastoris," Microbial Cell Factories, 2015, 14(4):1-9.
Kranthi, et al., "Identification of Mxr1p-binding sites in the promoters of genes encoding dihydroxyacetone synthase and peroxin 8 of the methylotrophic yeast *Pichia pastoris*," Yeast, 2010, 27:705-711.
Kubota, et al., "Novel Mechanisms for Heme-dependent Degradation of ALAS1 Protein as a Component of Negative Feedback Regulation of Heme Biosynthesis," J. Biol. Chem., 2016, 291(39):20516-20529.
Liachko & Dunham, "An autonomously replicating sequence for use in a wide range of budding yeasts," FEMS Yeast Res., 2014, 14:364-367.
Lin-Cereghino, et al., "Mxr1p, a key regulator of the methanol utilization pathway and peroxisomal genes in Pichia pastoris," Mol. and Cell. Biol., 2006, 26:883-897.
Liu, et al., "Bacterial pathogen phytosensing in transgenic tobacco and *Arabidopsis* plants, " Plant Biotech. J., 2013, 11:43-52.
Liu, et al., "Balanced globin protein expression and heme biosynthesis improve production of human hemoglobin in *Saccharomyces cerevisiae*," Metabolic Engineering, 2014, 21:9-16.
Liu, et al., BMC Biotechnol., "Rapid in vivo analysis of synthetic promoters for plant pathogen phytosensing," 2011, 11:108, 9 pages.
Lloyd, et al., "Targeted mutagenesis using zinc-finger nucleases in *Arabidopsis*," Proc. Natl. Acad. Sci. USA, 2005, 102:2232-2237.
Londer, et al., "Production and preliminary characterization of a recombiant triheme cytochrom c7 from Geobatcher sulfurreducens in *Escherichia coli*," Biochem. Biophys. Acta 1, 2002, 1554(3):202-211.
Lutz, et al., "A guide to choosing vectors for transformation of the plastid genome of higher plants," Plant Physiol., 2007, 145:1201-1210.
Martinez, et al., "Ecdysone agonist inducible transcription in transgenic tobacco plants," Plant J., 1999, 19:97-106.
Marty, "Plant vacuoles," Plant Cell, 1999, 11:587-599.
Mense and Zhang, "Heme: a versatile signaling molecule controlling the activities of diverse regulators ranging from transcription factors to MAP kinases," Cell Res., 2006, 16:681-692.
Mett, et al., "Copper-controllable gene expression system for whole plants," PNAS, 1993, 90:4567-4571.
Miele, et al., "A GATA-type transcription factor regulates expression of the high-affinity iron uptake system in the methylotrophic yeast Pichia pastoris," Arch. Biochem. Biophys., 2007, 465:172-179.
Mitrophanov, et al., "Positive autoregulation shapes response timing and intensity in twocomponent signal transduction systems," J. Mol. Biol., 2010, 401(4):671-680.
Mitrophanov, et al.,"Positive feedback cellular control systems," Bioessays, 2008, 30(6):542-555.

(56) References Cited

OTHER PUBLICATIONS

Mochizuki, et al., "The cell biology of tetrapyrroles: a life and death struggle," Trends Plant Sci., 2010, 15(9):488-498.
Munakata et al., "Role of the Heme Regulatory Motif in the Heme-Mediated Inhibition of Mitochondrial Import of 5-aminolevulinate Synthase," J. Biochem., 2004, 136(2):233-238.
Naik, et al., "Production and utilisation of hydroponics fodder," Indian J. Anim. Nutr., 2015, 32(1):1-9.
Nakagawa, et al., "Alcohol oxidase hybrid oligomers formed in vivo and in vitro," Yeast, 1999, 15:1223-1230.
Padidam, et al., "Chemical-inducible, ecdysone receptor-based gene expression system for plants," Transgenic Res., 2003, 12:101-109.
PCT International Preliminary Report on Patentability in International Appln. No. PCT/US2014/055227, dated Mar. 15, 2016, pages.
PCT International Preliminary Report on Patentability in International Appln. No. PCT/US2016/031797, dated Nov. 14, 2017, 6 pages.
PCT International Preliminary Report on Patentability in International Appln. No. PCT/US2017/064160, dated Jun. 4, 2019, 8 pages.
PCT International Search Report and Written Opinion in International Appln. No. PCT/US2016/031797, dated Sep. 20, 2016, 9 pages.
PCT International Search Report and Written Opinion in International Appln. No. PCT/US2017/064160, dated Feb. 13, 2018, 11 pages.
PCT International Search Report and Written Opinion in International Appln. No. PCT/US2017/064274, dated Mar. 7, 2018, 9 pages.
Perez-Grau and Goldberg, "Soybean seed protein genes are regulated spatially during embryogenesis," Plant Cell., 1989, 1(11):1095-1109.
Phan, et al., "Novel plasmid-based expression vectors for intro- and extracellular production of recombinant proteins in Bacillus subtilis," Protein Expression & Purification, 2006, 46:189-195.
Proulx, et al., "Iron bioavailability of hemoglobin from soy root nodules using a caco-2 cell culture model," J. Agric. Food Chem., 2006, 54:1518-1522.
Qu, et al., "Ectopic expression of the cotton non-symbiotic hemoglobin gene GhHb1 triggers defense responses and increases disease tolerance in *Arabidopsis*," Plant Cell Physiol., 2006, 47:1058-1068.
Raymond, et al., "Development of the methylotrophic yeast *Pichia methanolica* for the expression of the 65 kilodalton isoform of human glutamate decarboxylase," Yeast, 1998, 14:11-23.
Reedy, et al., "Development of a heme-protein structure-electrochemical function database," Nucleic Acids Research, 2008, 36: Database issue D307-D313.
Reynolds and Smith, "The isocitrate lyase gene of cucumber: Isolation, characterisation and expression in cotyledons following seed germination," Plant Mol. Biol., 1995, 27:487-497.
Richards, et al., "Construction of a GFP-BAR plasmid and its use for switchgrass transformation," Plant Cell. Rep., 2001, 20:48-54.
Roslan, et al., "Characterization of the ethanol-inducible alc gene-expression system in *Arabidopsis thaliana*," Plant J., 2001, 28:225-235.
Salter, et al., "Characterisation of the ethanol-inducible alc gene expression system for transgenic plants, " Plant J., 1998, 16:127-132.
Samalova, et al., "pOp6/LhGR: a stringently regulated and highly responsive dexamethasone-inducible gene expression system for tobacco," Plant J., 2005, 41:919-935.
Sasano, et al., "Trm2p-dependent depression is essential for methanol-specific gene activation in the methylotrophic yeast *Candid boidinii*," FEMS Yeast Res., 2010, 10:535-544.
Search Report in Chinese Appln. No. 201480057829.3, dated Jan. 15, 2019, 2 pages, with English translation.
Shen, et al., "An optimized transit peptide for effective targeting of diverse foreign proteins into chloroplasts in rice," Scientific Reports, 2017, 7:46231, 12 pages.
Sheridan, et al., "The mac1 gene: controlling the commitment to the meiotic pathway in maize," Genetics, 1996, 142:1009-1020.
Sievers, et al., "The Primary Structure of Soybean (*Glycine max*) Leghemoglobin c*," Acta Chemica Scandinavico B, 1978, 32:380-386.
Sinagawa-Garcia, et al., "Next generation synthetic vectors for transformation of the plastid genome of higher plants," Plant Afol. Biol., 2009, 70:487-498.
Sjödahl, et al., "Deletion analysis of the Brassica napus cruciferin gene cru 1 promoter in transformed tobacco: promoter activity during early and late stages of embryogenesis is influenced by cis-acting elements in partially separate regions," Planta, 1995, 197:264-271.
Somleva, et al., "Agrobacterium-mediated genetic transformation of switchgrass," Crop Sci., 2002, 42:2080-2087.
Sossountzov, et al., "Spatial and temporal expression of a maize lipid transfer protein gene," Plant Cell, 1991, 3:923-933.
Sudhamsu et al., "Co-expression of ferrochelatase allows for complete heme incorporation into recombinant proteins produced in *E. coli*," Protein Expr. Purif., 2010, 73(1):78-82.
Supplementary European Search Report and Opinion in EP Appln. No. EP 14844701.4, dated Jan. 27, 2017, 6 pages.
Supplementary European Search Report and Opinion in EP Appln. No. EP 16793420.7, dated Aug. 29, 2018,8 pages.
Tanaka and Tanaka, "Tetrapyrrole biosynthesis in higher plants" Annu. Rev. Plant Biol., 2007, 58:321-46.
Thompson, et al., "Characterization of the herbicide-resistance gene bar from Streptomyces hygroscopicus," EMBO, 1987, 6:2519-2523.
Tjalsma, et al., "Signal peptide-dependent protein transport in Bacillus subtilis: a genome-based survey of the secretonne," Microbiol. and Molec. Biol. Rev., 2000, 64:515-547.
Tovkach, et al., "A toolbox and procedural notes for characterizing novel zinc finger nucleases for genome editing in plant cells," Plant J, 2009, 57:747-757 25.
Townsend, et al., "High-frequency modification of plant genes using engineered zinc-finger nucleases, " Nature, 2009, 459:442-445.
UniParc Accession No. UPI0001A4D18B, retrieved from URL <https://www.uniprot.org/uniparc/UPI0001A4D18B?sort=score>, available on or before Sep. 2018, 3 pages.
UniprotKB Accession No. P02236, "Leghemoglobin C2," dated Nov. 1, 1988, 9 pages.
Urao, et al., "Molecular cloning and characterization of a gene that encodes a MYC-related protein in *Arabidopsis*," Plant Mol. Biol, 1996, 32:571-576.
Van den Broeck, et al., "Targeting of a foreign protein to chloroplasts by fusion to the transit peptide from the small subunit of ribulose 1,5-bisphosphate carboxylase," Nature, 1985, 313:358-363.
Vellard, "The enzyme as drug: application of enzymes as pharmaceuticals," Current Opinion in Biotechnology, 2003, 14(4):444-450.
Vitale and Denecke, "The endoplasmic reticulum—gateway of the secretory pathway," Plant Cell, 1999, 11:615-628.
Vögeli-Lange, et al., "Evidence for a role of β-1,3-glucanase in dicot seed germination," Plant J., 1994, 5:273-278.
Vothknecht, et al., "Barley glutamyl tRNAGlu reductase: mutations affecting haem inhibition and enzyme activity," Phytochemistry, 1998, 47(4):513-519.
Washio and Ishikawa, "Organ-specific and hormone-dependent expression of genes for serine carboxypeptidases during developmetn and following germination of rice grains," Plant Physiol., 1994, 105:1275-1280.
Weinmann, et al., "A chimeric transactivator allows tetracycline-responsive gene expression in whole plants," Plant J., 1994, 5:559-569.
Werner, et al., "High-level recombinant protein expression in transgenic plants by using a double-inducible viral vector," PNAS, 2011, 108(34):14061-14066.
Wu, et al., "Efficient production of a functional single-chain antidigoxin antibody via an engineered Bacillus subtilis expression-secretion system," Nature Biotechnology, 1993, 11(1):71-76.
Xie and Yang, "RNA-guided genome editing in plants using a CRISPR-Cas system," Mal. Plant, 2013, 6:1975-1983.

(56) References Cited

OTHER PUBLICATIONS

Zhang, et al., "Isocitrate lyase and malate synthase genes from *Brassica napus* L. are active in pollen," Plant Physiol., 1994, 104:857-864.
Zhang, et al., "Optimization of the heme biosynthesis pathway for the production of 5-aminolevulinic acid in *Escherichia coli*," Sci. Rep., 2015, 5:8584, 7 pages.
Zhang, et al., "Transcription activator-like effector nucleases enable efficient plant genome engineering," Plant Physiol., 2013, 161:20-27.
Zuo, et al., "An estrogen receptor-based transactivator XVE mediates highly inducible gene expression in transgenic plants," Plant J., 2000, 24:265-273.
Kim et al., 'Increased expression of Fe-chelatase leads to increased metabolic flux into heme and confers protection against photodynamically induced oxidative stress,' Oct. 1, 2014, 271-287, 86(3), Plant molecular biology.
Malik et al., "Production of high levels of poly-3-hydroxybutyrate in plastids of Camelina sativa seeds," Jun. 2015, 675-688, 13(5), Plant biotechnology journal.
Pereira et al., "Conserved regulation of the Hansenula polymorpha MOX promoter in *Saccharomyces cerevisiae* reveals insights in the transcriptional activation by Adrip," European journal of biochemistry, May 1996, 181-191, 238 (1), Germany.
Sasano et al., "Trm1p, a Zn (II) 2Cys6-type transcription factor, is a master regulator of methanol-specific gene activation in the methylotrophic yeast *Candida boidinii*," Eukaryotic Cell, Mar. 2008, 527-536, 7(3), Japan.
Vogl et al., "Regulation of Pichia pastoris promoters and its consequences for protein production," New biotechnology, May 25, 2013, 385-404, 30(4), Austria.
Wang et al., "Mit1 transcription factor mediates methanol signaling and regulates the alcohol oxidase 1 (AOX1) promoter in Pichia pastoris," Journal of Biological Chemistry, Mar. 18, 2016, 6245-6261, 291(12), United States.
EP Extended European Search Report in European Appln. No. 20157598-2, dated Aug. 26, 2020, 18 pages.
U.S. Appl. No. 62/835,338, filed Apr. 17, 2019, Hoyt et al.
International Preliminary Report on Patentability in International Appln. No. PCT/US2020/029946, dated Nov. 4, 2021, 7 pages.
Yurimoto et al., "Methanol-inducible gene expression and heterologous protein production in the methylotrophic yeast *Candida boidinii*," Biotechnology and applied biochemistry, Jun. 2009, 85-92, 53(2), Great Britain.
Goodfellow et al., "The solution structure and heme binding of the presequence of murine 5-aminolevulinate synthase," FEBS Letters, 2001, 404(2):325-331.
International Search Report and Written Opinion in PCT Appln. No. PCT/US2020/029946, dated Jul. 14, 2020, 12 pages.
[No Author Listed] Impossible Foods Inc. "GRAS Notification for Soybean Leghemoglobin Protein Derived from Pichia Pastoris." GRAS notice 000540, Retrieved from internet <URL:https://www.fda.gov/Food/IngredientsPackagingLabeling/GRAS/NoticeInventory/default.htm.> dated Sep. 4, 2014, 109 pages, Redwood City, California.
Cramer et al., "Transgenic Plants for Therapeutic Proteins: Linking Upstream and Downstream Strategies," Curr Top Microbiol Immunol, 1999, 240:95-118.
Extended European Search Report in European Appln. No. 22151183.5, dated Jul. 13, 2022, 12 pages, Europe.
Ahmad et al., "Protein expression in Pichia pastoris: recent achievements and perspectives for heterologous protein production," Applied microbiology and biotechnology, Jun. 2014, 98:5301-5317.
Alberts et al., "Molecular Biology Of The Cell," 4th edition, 2002, 20 pages.
Bawa et al., "Functional recombinant protein is present in the pre-induction phases of Pichia pastoris cultures when grown in bioreactors, but not shake-flasks," Microbial cell factories, Dec. 2014, 13(1):1-13.

Benson et al., "GenBank," Nucleic Acids Research: Database Issue, 2014, 42:D32-D37.
De Schutter et al., "Genome sequence of the recombinant protein production host Pichia pastoris," Nature biotechnology, Jun. 2009, 27(6):561-5666.
Declaration of Dr. Carl Batt, dated Jan. 27, 2023, 137pages.
Declaration of Dr. Carl Batt, dated Jan. 27, 2023, 174 pages.
Declaration of Dr. Geoffrey Lin-Cereghino, dated Jan. 27, 2023, 51 pages.
Declaration of Dr. Sylvia Hall-Ellis, dated Jan. 27, 2023, 196 pages.
Engel et al., "Foods and food ingredients produced via recombinant DNA techniques: an overview," Genetically Modified Foods—Acs Symposium Series, 1995, Chapter 1:1-10.
Ferreira, "Heme synthesis," Encyclopedia Of Biological Chemistry, 2013 539-542.
Freeman, "Transcription and Translation," Biological Sciences, Chapter 16-18, 2d Edition, 2005, 338-400.
Garrocho-Villegas et al., "Plant hemoglobins: what we know six decades after their discovery," Gene, Aug. 15, 2007, 398(1-2):78-85.
GenBank Accession No. BAA24685.1, "leghemoglobin [Pisum sativum], " date Mar. 27, 2009, 3 pages.
GenBank Accession No. NF102272.2, "Protein Family Model PF00042 (heme-biding globins)," dated Jan. 27, 2021, 27 pages.
GenBank Accession No. XP_002492481.1: Ferrochelatase [Komagataella phaffii GS115], dated Oct. 11, 2017, 3 pages.
GenBank Accession No. XP_002493846.1 Delta-aminolevulinate dehydratase, a homooctameric enzyme [Komagataella phaffii GS115], dated Oct. 11, 2017.
Guarna et al., "On-line monitoring and control of methanol concentration in shake-flask cultures of Pichia pastoris," Biotechnology and bioengineering, Nov. 5, 1997, 56(3):279-286.
Haon et al., "Recombinant protein production facility for fungal biomass-degrading enzymes using the yeast *Pichia pastoris*," Frontiers in microbiology, Sep. 23, 2015, 6(1002): 12 pages.
Hartner et al., "Promoter library designed for fine-tuned gene expression in Pichia pastoris," Nucleic acids research, Jul. 1, 2008, 36(12): e76, 15 pages.
Hartner et al., "Regulation of methanol utilisation pathway genes in yeasts," Microbial cell factories, Dec. 2006, 5(39):1-21.
Hong et al., "Fermentation strategies for improved heterologous expression of laccase in Pichia pastoris," Biotechnology and Bioengineering, Aug. 20, 2002, 79(4):438-449.
Katakura et al., "Effect of methanol concentration on the production of human β2-glycoprotein I domain V by a recombinant Pichia pastoris: a simple system for the control of methanol concentration using a semiconductor gas sensor," Journal of Fermentation and Bioengineering, Jan. 1, 1998, 86(5):482-487.
Kelly et al., "Cultivation of methylotrophs," In Hydrocarbon and Lipid Microbiology Protocols: Isolation and Cultivation, Dec. 6, 2014, 33 pages.
Kranthi et al., "Identification of key DNA elements involved in promoter recognition by Mxr1p, a master regulator of methanol utilization pathway in Pichia pastoris," Biochimica et Biophysica Acta (BBA)—Gene Regulatory Mechanisms, Jun. 1, 2009, 1789(6-8):460-468.
Kurtz et al., "Development of autonomously replicating plasmids for Candida albicans," Molecular and Cellular Biology, Jan. 1987, 7(1):209-217.
Lin-Cereghino et al., "Heterologous protein expression in the methylotrophic yeast *Pichia pastoris*," FEMS microbiology reviews, Jan. 1, 2000, 24(1):45-66.
NCBI Resource Coordinators, "Database resources of the national center for biotechnology information," Nucleic acids research, Nov. 28, 2015, 44:D6-D19.
Nicola et al., "Structural rearrangements due to ligand binding and haem replacement in myoglobin and leghaemoglobins," European Journal of Biochemistry, Aug. 1977, 78(1):133-140.
Parua et al., "Pichia pastoris 14-3-3 regulates transcriptional activity of the methanol inducible transcription factor Mxr1 by direct interaction," Molecular microbiology, Jul. 2012, 85(2):282-298.

(56) References Cited

OTHER PUBLICATIONS

Rabert et al., "Recombinants proteins for industrial uses: utilization of Pichia pastoris expression system," Brazilian Journal of Microbiology, 2013, 44:351-356.

Roggenkamp et al., "Transformation of the methylotrophic yeast *Hansenula polymorpha* by autonomous replication and integration vectors," Molecular and General Genetics MGG, Feb. 1986, 202:302-308.

Sreekrishna, "Pichia, optimization of protein expression," Encyclopedia of industrial biotechnology: bioprocess, bioseparation, and cell technology, Flickinger MC. Hoboken, New Jersey: John Wiley and Sons, Inc., 2010:1-16.

Stryjewska et al., "Biotechnology and genetic engineering in the new drug development. Part I. DNA technology and recombinant proteins," Pharmacological reports, Sep. 2013, 65(5):1075-1085.

Trinh et al., "Effect of methanol feeding strategies on production and yield of recombinant mouse endostatin from Pichia pastoris," Biotechnology and Bioengineering, May 20, 2003, 82(4):438-444.

Vedvick et al., "High-level secretion of biologically active aprotinin from the yeast *Pichia pastoris*," Journal of industrial microbiology and biotechnology, Apr. 1, 1991, 7(3):197-201.

Zhang et al., "Heterologous protein expression in yeasts and filamentous fungi," Manual of Industrial Microbiology and Biotechnology, Mar. 25, 2010, 145-156.

GenBank Accession No. XM_002491600.1, "Komagataella phaffii GS115 5-aminolevulinate synthase, catalyzes the first step in the heme biosynthetic pathway (PAS_chr2-1_0716), partial mRNA," dated Oct. 11, 2017, 2 pages.

Office Action in Chinese Appln. No. 202080040385.8, dated Mar. 1, 2024, 17 pages (with machine translation).

* cited by examiner

Figure 4

<110> Impossible Foods Inc.

<210> 1
<211> 161
<212> PRT
<213> Vigna radiata

<400> 1
Met Thr Thr Thr Leu Glu Arg Gly Phe Thr Glu Glu Gln Glu Ala Leu
1               5                   10                  15
Val Val Lys Ser Trp Asn Val Met Lys Lys Asn Ser Gly Glu Leu Gly
            20                  25                  30
Leu Lys Phe Phe Leu Lys Ile Phe Glu Ile Ala Pro Ser Ala Gln Lys
        35                  40                  45
Leu Phe Ser Phe Leu Arg Asp Ser Thr Val Pro Leu Glu Gln Asn Pro
    50                  55                  60
Lys Leu Lys Pro His Ala Val Ser Val Phe Val Met Thr Cys Asp Ser
65                  70                  75                  80
Ala Val Gln Leu Arg Lys Ala Gly Lys Val Thr Val Arg Glu Ser Asn
                85                  90                  95
Leu Lys Lys Leu Gly Ala Thr His Phe Arg Thr Gly Val Ala Asn Glu
            100                 105                 110
His Phe Glu Val Thr Lys Phe Ala Leu Leu Glu Thr Ile Lys Glu Ala
        115                 120                 125
Val Pro Glu Met Trp Ser Pro Ala Met Lys Asn Ala Trp Gly Glu Ala
    130                 135                 140
Tyr Asp Gln Leu Val Asp Ala Ile Lys Tyr Glu Met Lys Pro Pro Ser
145                 150                 155                 160
Ser

<210> 2
<211> 133
<212> PRT
<213> Methylacidiphilum infernorum

<400> 2
Met Ile Asp Gln Lys Glu Lys Glu Leu Ile Lys Glu Ser Trp Lys Arg
1               5                   10                  15
Ile Glu Pro Asn Lys Asn Glu Ile Gly Leu Leu Phe Tyr Ala Asn Leu
            20                  25                  30
Phe Lys Glu Glu Pro Thr Val Ser Val Leu Phe Gln Asn Pro Ile Ser
        35                  40                  45
Ser Gln Ser Arg Lys Leu Met Gln Val Leu Gly Ile Leu Val Gln Gly

Figure 4 - Continued

```
             50                     55                     60
Ile Asp Asn Leu Glu Gly Leu Ile Pro Thr Leu Gln Asp Leu Gly Arg
 65                     70                     75                     80
Arg His Lys Gln Tyr Gly Val Val Asp Ser His Tyr Pro Leu Val Gly
                         85                     90                     95
Asp Cys Leu Leu Lys Ser Ile Gln Glu Tyr Leu Gly Gln Gly Phe Thr
                        100                    105                    110
Glu Glu Ala Lys Ala Ala Trp Thr Lys Val Tyr Gly Ile Ala Ala Gln
                        115                    120                    125
Val Met Thr Ala Glu
                        130
```

<210> 3
<211> 139
<212> PRT
<213> Aquifex aeolicus

```
<400> 3
Met Leu Ser Glu Glu Thr Ile Arg Val Ile Lys Ser Thr Val Pro Leu
  1                      5                     10                     15
Leu Lys Glu His Gly Thr Glu Ile Thr Ala Arg Met Tyr Glu Leu Leu
                         20                     25                     30
Phe Ser Lys Tyr Pro Lys Thr Lys Glu Leu Phe Ala Gly Ala Ser Glu
                         35                     40                     45
Glu Gln Pro Lys Lys Leu Ala Asn Ala Ile Ile Ala Tyr Ala Thr Tyr
                         50                     55                     60
Ile Asp Arg Leu Glu Glu Leu Asp Asn Ala Ile Ser Thr Ile Ala Arg
 65                     70                     75                     80
Ser His Val Arg Arg Asn Val Lys Pro Glu His Tyr Pro Leu Val Lys
                         85                     90                     95
Glu Cys Leu Leu Gln Ala Ile Glu Glu Val Leu Asn Pro Gly Glu Glu
                        100                    105                    110
Val Leu Lys Ala Trp Glu Glu Ala Tyr Asp Phe Leu Ala Lys Thr Leu
                        115                    120                    125
Ile Thr Leu Glu Lys Lys Leu Tyr Ser Gln Pro
                        130                    135
```

<210> 4
<211> 145
<212> PRT
<213> Glycine max

```
<400> 4
Met Gly Ala Phe Thr Glu Lys Gln Glu Ala Leu Val Ser Ser Ser Phe
  1                      5                     10                     15
```

Figure 4 - Continued

```
Glu Ala Phe Lys Ala Asn Ile Pro Gln Tyr Ser Val Val Phe Tyr Thr
             20                  25                  30
Ser Ile Leu Glu Lys Ala Pro Ala Ala Lys Asp Leu Phe Ser Phe Leu
         35                  40                  45
Ser Asn Gly Val Asp Pro Ser Asn Pro Lys Leu Thr Gly His Ala Glu
         50                  55                  60
Lys Leu Phe Gly Leu Val Arg Asp Ser Ala Gly Gln Leu Lys Ala Asn
 65                  70                  75                  80
Gly Thr Val Val Ala Asp Ala Ala Leu Gly Ser Ile His Ala Gln Lys
                 85                  90                  95
Ala Ile Thr Asp Pro Gln Phe Val Val Val Lys Glu Ala Leu Leu Lys
             100                 105                 110
Thr Ile Lys Glu Ala Val Gly Asp Lys Trp Ser Asp Glu Leu Ser Ser
             115                 120                 125
Ala Trp Glu Val Ala Tyr Asp Glu Leu Ala Ala Ala Ile Lys Lys Ala
         130                 135                 140
Phe
145

<210> 5
<211> 162
<212> PRT
<213> Hordeum vulgare

<400> 5
Met Ser Ala Ala Glu Gly Ala Val Val Phe Ser Glu Glu Lys Glu Ala
 1               5                  10                  15
Leu Val Leu Lys Ser Trp Ala Ile Met Lys Lys Asp Ser Ala Asn Leu
             20                  25                  30
Gly Leu Arg Phe Phe Leu Lys Ile Phe Glu Ile Ala Pro Ser Ala Arg
         35                  40                  45
Gln Met Phe Pro Phe Leu Arg Asp Ser Asp Val Pro Leu Glu Thr Asn
         50                  55                  60
Pro Lys Leu Lys Thr His Ala Val Ser Val Phe Val Met Thr Cys Glu
 65                  70                  75                  80
Ala Ala Ala Gln Leu Arg Lys Ala Gly Lys Ile Thr Val Arg Glu Thr
                 85                  90                  95
Thr Leu Lys Arg Leu Gly Gly Thr His Leu Lys Tyr Gly Val Ala Asp
             100                 105                 110
Gly His Phe Glu Val Thr Arg Phe Ala Leu Leu Glu Thr Ile Lys Glu
             115                 120                 125
Ala Leu Pro Ala Asp Met Trp Gly Pro Glu Met Arg Asn Ala Trp Gly
         130                 135                 140
Glu Ala Tyr Asp Gln Leu Val Ala Ala Ile Lys Gln Glu Met Lys Pro
145                 150                 155                 160
```

Figure 4 - Continued

Ala Glu

<210> 6
<211> 1153
<212> PRT
<213> Magnaporthe oryzae

<400> 6
```
Met Asp Gly Ala Val Arg Leu Asp Trp Thr Gly Leu Asp Leu Thr Gly
 1              5                   10                  15
His Glu Ile His Asp Gly Val Pro Ile Ala Ser Arg Val Gln Val Met
            20                  25                  30
Val Ser Phe Pro Leu Phe Lys Asp Gln His Ile Ile Met Ser Ser Lys
        35                  40                  45
Glu Ser Pro Ser Arg Lys Ser Ser Thr Ile Gly Gln Ser Thr Arg Asn
    50                  55                  60
Gly Ser Cys Gln Ala Asp Thr Gln Lys Gly Gln Leu Pro Pro Val Gly
65                  70                  75                  80
Glu Lys Pro Lys Pro Val Lys Glu Asn Pro Met Lys Lys Leu Lys Glu
                85                  90                  95
Met Ser Gln Arg Pro Leu Pro Thr Gln His Gly Asp Gly Thr Tyr Pro
            100                 105                 110
Thr Glu Lys Lys Leu Thr Gly Ile Gly Glu Asp Leu Lys His Ile Arg
        115                 120                 125
Gly Tyr Asp Val Lys Thr Leu Leu Ala Met Val Lys Ser Lys Leu Lys
    130                 135                 140
Gly Glu Lys Leu Lys Asp Asp Lys Thr Met Leu Met Glu Arg Val Met
145                 150                 155                 160
Gln Leu Val Ala Arg Leu Pro Thr Glu Ser Lys Lys Arg Ala Glu Leu
                165                 170                 175
Thr Asp Ser Leu Ile Asn Glu Leu Trp Glu Ser Leu Asp His Pro Pro
            180                 185                 190
Leu Asn Tyr Leu Gly Pro Glu His Ser Tyr Arg Thr Pro Asp Gly Ser
        195                 200                 205
Tyr Asn His Pro Phe Asn Pro Gln Leu Gly Ala Ala Gly Ser Arg Tyr
    210                 215                 220
Ala Arg Ser Val Ile Pro Thr Val Thr Pro Pro Gly Ala Leu Pro Asp
225                 230                 235                 240
Pro Gly Leu Ile Phe Asp Ser Ile Met Gly Arg Thr Pro Asn Ser Tyr
                245                 250                 255
Arg Lys His Pro Asn Asn Val Ser Ser Ile Leu Trp Tyr Trp Ala Thr
            260                 265                 270
Ile Ile Ile His Asp Ile Phe Trp Thr Asp Pro Arg Asp Ile Asn Thr
        275                 280                 285
```

Figure 4 - Continued

```
Asn Lys Ser Ser Ser Tyr Leu Asp Leu Ala Pro Leu Tyr Gly Asn Ser
    290                 295                 300
Gln Glu Met Gln Asp Ser Ile Arg Thr Phe Lys Asp Gly Arg Met Lys
305                 310                 315                 320
Pro Asp Cys Tyr Ala Asp Lys Arg Leu Ala Gly Met Pro Pro Gly Val
            325                 330                 335
Ser Val Leu Leu Ile Met Phe Asn Arg Phe His Asn His Val Ala Glu
        340                 345                 350
Asn Leu Ala Leu Ile Asn Glu Gly Gly Arg Phe Asn Lys Pro Ser Asp
            355                 360                 365
Leu Leu Glu Gly Glu Ala Arg Glu Ala Ala Trp Lys Lys Tyr Asp Asn
    370                 375                 380
Asp Leu Phe Gln Val Ala Arg Leu Val Thr Ser Gly Leu Tyr Ile Asn
385                 390                 395                 400
Ile Thr Leu Val Asp Tyr Val Arg Asn Ile Val Asn Leu Asn Arg Val
            405                 410                 415
Asp Thr Thr Trp Thr Leu Asp Pro Arg Gln Asp Ala Gly Ala His Val
            420                 425                 430
Gly Thr Ala Asp Gly Ala Glu Arg Gly Thr Gly Asn Ala Val Ser Ala
            435                 440                 445
Glu Phe Asn Leu Cys Tyr Arg Trp His Ser Cys Ile Ser Glu Lys Asp
    450                 455                 460
Ser Lys Phe Val Glu Ala Gln Phe Gln Asn Ile Phe Gly Lys Pro Ala
465                 470                 475                 480
Ser Glu Val Arg Pro Asp Glu Met Trp Lys Gly Phe Ala Lys Met Glu
            485                 490                 495
Gln Asn Thr Pro Ala Asp Pro Gly Gln Arg Thr Phe Gly Gly Phe Lys
            500                 505                 510
Arg Gly Pro Asp Gly Lys Phe Asp Asp Asp Leu Val Arg Cys Ile
            515                 520                 525
Ser Glu Ala Val Glu Asp Val Ala Gly Ala Phe Gly Ala Arg Asn Val
    530                 535                 540
Pro Gln Ala Met Lys Val Val Glu Thr Met Gly Ile Ile Gln Gly Arg
545                 550                 555                 560
Lys Trp Asn Val Ala Gly Leu Asn Glu Phe Arg Lys His Phe His Leu
            565                 570                 575
Lys Pro Tyr Ser Thr Phe Glu Asp Ile Asn Ser Asp Pro Gly Val Ala
            580                 585                 590
Glu Ala Leu Arg Arg Leu Tyr Asp His Pro Asp Asn Val Glu Leu Tyr
        595                 600                 605
Pro Gly Leu Val Ala Glu Glu Asp Lys Gln Pro Met Val Pro Gly Val
    610                 615                 620
Gly Ile Ala Pro Thr Tyr Thr Ile Ser Arg Val Val Leu Ser Asp Ala
625                 630                 635                 640
Val Cys Leu Val Arg Gly Asp Arg Phe Tyr Thr Thr Asp Phe Thr Pro
            645                 650                 655
```

Figure 4 - Continued

```
Arg Asn Leu Thr Asn Trp Gly Tyr Lys Glu Val Asp Tyr Leu Ser
            660             665             670
Val Asn His Gly Cys Val Phe Tyr Lys Leu Phe Ile Arg Ala Phe Pro
        675             680             685
Asn His Phe Lys Gln Asn Ser Val Tyr Ala His Tyr Pro Met Val Val
        690             695             700
Pro Ser Glu Asn Lys Arg Ile Leu Glu Ala Leu Gly Arg Ala Asp Leu
705             710             715             720
Phe Asp Phe Glu Ala Pro Lys Tyr Ile Pro Pro Arg Val Asn Ile Thr
                725             730             735
Ser Tyr Gly Gly Ala Glu Tyr Ile Leu Glu Thr Gln Glu Lys Tyr Lys
            740             745             750
Val Thr Trp His Glu Gly Leu Gly Phe Leu Met Gly Glu Gly Gly Leu
            755             760             765
Lys Phe Met Leu Ser Gly Asp Asp Pro Leu His Ala Gln Gln Arg Lys
    770             775             780
Cys Met Ala Ala Gln Leu Tyr Lys Asp Gly Trp Thr Glu Ala Val Lys
785             790             795             800
Ala Phe Tyr Ala Gly Met Met Glu Glu Leu Leu Val Ser Lys Ser Tyr
                805             810             815
Phe Leu Gly Asn Asn Lys His Arg His Val Asp Ile Ile Arg Asp Val
            820             825             830
Gly Asn Met Val His Val His Phe Ala Ser Gln Val Phe Gly Leu Pro
            835             840             845
Leu Lys Thr Ala Lys Asn Pro Thr Gly Val Phe Thr Glu Gln Glu Met
    850             855             860
Tyr Gly Ile Leu Ala Ala Ile Phe Thr Thr Ile Phe Phe Asp Leu Asp
865             870             875             880
Pro Ser Lys Ser Phe Pro Leu Arg Thr Lys Thr Arg Glu Val Cys Gln
                885             890             895
Lys Leu Ala Lys Leu Val Glu Ala Asn Val Lys Leu Ile Asn Lys Ile
            900             905             910
Pro Trp Ser Arg Gly Met Phe Val Gly Lys Pro Ala Lys Asp Glu Pro
            915             920             925
Leu Ser Ile Tyr Gly Lys Thr Met Ile Lys Gly Leu Lys Ala His Gly
        930             935             940
Leu Ser Asp Tyr Asp Ile Ala Trp Ser His Val Val Pro Thr Ser Gly
945             950             955             960
Ala Met Val Pro Asn Gln Ala Gln Val Phe Ala Gln Ala Val Asp Tyr
                965             970             975
Tyr Leu Ser Pro Ala Gly Met His Tyr Ile Pro Glu Ile His Met Val
            980             985             990
Ala Leu Gln Pro Ser Thr Pro Glu Thr Asp Ala Leu Leu Leu Gly Tyr
        995             1000            1005
Ala Met Glu Gly Ile Arg Leu Ala Gly Thr Phe Gly Ser Tyr Arg Glu
    1010            1015            1020
```

Figure 4 - Continued

```
Ala Ala Val Asp Asp Val Val Lys Glu Asp Asn Gly Arg Gln Val Pro
1025                1030                1035                1040
Val Lys Ala Gly Asp Arg Val Phe Val Ser Phe Val Asp Ala Ala Arg
                1045                1050                1055
Asp Pro Lys His Phe Pro Asp Pro Glu Val Val Asn Pro Arg Arg Pro
            1060                1065                1070
Ala Lys Lys Tyr Ile His Tyr Gly Val Gly Pro His Ala Cys Leu Gly
        1075                1080                1085
Arg Asp Ala Ser Gln Ile Ala Ile Thr Glu Met Phe Arg Cys Leu Phe
    1090                1095                1100
Arg Arg Arg Asn Val Arg Arg Val Pro Gly Pro Gln Gly Glu Leu Lys
1105                1110                1115                1120
Lys Val Pro Arg Pro Gly Gly Phe Tyr Val Tyr Met Arg Glu Asp Trp
                1125                1130                1135
Gly Gly Leu Phe Pro Phe Pro Val Thr Met Arg Val Met Trp Asp Asp
            1140                1145                1150
Glu
```

<210> 7
<211> 530
<212> PRT
<213> Fusarium oxysporum

<400> 7
```
Met Lys Gly Ser Ala Thr Leu Ala Phe Ala Leu Val Gln Phe Ser Ala
1               5                   10                  15
Ala Ser Gln Leu Val Trp Pro Ser Lys Trp Asp Glu Val Glu Asp Leu
            20                  25                  30
Leu Tyr Met Gln Gly Gly Phe Asn Lys Arg Gly Phe Ala Asp Ala Leu
        35                  40                  45
Arg Thr Cys Glu Phe Gly Ser Asn Val Pro Gly Thr Gln Asn Thr Ala
    50                  55                  60
Glu Trp Leu Arg Thr Ala Phe His Asp Ala Ile Thr His Asp Ala Lys
65                  70                  75                  80
Ala Gly Thr Gly Gly Leu Asp Ala Ser Ile Tyr Trp Glu Ser Ser Arg
            85                  90                  95
Pro Glu Asn Pro Gly Lys Ala Phe Asn Asn Thr Phe Gly Phe Phe Ser
            100                 105                 110
Gly Phe His Asn Pro Arg Ala Thr Ala Ser Asp Leu Thr Ala Leu Gly
        115                 120                 125
Thr Val Leu Ala Val Gly Ala Cys Asn Gly Pro Arg Ile Pro Phe Arg
    130                 135                 140
Ala Gly Arg Ile Asp Ala Tyr Lys Ala Gly Pro Ala Gly Val Pro Glu
145                 150                 155                 160
```

Figure 4 - Continued

```
Pro Ser Thr Asn Leu Lys Asp Thr Phe Ala Ala Phe Thr Lys Ala Gly
                165             170             175
Phe Thr Lys Glu Glu Met Thr Ala Met Val Ala Cys Gly His Ala Ile
            180             185             190
Gly Gly Val His Ser Val Asp Phe Pro Glu Ile Val Gly Ile Lys Ala
        195             200             205
Asp Pro Asn Asn Asp Thr Asn Val Pro Phe Gln Lys Asp Val Ser Ser
    210             215             220
Phe His Asn Gly Ile Val Thr Glu Tyr Leu Ala Gly Thr Ser Lys Asn
225             230             235             240
Pro Leu Val Ala Ser Lys Asn Ala Thr Phe His Ser Asp Lys Arg Ile
            245             250             255
Phe Asp Asn Asp Lys Ala Thr Met Lys Lys Leu Ser Thr Lys Ala Gly
            260             265             270
Phe Asn Ser Met Cys Ala Asp Ile Leu Thr Arg Met Ile Asp Thr Val
        275             280             285
Pro Lys Ser Val Gln Leu Thr Pro Val Leu Glu Ala Tyr Asp Val Arg
    290             295             300
Pro Tyr Ile Thr Glu Leu Ser Leu Asn Asn Lys Asn Lys Ile His Phe
305             310             315             320
Thr Gly Ser Val Arg Val Arg Ile Thr Asn Asn Ile Arg Asp Asn Asn
            325             330             335
Asp Leu Ala Ile Asn Leu Ile Tyr Val Gly Arg Asp Gly Lys Lys Val
            340             345             350
Thr Val Pro Thr Gln Gln Val Thr Phe Gln Gly Gly Thr Ser Phe Gly
            355             360             365
Ala Gly Glu Val Phe Ala Asn Phe Glu Phe Asp Thr Thr Met Asp Ala
        370             375             380
Lys Asn Gly Ile Thr Lys Phe Phe Ile Gln Glu Val Lys Pro Ser Thr
385             390             395             400
Lys Ala Thr Val Thr His Asp Asn Gln Lys Thr Gly Gly Tyr Lys Val
            405             410             415
Asp Asp Thr Val Leu Tyr Gln Leu Gln Gln Ser Cys Ala Val Leu Glu
            420             425             430
Lys Leu Pro Asn Ala Pro Leu Val Val Thr Ala Met Val Arg Asp Ala
            435             440             445
Arg Ala Lys Asp Ala Leu Thr Leu Arg Val Ala His Lys Lys Pro Val
    450             455             460
Lys Gly Ser Ile Val Pro Arg Phe Gln Thr Ala Ile Thr Asn Phe Lys
465             470             475             480
Ala Thr Gly Lys Lys Ser Ser Gly Tyr Thr Gly Phe Gln Ala Lys Thr
            485             490             495
Met Phe Glu Glu Gln Ser Thr Tyr Phe Asp Ile Val Leu Gly Gly Ser
            500             505             510
Pro Ala Ser Gly Val Gln Phe Leu Thr Ser Gln Ala Met Pro Ser Gln
            515             520             525
```

Figure 4 - Continued

```
Cys Ser
    530

<210> 8
<211> 358
<212> PRT
<213> Fusarium graminearum

<400> 8
Met Ala Ser Ala Thr Arg Gln Phe Ala Arg Ala Ala Thr Arg Ala Thr
 1               5                  10                  15
Arg Asn Gly Phe Ala Ile Ala Pro Arg Gln Val Ile Arg Gln Gln Gly
                20                  25                  30
Arg Arg Tyr Tyr Ser Ser Glu Pro Ala Gln Lys Ser Ser Ser Ala Trp
            35                  40                  45
Ile Trp Leu Thr Gly Ala Ala Val Ala Gly Gly Ala Gly Tyr Tyr Phe
        50                  55                  60
Tyr Gly Asn Ser Ala Ser Ser Ala Thr Ala Lys Val Phe Asn Pro Ser
65                  70                  75                  80
Lys Glu Asp Tyr Gln Lys Val Tyr Asn Glu Ile Ala Ala Arg Leu Glu
                85                  90                  95
Glu Lys Asp Asp Tyr Asp Asp Gly Ser Tyr Gly Pro Val Leu Val Arg
                100                 105                 110
Leu Ala Trp His Ala Ser Gly Thr Tyr Asp Lys Glu Thr Gly Thr Gly
                115                 120                 125
Gly Ser Asn Gly Ala Thr Met Arg Phe Ala Pro Glu Ser Asp His Gly
            130                 135                 140
Ala Asn Ala Gly Leu Ala Ala Arg Asp Phe Leu Gln Pro Val Lys
145                 150                 155                 160
Glu Lys Phe Pro Trp Ile Thr Tyr Ser Asp Leu Trp Ile Leu Ala Gly
                165                 170                 175
Val Cys Ala Ile Gln Glu Met Leu Gly Pro Ala Ile Pro Tyr Arg Pro
            180                 185                 190
Gly Arg Ser Asp Arg Asp Val Ser Gly Cys Thr Pro Asp Gly Arg Leu
        195                 200                 205
Pro Asp Ala Ser Lys Arg Gln Asp His Leu Arg Gly Ile Phe Gly Arg
    210                 215                 220
Met Gly Phe Asn Asp Gln Glu Ile Val Ala Leu Ser Gly Ala His Ala
225                 230                 235                 240
Leu Gly Arg Cys His Thr Asp Arg Ser Gly Tyr Ser Gly Pro Trp Thr
                245                 250                 255
Phe Ser Pro Thr Val Leu Thr Asn Asp Tyr Phe Arg Leu Leu Val Glu
                260                 265                 270
Glu Lys Trp Gln Trp Lys Lys Trp Asn Gly Pro Ala Gln Tyr Glu Asp
            275                 280                 285
```

Figure 4 - Continued

```
Lys Ser Thr Lys Ser Leu Met Met Leu Pro Ser Asp Ile Ala Leu Ile
    290                 295                 300
Glu Asp Lys Lys Phe Lys Pro Trp Val Glu Lys Tyr Ala Lys Asp Asn
305                 310                 315                 320
Asp Ala Phe Phe Lys Asp Phe Ser Asn Val Val Leu Arg Leu Phe Glu
                325                 330                 335
Leu Gly Val Pro Phe Ala Gln Gly Thr Glu Asn Gln Arg Trp Thr Phe
            340                 345                 350
Lys Pro Thr His Gln Glu
            355
```

<210> 9
<211> 122
<212> PRT
<213> Chlamydomonas eugametos

<400> 9
```
Met Ser Leu Phe Ala Lys Leu Gly Gly Arg Glu Ala Val Glu Ala Ala
1               5                   10                  15
Val Asp Lys Phe Tyr Asn Lys Ile Val Ala Asp Pro Thr Val Ser Thr
            20                  25                  30
Tyr Phe Ser Asn Thr Asp Met Lys Val Gln Arg Ser Lys Gln Phe Ala
        35                  40                  45
Phe Leu Ala Tyr Ala Leu Gly Gly Ala Ser Glu Trp Lys Gly Lys Asp
    50                  55                  60
Met Arg Thr Ala His Lys Asp Leu Val Pro His Leu Ser Asp Val His
65                  70                  75                  80
Phe Gln Ala Val Ala Arg His Leu Ser Asp Thr Leu Thr Glu Leu Gly
                85                  90                  95
Val Pro Pro Glu Asp Ile Thr Asp Ala Met Ala Val Val Ala Ser Thr
            100                 105                 110
Arg Thr Glu Val Leu Asn Met Pro Gln Gln
            115                 120
```

<210> 10
<211> 121
<212> PRT
<213> Tetrahymena pyriformis

<400> 10
```
Met Asn Lys Pro Gln Thr Ile Tyr Glu Lys Leu Gly Gly Glu Asn Ala
1               5                   10                  15
Met Lys Ala Ala Val Pro Leu Phe Tyr Lys Lys Val Leu Ala Asp Glu
            20                  25                  30
```

Figure 4 - Continued

```
Arg Val Lys His Phe Phe Lys Asn Thr Asp Met Asp His Gln Thr Lys
            35              40              45
Gln Gln Thr Asp Phe Leu Thr Met Leu Leu Gly Gly Pro Asn His Tyr
    50              55              60
Lys Gly Lys Asn Met Thr Glu Ala His Lys Gly Met Asn Leu Gln Asn
65              70              75              80
Leu His Phe Asp Ala Ile Ile Glu Asn Leu Ala Ala Thr Leu Lys Glu
                85              90              95
Leu Gly Val Thr Asp Ala Val Ile Asn Glu Ala Ala Lys Val Ile Glu
            100             105             110
His Thr Arg Lys Asp Met Leu Gly Lys
            115             120

<210> 11
<211> 117
<212> PRT
<213> Paramecium caudatum

<400> 11
Met Ser Leu Phe Glu Gln Leu Gly Gly Gln Ala Ala Val Gln Ala Val
1               5               10              15
Thr Ala Gln Phe Tyr Ala Asn Ile Gln Ala Asp Ala Thr Val Ala Thr
            20              25              30
Phe Phe Asn Gly Ile Asp Met Pro Asn Gln Thr Asn Lys Thr Ala Ala
            35              40              45
Phe Leu Cys Ala Ala Leu Gly Gly Pro Asn Ala Trp Thr Gly Arg Asn
    50              55              60
Leu Lys Glu Val His Ala Asn Met Gly Val Ser Asn Ala Gln Phe Thr
65              70              75              80
Thr Val Ile Gly His Leu Arg Ser Ala Leu Thr Gly Ala Gly Val Ala
                85              90              95
Ala Ala Leu Val Glu Gln Thr Val Ala Val Ala Glu Thr Val Arg Gly
            100             105             110
Asp Val Val Thr Val
            115

<210> 12
<211> 147
<212> PRT
<213> Aspergillus niger

<400> 12
Met Pro Leu Thr Pro Glu Gln Ile Lys Ile Ile Lys Ala Thr Val Pro
1               5               10              15
```

Figure 4 - Continued

```
Val Leu Gln Glu Tyr Gly Thr Lys Ile Thr Thr Ala Phe Tyr Met Asn
            20                  25                  30
Met Ser Thr Val His Pro Glu Leu Asn Ala Val Phe Asn Thr Ala Asn
        35                  40                  45
Gln Val Lys Gly His Gln Ala Arg Ala Leu Ala Gly Ala Leu Phe Ala
    50                  55                  60
Tyr Ala Ser His Ile Asp Asp Leu Gly Ala Leu Gly Pro Ala Val Glu
65                  70                  75                      80
Leu Ile Cys Asn Lys His Ala Ser Leu Tyr Ile Gln Ala Asp Glu Tyr
                85                  90                  95
Lys Ile Val Gly Lys Tyr Leu Leu Glu Ala Met Lys Glu Val Leu Gly
            100                 105                 110
Asp Ala Cys Thr Asp Asp Ile Leu Asp Ala Trp Gly Ala Ala Tyr Trp
            115                 120                 125
Ala Leu Ala Asp Ile Met Ile Asn Arg Glu Ala Ala Leu Tyr Lys Gln
            130                 135                 140
Ser Gln Gly
145
```

<210> 13
<211> 165
<212> PRT
<213> Zea mays

<400> 13
```
Met Ala Leu Ala Glu Ala Asp Asp Gly Ala Val Val Phe Gly Glu Glu
1               5                   10                  15
Gln Glu Ala Leu Val Leu Lys Ser Trp Ala Val Met Lys Lys Asp Ala
            20                  25                  30
Ala Asn Leu Gly Leu Arg Phe Phe Leu Lys Val Phe Glu Ile Ala Pro
            35                  40                  45
Ser Ala Glu Gln Met Phe Ser Phe Leu Arg Asp Ser Asp Val Pro Leu
    50                  55                  60
Glu Lys Asn Pro Lys Leu Lys Thr His Ala Met Ser Val Phe Val Met
65                  70                  75                      80
Thr Cys Glu Ala Ala Ala Gln Leu Arg Lys Ala Gly Lys Val Thr Val
                85                  90                  95
Arg Glu Thr Thr Leu Lys Arg Leu Gly Ala Thr His Leu Arg Tyr Gly
            100                 105                 110
Val Ala Asp Gly His Phe Glu Val Thr Gly Phe Ala Leu Leu Glu Thr
            115                 120                 125
Ile Lys Glu Ala Leu Pro Ala Asp Met Trp Ser Leu Glu Met Lys Lys
            130                 135                 140
Ala Trp Ala Glu Ala Tyr Ser Gln Leu Val Ala Ala Ile Lys Arg Glu
145                 150                 155                     160
```

Figure 4 - Continued

```
Met Lys Pro Asp Ala
            165

<210> 14
<211> 169
<212> PRT
<213> Oryza sativa subsp.   japonica

<400> 14
Met Ala Leu Val Glu Gly Asn Asn Gly Val Ser Gly Gly Ala Val Ser
 1               5                  10                  15
Phe Ser Glu Glu Gln Glu Ala Leu Val Leu Lys Ser Trp Ala Ile Met
            20                  25                  30
Lys Lys Asp Ser Ala Asn Ile Gly Leu Arg Phe Phe Leu Lys Ile Phe
            35                  40                  45
Glu Val Ala Pro Ser Ala Ser Gln Met Phe Ser Phe Leu Arg Asn Ser
            50                  55                  60
Asp Val Pro Leu Glu Lys Asn Pro Lys Leu Lys Thr His Ala Met Ser
65                  70                  75                  80
Val Phe Val Met Thr Cys Glu Ala Ala Gln Leu Arg Lys Ala Gly
                    85                  90                  95
Lys Val Thr Val Arg Asp Thr Thr Leu Lys Arg Leu Gly Ala Thr His
                    100                 105                 110
Phe Lys Tyr Gly Val Gly Asp Ala His Phe Glu Val Thr Arg Phe Ala
            115                 120                 125
Leu Leu Glu Thr Ile Lys Glu Ala Val Pro Val Asp Met Trp Ser Pro
            130                 135                 140
Ala Met Lys Ser Ala Trp Ser Glu Ala Tyr Asn Gln Leu Val Ala Ala
145                 150                 155                 160
Ile Lys Gln Glu Met Lys Pro Ala Glu
                    165

<210> 15
<211> 160
<212> PRT
<213> Arabidopsis thaliana

<400> 15
Met Glu Ser Glu Gly Lys Ile Val Phe Thr Glu Glu Gln Glu Ala Leu
 1               5                  10                  15
Val Val Lys Ser Trp Ser Val Met Lys Lys Asn Ser Ala Glu Leu Gly
            20                  25                  30
Leu Lys Leu Phe Ile Lys Ile Phe Glu Ile Ala Pro Thr Thr Lys Lys
            35                  40                  45
```

Figure 4 - Continued

```
Met Phe Ser Phe Leu Arg Asp Ser Pro Ile Pro Ala Glu Gln Asn Pro
     50                      55                  60
Lys Leu Lys Pro His Ala Met Ser Val Phe Val Met Cys Cys Glu Ser
 65              70                  75                      80
Ala Val Gln Leu Arg Lys Thr Gly Lys Val Thr Val Arg Glu Thr Thr
                 85                  90                  95
Leu Lys Arg Leu Gly Ala Ser His Ser Lys Tyr Gly Val Val Asp Glu
                100             105                 110
His Phe Glu Val Ala Lys Tyr Ala Leu Leu Glu Thr Ile Lys Glu Ala
             115                 120                 125
Val Pro Glu Met Trp Ser Pro Glu Met Lys Val Ala Trp Gly Gln Ala
     130                 135                 140
Tyr Asp His Leu Val Ala Ala Ile Lys Ala Glu Met Asn Leu Ser Asn
145                  150                 155                 160
```

<210> 16
<211> 147
<212> PRT
<213> Pisum sativum

<400> 16
```
Met Gly Phe Thr Asp Lys Gln Glu Ala Leu Val Asn Ser Ser Trp Glu
 1               5                  10                  15
Ser Phe Lys Gln Asn Leu Ser Gly Asn Ser Ile Leu Phe Tyr Thr Ile
             20                  25                  30
Ile Leu Glu Lys Ala Pro Ala Ala Lys Gly Leu Phe Ser Phe Leu Lys
             35                  40                  45
Asp Thr Ala Gly Val Glu Asp Ser Pro Lys Leu Gln Ala His Ala Glu
     50                  55                  60
Gln Val Phe Gly Leu Val Arg Asp Ser Ala Ala Gln Leu Arg Thr Lys
 65                  70                  75                  80
Gly Glu Val Val Leu Gly Asn Ala Thr Leu Gly Ala Ile His Val Gln
                 85                  90                  95
Arg Gly Val Thr Asp Pro His Phe Val Val Val Lys Glu Ala Leu Leu
                100                 105                 110
Gln Thr Ile Lys Lys Ala Ser Gly Asn Asn Trp Ser Glu Glu Leu Asn
             115                 120                 125
Thr Ala Trp Glu Val Ala Tyr Asp Gly Leu Ala Thr Ala Ile Lys Lys
     130                 135                 140
Ala Met Thr
145
```

Figure 4 - Continued

```
<210> 17
<211> 145
<212> PRT
<213> Vigna unguiculata

<400> 17
Met Val Ala Phe Ser Asp Lys Gln Glu Ala Leu Val Asn Gly Ala Tyr
 1               5                  10                  15
Glu Ala Phe Lys Ala Asn Ile Pro Lys Tyr Ser Val Val Phe Tyr Thr
                20                  25                  30
Thr Ile Leu Glu Lys Ala Pro Ala Ala Lys Asn Leu Phe Ser Phe Leu
            35                  40                  45
Ala Asn Gly Val Asp Ala Thr Asn Pro Lys Leu Thr Gly His Ala Glu
        50                  55                  60
Lys Leu Phe Gly Leu Val Arg Asp Ser Ala Ala Gln Leu Arg Ala Ser
65                  70                  75                  80
Gly Gly Val Val Ala Asp Ala Leu Gly Ala Val His Ser Gln Lys
                85                  90                  95
Ala Val Asn Asp Ala Gln Phe Val Val Val Lys Glu Ala Leu Val Lys
                100                 105                 110
Thr Leu Lys Glu Ala Val Gly Asp Lys Trp Ser Asp Glu Leu Gly Thr
            115                 120                 125
Ala Val Glu Leu Ala Tyr Asp Glu Leu Ala Ala Ile Lys Lys Ala
        130                 135                 140
Tyr
145

<210> 18
<211> 154
<212> PRT
<213> Bos taurus

<400> 18
Met Gly Leu Ser Asp Gly Glu Trp Gln Leu Val Leu Asn Ala Trp Gly
 1               5                  10                  15
Lys Val Glu Ala Asp Val Ala Gly His Gly Gln Glu Val Leu Ile Arg
                20                  25                  30
Leu Phe Thr Gly His Pro Glu Thr Leu Glu Lys Phe Asp Lys Phe Lys
            35                  40                  45
His Leu Lys Thr Glu Ala Glu Met Lys Ala Ser Glu Asp Leu Lys Lys
        50                  55                  60
His Gly Asn Thr Val Leu Thr Ala Leu Gly Gly Ile Leu Lys Lys Lys
65                  70                  75                  80
Gly His His Glu Ala Glu Val Lys His Leu Ala Glu Ser His Ala Asn
                85                  90                  95
```

Figure 4 - Continued

```
Lys His Lys Ile Pro Val Lys Tyr Leu Glu Phe Ile Ser Asp Ala Ile
            100                 105                 110
Ile His Val Leu His Ala Lys His Pro Ser Asp Phe Gly Ala Asp Ala
        115                 120                 125
Gln Ala Ala Met Ser Lys Ala Leu Glu Leu Phe Arg Asn Asp Met Ala
    130                 135                 140
Ala Gln Tyr Lys Val Leu Gly Phe His Gly
145                 150

<210> 19
<211> 154
<212> PRT
<213> Sus scrofa

<400> 19
Met Gly Leu Ser Asp Gly Glu Trp Gln Leu Val Leu Asn Val Trp Gly
  1               5                  10                  15
Lys Val Glu Ala Asp Val Ala Gly His Gly Gln Glu Val Leu Ile Arg
                20                  25                  30
Leu Phe Lys Gly His Pro Glu Thr Leu Glu Lys Phe Asp Lys Phe Lys
            35                  40                  45
His Leu Lys Ser Glu Asp Glu Met Lys Ala Ser Glu Asp Leu Lys Lys
        50                  55                  60
His Gly Asn Thr Val Leu Thr Ala Leu Gly Gly Ile Leu Lys Lys Lys
65                  70                  75                  80
Gly His His Glu Ala Glu Leu Thr Pro Leu Ala Gln Ser His Ala Thr
                85                  90                  95
Lys His Lys Ile Pro Val Lys Tyr Leu Glu Phe Ile Ser Glu Ala Ile
            100                 105                 110
Ile Gln Val Leu Gln Ser Lys His Pro Gly Asp Phe Gly Ala Asp Ala
        115                 120                 125
Gln Gly Ala Met Ser Lys Ala Leu Glu Leu Phe Arg Asn Asp Met Ala
    130                 135                 140
Ala Lys Tyr Lys Glu Leu Gly Phe Gln Gly
145                 150

<210> 20
<211> 154
<212> PRT
<213> Equus caballus

<400> 20
Met Gly Leu Ser Asp Gly Glu Trp Gln Gln Val Leu Asn Val Trp Gly
  1               5                  10                  15
```

Figure 4 - Continued

```
Lys Val Glu Ala Asp Ile Ala Gly His Gly Gln Glu Val Leu Ile Arg
            20                  25                  30
Leu Phe Thr Gly His Pro Glu Thr Leu Glu Lys Phe Asp Lys Phe Lys
        35                  40                  45
His Leu Lys Thr Glu Ala Glu Met Lys Ala Ser Glu Asp Leu Lys Lys
    50                  55                  60
His Gly Thr Val Val Leu Thr Ala Leu Gly Gly Ile Leu Lys Lys Lys
65                  70                  75                  80
Gly His His Glu Ala Glu Leu Lys Pro Leu Ala Gln Ser His Ala Thr
                85                  90                  95
Lys His Lys Ile Pro Ile Lys Tyr Leu Glu Phe Ile Ser Asp Ala Ile
            100                 105                 110
Ile His Val Leu His Ser Lys His Pro Gly Asp Phe Gly Ala Asp Ala
        115                 120                 125
Gln Gly Ala Met Thr Lys Ala Leu Glu Leu Phe Arg Asn Asp Ile Ala
    130                 135                 140
Ala Lys Tyr Lys Glu Leu Gly Phe Gln Gly
145                 150
```

<210> 21
<211> 152
<212> PRT
<213> Nicotiana benthamiana

<400> 21
```
Met Ser Ser Phe Thr Glu Glu Gln Glu Ala Leu Val Val Lys Ser Trp
1               5                   10                  15
Asp Ser Met Lys Lys Asn Ala Gly Glu Trp Gly Leu Lys Leu Phe Leu
            20                  25                  30
Lys Ile Phe Glu Ile Ala Pro Ser Ala Lys Lys Leu Phe Ser Phe Leu
        35                  40                  45
Lys Asp Ser Asn Val Pro Leu Glu Gln Asn Ala Lys Leu Lys Pro His
    50                  55                  60
Ser Lys Ser Val Phe Val Met Thr Cys Glu Ala Ala Val Gln Leu Arg
65                  70                  75                  80
Lys Ala Gly Lys Val Val Val Arg Asp Ser Thr Leu Lys Lys Leu Gly
                85                  90                  95
Ala Thr His Phe Lys Tyr Gly Val Ala Asp Glu His Phe Glu Val Thr
            100                 105                 110
Lys Phe Ala Leu Leu Glu Thr Ile Lys Glu Ala Val Pro Glu Met Trp
        115                 120                 125
Ser Val Asp Met Lys Asn Ala Trp Gly Glu Ala Phe Asp Gln Leu Val
    130                 135                 140
Asn Ala Ile Lys Thr Glu Met Lys
145                 150
```

Figure 4 - Continued

```
<210> 22
<211> 132
<212> PRT
<213> Bacillus subtilis

<400> 22
Met Gly Gln Ser Phe Asn Ala Pro Tyr Glu Ala Ile Gly Glu Glu Leu
 1               5                  10                  15
Leu Ser Gln Leu Val Asp Thr Phe Tyr Glu Arg Val Ala Ser His Pro
                20                  25                  30
Leu Leu Lys Pro Ile Phe Pro Ser Asp Leu Thr Glu Thr Ala Arg Lys
                35                  40                  45
Gln Lys Gln Phe Leu Thr Gln Tyr Leu Gly Gly Pro Pro Leu Tyr Thr
            50                  55                  60
Glu Glu His Gly His Pro Met Leu Arg Ala Arg His Leu Pro Phe Pro
65                  70                  75                  80
Ile Thr Asn Glu Arg Ala Asp Ala Trp Leu Ser Cys Met Lys Asp Ala
                85                  90                  95
Met Asp His Val Gly Leu Glu Gly Glu Ile Arg Glu Phe Leu Phe Gly
                100                 105                 110
Arg Leu Glu Leu Thr Ala Arg His Met Val Asn Gln Thr Glu Ala Glu
            115                 120                 125
Asp Arg Ser Ser
            130

<210> 23
<211> 131
<212> PRT
<213> Corynebacterium glutamicum

<400> 23
Met Thr Thr Ser Glu Asn Phe Tyr Asp Ser Val Gly Gly Glu Glu Thr
 1               5                  10                  15
Phe Ser Leu Ile Val His Arg Phe Tyr Glu Gln Val Pro Asn Asp Asp
                20                  25                  30
Ile Leu Gly Pro Met Tyr Pro Pro Asp Asp Phe Glu Gly Ala Glu Gln
                35                  40                  45
Arg Leu Lys Met Phe Leu Ser Gln Tyr Trp Gly Gly Pro Lys Asp Tyr
            50                  55                  60
Gln Glu Gln Arg Gly His Pro Arg Leu Arg Met Arg His Val Asn Tyr
65                  70                  75                  80
Pro Ile Gly Val Thr Ala Ala Glu Arg Trp Leu Gln Leu Met Ser Asn
                85                  90                  95
Ala Leu Asp Gly Val Asp Leu Thr Ala Glu Gln Arg Glu Ala Ile Trp
                100                 105                 110
```

Figure 4 - Continued

```
Glu His Met Val Arg Ala Ala Asp Met Leu Ile Asn Ser Asn Pro Asp
        115                 120                 125
Pro His Ala
    130

<210> 24
<211> 124
<212> PRT
<213> Synechocystis sp.

<400> 24
Met Ser Thr Leu Tyr Glu Lys Leu Gly Thr Thr Ala Val Asp Leu
  1           5                  10                  15
Ala Val Asp Lys Phe Tyr Glu Arg Val Leu Gln Asp Asp Arg Ile Lys
            20                  25                  30
His Phe Phe Ala Asp Val Asp Met Ala Lys Gln Arg Ala His Gln Lys
            35                  40                  45
Ala Phe Leu Thr Tyr Ala Phe Gly Gly Thr Asp Lys Tyr Asp Gly Arg
        50                  55                  60
Tyr Met Arg Glu Ala His Lys Glu Leu Val Glu Asn His Gly Leu Asn
 65                  70                  75                  80
Gly Glu His Phe Asp Ala Val Ala Glu Asp Leu Leu Ala Thr Leu Lys
                    85                  90                  95
Glu Met Gly Val Pro Glu Asp Leu Ile Ala Glu Val Ala Ala Val Ala
                100                 105                 110
Gly Ala Pro Ala His Lys Arg Asp Val Leu Asn Gln
            115                 120

<210> 25
<211> 183
<212> PRT
<213> Synechococcus sp.

<400> 25
Met Asp Val Ala Leu Leu Glu Lys Ser Phe Glu Gln Ile Ser Pro Arg
  1               5                  10                  15
Ala Ile Glu Phe Ser Ala Ser Phe Tyr Gln Asn Leu Phe His His His
            20                  25                  30
Pro Glu Leu Lys Pro Leu Phe Ala Glu Thr Ser Gln Thr Ile Gln Glu
            35                  40                  45
Lys Lys Leu Ile Phe Ser Leu Ala Ala Ile Ile Glu Asn Leu Arg Asn
        50                  55                  60
Pro Asp Ile Leu Gln Pro Ala Leu Lys Ser Leu Gly Ala Arg His Ala
 65                  70                  75                  80
```

Figure 4 - Continued

```
Glu Val Gly Thr Ile Lys Ser His Tyr Pro Leu Val Gly Gln Ala Leu
                 85                  90                  95
Ile Glu Thr Phe Ala Glu Tyr Leu Ala Ala Asp Trp Thr Glu Gln Leu
                100                 105                 110
Ala Thr Ala Trp Val Glu Ala Tyr Asp Val Ile Ala Ser Thr Met Ile
            115                 120                 125
Glu Gly Ala Asp Asn Pro Ala Ala Tyr Leu Glu Pro Glu Leu Thr Phe
        130                 135                 140
Tyr Glu Trp Leu Asp Leu Tyr Gly Glu Glu Ser Pro Lys Val Arg Asn
145                 150                 155                 160
Ala Ile Ala Thr Leu Thr His Phe His Tyr Gly Glu Asp Pro Gln Asp
                165                 170                 175
Val Gln Arg Asp Ser Arg Gly
                180
```

<210> 26
<211> 118
<212> PRT
<213> Nostoc commune

<400> 26
```
Met Ser Thr Leu Tyr Asp Asn Ile Gly Gly Gln Pro Ala Ile Glu Gln
  1               5                  10                  15
Val Val Asp Glu Leu His Lys Arg Ile Ala Thr Asp Ser Leu Leu Ala
                 20                  25                  30
Pro Val Phe Ala Gly Thr Asp Met Val Lys Gln Arg Asn His Leu Val
             35                  40                  45
Ala Phe Leu Ala Gln Ile Phe Glu Gly Pro Lys Gln Tyr Gly Gly Arg
         50                  55                  60
Pro Met Asp Lys Thr His Ala Gly Leu Asn Leu Gln Gln Pro His Phe
 65                  70                  75                  80
Asp Ala Ile Ala Lys His Leu Gly Glu Arg Met Ala Val Arg Gly Val
                 85                  90                  95
Ser Ala Glu Asn Thr Lys Ala Ala Leu Asp Arg Val Thr Asn Met Lys
                100                 105                 110
Gly Ala Ile Leu Asn Lys
            115
```

<210> 27
<211> 136
<212> PRT
<213> Bacillus megaterium

Met Arg Glu Lys Ile His Ser Pro Tyr Glu Leu Leu Gly Gly Glu His
1               5                   10                  15
Thr Ile Ser Lys Leu Val Asp Ala Phe Tyr Thr Arg Val Gly Gln His
            20                  25                  30
Pro Glu Leu Ala Pro Ile Phe Pro Asp Asn Leu Thr Glu Thr Ala Arg
        35                  40                  45
Lys Gln Lys Gln Phe Leu Thr Gln Tyr Leu Gly Gly Pro Ser Leu Tyr
    50                  55                  60
Thr Glu Glu His Gly His Pro Met Leu Arg Ala Arg His Leu Pro Phe
65                  70                  75                  80
Glu Ile Thr Pro Ser Arg Ala Lys Ala Trp Leu Thr Cys Met His Glu
                85                  90                  95
Ala Met Asp Glu Ile Asn Leu Glu Gly Pro Glu Arg Asp Glu Leu Tyr
            100                 105                 110
His Arg Leu Ile Leu Thr Ala Gln His Met Ile Asn Ser Pro Glu Gln
            115                 120                 125
Thr Asp Glu Lys Gly Phe Ser His
        130                 135

Figure 6

SEQ ID NO: 28

```
atggagtttg tcgcccgtca gtccatgaat gcctgtccct ttgtcaggtc aacttctacc    60
caccatttga agaagttggc agcaaacagt tctctagctg ctactgctag tcattgtccc   120
gtggttggcc ctgctctcca acagcagaga tactactctc aaccttccaa gccagcccaa   180
gcccaaacct ccgacattgc tactgggatc aagaaggatg tttctccgat ccgtatggac   240
tctaatgaaa ccgcctttga ttacaatgga atgtatgagt ctgatcttgc gaataaacgt   300
aaagataact cgtatcgtta tttcaataac atcaaccgtc tagccaagga gtttcccaag   360
gcacatcgcc agaccgaaga tgacaaggtg accgtctggt gctctaacga ctacttagga   420
atgggtaggc atcctgagat tatcaaaacc atgaaggcta ccatggacaa gtacggttcc   480
ggagcaggag gaactaggaa cattgcaggt cataaccacg ccgctatcaa tttggaaagc   540
gagttggctt gcttgaacaa gaaggaagcg gctctggtgt tttcatcatg tttcatagct   600
aacgatgcaa tcatctcgtt gttgggacaa aaaatcaaaa atttggtcat tttctctgac   660
cagtcgaatc atgcttccat gatattgggt gtgcgtaact ccaaagcgaa gaagcacatc   720
ttcaagcaca acaatttgaa ggatctggag tcgcagttag ctcagtaccc caagtcgact   780
cctaaactga tcgccttcga gtcagtttac tctatgtgtg atctgtggc tcccattgag   840
aagatttgcg atttggctaa aaggtacggt gccctcacct tcttggatga agttcatgct   900
gttggaatgt atggtcctca tggacagggt gtagctgagc atttggactt tgatctgcat   960
ttacagtctg gaatcgccag tcctagcgtg gtggacaaac gcaccatatt ggatcgtgtc  1020
gacatgatta ctggtacttg cggaaagtca tttggtactg ttggaggtta cgttgctggt  1080
agtgccaacc taattgattg gttaagatcc tatgcgccag gtttcatttt cactaccaca  1140
cttcctcctg ctatcatggc tggtacagcc acttctgttc gtattgttag gccgacatt   1200
gaggcccgta tcaagcaaca gcttaatact cgctacgtta agactcatt tgaaaacctt  1260
ggtattccag tcattccaaa cccaagtcac attgttcctg ttctagttgg aaatgctgca  1320
gatgccaaga aggcatccga tatgttaatg aacaaacacc gtatttatgt tcaagctatt  1380
aactacccta ctgtgcctgt cggtgaagaa cgactaagga ttactcctac tccaggtcat  1440
ggaaaggaga tttgtgacca gctgatcagc gctgtcgacg atgttttac tgagcttaat   1500
ttaccaagaa tcaacaaatg gcagtcccaa ggtggtcatt gcggtgttgg tgatgctaat  1560
tacgtaccag aacccaatct gtggactcag gaccagctca gcttgacaaa ccaagacttg  1620
cactccaatg tgcacaaccc agtgattgag cagatcgaaa cctcatcagg agtcagattg  1680
tag                                                                1683
```

SEQ ID NO: 29

```
        10         20         30         40         50
MEFVARQSMN ACPFVRSTST HHLKKLAANS SLAATASHCP VVGPALQQQR
        60         70         80         90        100
YYSQPSKPAQ AQTSDIATGI KKDVSPIRMD SNETAFDYNG MYESDLANKR
       110        120        130        140        150
KDNSYRYFNN INRLAKEFPK AHRQTEDDKV TVWCSNDYLG MGRHPEIIKT
       160        170        180        190        200
MKATMDKYGS GAGGTRNIAG HNHAAINLES ELACLNKKEA ALVFSSCFIA
       210        220        230        240        250
NDAIISLLGQ KIKNLVIFSD QSNHASMILG VRNSKAKKHI FKHNNLKDLE
       260        270        280        290        300
SQLAQYPKST PKLIAFESVY SMCGSVAPIE KICDLAKRYG ALTFLDEVHA
       310        320        330        340        350
VGMYGPHGQG VAEHLDFDLH LQSGIASPSV VDKRTILDRV DMITGTCGKS
       360        370        380        390        400
FGTVGGYVAG SANLIDWLRS YAPGFIFTTT LPPAIMAGTA TSVRIVRADI
       410        420        430        440        450
```

Figure 6 - Continued

```
EARIKQQLNT  RYVKDSFENL  GIPVIPNPSH  IVPVLVGNAA  DAKKASDMLM
       460         470         480         490         500
NKHRIYVQAI  NYPTVPVGEE  RLRITPTPGH  GKEICDQLIS  AVDDVFTELN
       510         520         530         540         550
LPRINKWQSQ  GGHCGVGDAN  YVPEPNLWTQ  DQLSLTNQDL  HSNVHNPVIE
       560
QIETSSGVRL
```

Figure 7

Sequence of an exemplary mutant ALAS gene and protein

Gene sequence (SEQ ID NO: 30):

ATGGAGTTTGTCGCCCGTCAGTCCATGAATGCCTCTCCCTTTGTCAGGTCAACTTCTACCCACC
ATTTGAAGAAGTTGGCAGCAAACAGTTCTCTAGCTGCTACTGCTAGTCATTCTCCCGTGGTTGG
CCCTGCTCTCCAACAGCAGAGATACTACTCTCAACCTTCCAAGCCAGCCCAAGCCCAAACCTCC
GACATTGCTACTGGGATCAAGAAGGATGTTTCTCCGATCCGTATGGACTCTAATGAAACCGCCT
TTGATTACAATGGAATGTATGAGTCTGATCTTGCGAATAAACGTAAAGATAACTCGTATCGTTA
TTTCAATAACATCAACCGTCTAGCCAAGGAGTTTCCCAAGGCACATCGCCAGACCGAAGATGAC
AAGGTGACCGTCTGGTGCTCTAACGACTACTTAGGAATGGGTAGGCATCCTGAGATTATCAAAA
CCATGAAGGCTACCATGGACAAGTACGGTTCCGGAGCAGGAGGAACTAGGAACATTGCAGGTCA
TAACCACGCCGCTATCAATTTGGAAAGCGAGTTGGCTTGCTTGAACAAGAAGGAAGCGGCTCTG
GTGTTTTCATCATGTTTCATAGCTAACGATGCAATCATCTCGTTGTTGGGACAAAAAATCAAAA
ATTTGGTCATTTTCTCTGACCAGTCGAATCATGCTTCCATGATATTGGGTGTGCGTAACTCCAA
AGCGAAGAAGCACATCTTCAAGCACAACAATTTGAAGGATCTGGAGTCGCAGTTAGCTCAGTAC
CCCAAGTCGACTCCTAAACTGATCGCCTTCGAGTCAGTTTACTCTATGTGTGGATCTGTGGCTC
CCATTGAGAAGATTTGCGATTTGGCTAAAAGGTACGGTGCCCTCACCTTCTTGGATGAAGTTCA
TGCTGTTGGAATGTATGGTCCTCATGGACAGGGTGTAGCTGAGCATTTGGACTTTGATCTGCAT
TTACAGTCTGGAATCGCCAGTCCTAGCGTGGTGGACAAACGCACCATATTGGATCGTGTCGACA
TGATTACTGGTACTTGCGGAAAGTCATTTGGTACTGTTGGAGGTTACGTTGCTGGTAGTGCCAA
CCTAATTGATTGGTTAAGATCCTATGCGCCAGGTTTCATTTTCACTACCACACTTCCTCCTGCT
ATCATGGCTGGTACAGCCACTTCTGTTCGTATTGTTAGGGCCGACATTGAGGCCCGTATCAAGC
AACAGCTTAATACTCGCTACGTCAAAGACTCATTTGAAAACCTTGGTATTCCAGTCATTCCAAA
CCCAAGTCACATTGTTCCTGTTCTAGTTGGAAATGCTGCAGATGCCAAGAAGGCATCCGATATG
TTAATGAACAAACACCGTATTTATGTTCAAGCTATTAACTACCCTACTGTGCCTGTCGGTGAAG
AACGACTAAGGATTACTCCTACTCCAGGTCATGGAAAGGAGATTTGTGACCAGCTGATCAGCGC
TGTCGACGATGTTTTTACTGAGCTTAATTTACCAAGAATCAACAAATGGCAGTCCCAAGGTGGT
CATTGCGGTGTTGGTGATGCTAATTACGTACCAGAACCCAATCTGTGGACTCAGGACCAGCTCA
GCTTGACAAACCAAGACTTGCACTCCAATGTGCACAACCCAGTGATTGAGCAGATCGAAACCTC
ATCAGGAGTCAGATTGTAG

Figure 7 - Continued

Mutated codons (TGT in wild-type to TCT in mutant) are indicated in bold and double underlined.

Protein sequence (SEQ ID NO: 31):

MEFVARQSMNASPFVRSTSTHHLKKLAANSSLAATASHSPVVGPALQQQRYYSQPSKPAQAQTS
DIATGIKKDVSPIRMDSNETAFDYNGMYESDLANKRKDNSYRYFNNINRLAKEFPKAHRQTEDD
KVTVWCSNDYLGMGRHPEIIKTMKATMDKYGSGAGGTRNIAGHNHAAINLESELACLNKKEAAL
VFSSCFIANDAIISLLGQKIKNLVIFSDQSNHASMILGVRNSKAKKHIFKHNNLKDLESQLAQY
PKSTPKLIAFESVYSMCGSVAPIEKICDLAKRYGALTFLDEVHAVGMYGPHGQGVAEHLDFDLH
LQSGIASPSVVDKRTILDRVDMITGTCGKSFGTVGGYVAGSANLIDWLRSYAPGFIFTTTLPPA
IMAGTATSVRIVRADIEARIKQQLNTRYVKDSFENLGIPVIPNPSHIVPVLVGNAADAKKASDM
LMNKHRIYVQAINYPTVPVGEERLRITPTPGHGKEICDQLISAVDDVFTELNLPRINKWQSQGG
HCGVGDANYVPEPNLWTQDQLSLTNQDLHSNVHNPVIEQIETSSGVRL

Length: 560 aa
Mol wt: 61.5 kDa

Two cysteine residues present in wtALAS were mutated to serine (bold and double underlined): C12S and C39S.

Figure 8

SEQ ID NO: 32
R/L/N/A/C/S/H/I/G/Q-C-P-L/V/I/F/C-L/M/P/V

SEQ ID NO: 33
A-C-P-F-V

SEQ ID NO: 34
H-C-P-V-V

SEQ ID NO: 35
I-C-P-F-M

SEQ ID NO: 36
G-C-P-V-V

SEQ ID NO: 37
CGTCAGTCCATGAATGCCTCTCCCTTTGTCAGGTCAACTTC

SEQ ID NO: 38
GAAGTTGACCTGACAAAGGGAGAGGCATTCATGGACTGACG

SEQ ID NO: 39
GCTGCTACTGCTAGTCATTCTCCCGTGGTTGGCCCTG

SEQ ID NO: 40
CAGGGCCAACCACGGGAGAATGACTAGCAGTAGCAGC

SEQ ID NO: 41
AAACGCTGTCTTGGAACCTAATATGAC

SEQ ID NO: 42
GACGGGCGACAAACTCCATCGTTTCGAATAATTAGTTG

SEQ ID NO: 43
CAACTAATTATTCGAAACGATGGAGTTTGTCGCCCGTCAG

SEQ ID NO: 44
AATTAAATACATTTCAACTACAATCTGACTCCTGATGAGGTTTCG

SEQ ID NO: 45
CCTCATCAGGAGTCAGATTGTAGTTGAAATGTATTTAATTTG

SEQ ID NO: 46
AAACTGTCAGTTTTGGGCCATTTG

Figure 8 - Continued

SEQ ID NO: 47
GCTCTCCAACAGCAGAGATAC

SEQ ID NO: 48
GTCCATACGGATCGGAGAAAC

SEQ ID NO: 49
AGCAACATCCCTGATTCCG

SEQ ID NO: 50
ATGCGTACCTTCAATCCTGG

SEQ ID NO: 51
6-FAM/AAGCCCAAA/Zen/CCTCCGA CATTGCTA/3IABkFQ

SEQ ID NO: 52
HEX/TCGCCGTAA/Zen/GTTCTTGGTT TAGACGTTC/3IABkFQ

SEQ ID NO: 53
TAGCGCAGTCTCTATCGCTTC

SEQ ID NO: 54
CACTGGGTTGTGCACATTGG

SEQ ID NO: 55
ACAATATTCTTCTCTGCCGC

SEQ ID NO: 56
TTGATCTCGTCAAGAATGCG

SEQ ID NO: 57
TAGGTGCCACAACTTTTGGTTTC

SEQ ID NO: 58
GATCCAATGCGATGACATTCTTGT

SEQ ID NO: 59
ACCTGCAATAACTCCTCTTCTCTG

SEQ ID NO: 60
CCACTGAGGGTAGCCGAATC

SEQ ID NO: 61
GGGCTCTGAAAACTCTTTTGG

Figure 8 - Continued

SEQ ID NO: 62
GCATGTCTCAATAACAGATCTCGACGG

SEQ ID NO: 63
AAGCCTCTTGTTTTTCTGTAAATGCAC

SEQ ID NO: 64
TGATGGCGTCCGAGATGAACTC

SEQ ID NO: 65
ATGGAGTTTGTCGCCCGTCAG

SEQ ID NO: 66
CTACAATCTGACTCCTGATGAGGTTTC

MATERIALS AND METHODS FOR PROTEIN PRODUCTION

CROSS-REFERENCE TO RELATED APPLICATIONS

This application claims priority to U.S. Provisional Application Ser. No. 62/838,770, filed on Apr. 25, 2019, which is incorporated by reference herein in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing filename: 38767-0158001.txt, date recorded, Apr. 24, 2020, file size ≈69 kilobytes.

TECHNICAL FIELD

This disclosure generally relates to DNA constructs and methods of using such DNA constructs to genetically engineer cells (e.g., yeast cells (e.g., methylotrophic yeast cells)).

BACKGROUND

Cells such as *Pichia pastoris* are commonly used for expression of recombinant proteins. Constructs that can be used to efficiently express one or more proteins in a cell (e.g., fungal cell, such as an *Aspergillus* cell, a *Trichoderma* cell, or a yeast cell (e.g., a methylotrophic yeast cell)) are provided herein.

SUMMARY

This document is based, at least in part, on the identification of mutations in aminolevulinic acid synthase (ALAS) that can confer increased expression of heme-binding proteins. The mutated ALAS proteins described herein can be used for the efficient expression of heme-binding proteins in *Pichia*, for example.

In one aspect, provided herein is a methylotrophic yeast cell including a first exogenous nucleic acid construct comprising a nucleotide sequence encoding an aminolevulinate synthase (ALAS) protein operably linked to a first promoter element, wherein the ALAS includes a first mutation in a first heme responsive motif (HRM) and a second exogenous nucleic acid construct comprising a nucleotide sequence encoding a heme-binding protein, wherein the second exogenous nucleic acid construct comprising a nucleotide sequence encoding the heme-binding protein is operably linked to the first promoter element or is operably linked to a second promoter element.

Implementations can have one or more of the following features. The methylotrophic yeast cell can be a *Pichia* cell, a *Candida* cell, a *Hansenula* cell, or a *Torulopsis* cell. The methylotrophic yeast cell can be a *Pichia methanolica* cell, a *Pichia pastoris* cell, a *Candida boidinii* cell, or a *Hansenula polymorpha* cell. The methylotrophic yeast cell can be a *Pichia pastoris* cell. The first mutation can be a cysteine to serine mutation. The first mutation can be a cysteine to alanine mutation. The ALAS can include a second mutation in a second HRM. The second mutation can be a cysteine to serine mutation. The second mutation can be a cysteine to alanine mutation. The first exogenous nucleic acid construct can include a nucleic acid sequence having at least 90% sequence identity to the nucleic acid sequence in SEQ ID NO: 28. The first exogenous nucleic acid construct can include a nucleic acid sequence having at least 95% sequence identity to the nucleic acid sequence in SEQ ID NO: 28. The ALAS protein can include an amino acid sequence having at least 90% sequence identity to the amino acid sequence in SEQ ID NO: 29. The ALAS protein can include an amino acid sequence having at least 95% sequence identity to the amino acid sequence in SEQ ID NO: 29. The heme-binding protein can be selected from the group consisting of a globin, a cytochrome, a cytochrome c oxidase, a ligninase, a catalase, and a peroxidase. The heme-binding protein can be selected from the group consisting of an androglobin, a chlorocruorin, a cytoglobin, an erythrocruorin, a flavohemoglobin, a globin E, a globin X, a globin Y, a hemoglobin, a histoglobin, a leghemoglobin, a myoglobin, a neuroglobin, a non-symbiotic hemoglobin, a protoglobin, and a truncated hemoglobin. The heme-binding protein can be a non-symbiotic hemoglobin. The heme-binding protein can be a leghemoglobin. The heme-binding protein can include an amino acid sequence having at least 90% sequence identity to an amino acid sequence in any one of SEQ ID NOs: 1-27. The methylotrophic yeast cell can further include a third nucleic acid construct comprising a nucleotide sequence encoding a transcription factor, wherein the third nucleic acid construct is operably linked to the first promoter element, the second promoter element, or a third promoter element. The first promoter element can include a recognition sequence for the transcription factor. The second exogenous nucleic acid construct can be operably linked to a second promoter element, and wherein the second promoter element includes a recognition sequence for the transcription factor. The third nucleic acid construct can be operably linked to the third promoter element, and wherein the third promoter element includes a recognition sequence for the transcription factor. The methylotrophic yeast cell can further include a fourth nucleic acid construct comprising a nucleotide sequence encoding a protein involved in heme biosynthesis, wherein the fourth nucleic acid construct is operably linked to the first promoter element, the second promoter element, the third promoter element, or a fourth promoter element. The protein involved in heme biosynthesis can be selected from the group consisting of ALA dehydratase, porphobilinogen deaminase, UPG III synthase, UPG III decarboxylase, CPG oxidase, PPG oxidase, and ferrochelatase. The first exogenous nucleic acid construct can be a heterologous nucleic acid construct. The second exogenous nucleic acid construct can be a heterologous nucleic acid construct. The heme-binding protein can be an exogenous heme-binding protein. The heme-binding protein can be a heterologous heme-binding protein.

In another aspect, provided herein is a method of producing a heme-binding protein in a methylotrophic yeast cell including expressing a first exogenous nucleic acid construct comprising a nucleotide sequence encoding an aminolevulinate synthase (ALAS) protein operably linked to a first promoter element, wherein the ALAS includes a first mutation in a first heme responsive motif (HRM) and expressing a second exogenous nucleic acid construct comprising a nucleotide sequence encoding a heme-binding protein, wherein the second exogenous nucleic acid construct comprising a nucleotide sequence encoding the heme-binding protein is operably linked to the first promoter element or is operably linked to a second promoter element.

Implementations can have one or more of the following features. The ALAS can include a second mutation in a second HRM. The method can produce the heme-binding protein in a titer that is at least 5% greater than a corresponding method lacking the first exogenous nucleic acid construct. The method can produce the heme-binding protein in a titer that is at least 10% greater than a corresponding method lacking the first exogenous nucleic acid construct. The method can produce the heme-binding protein in a titer that is at least 15% greater than a corresponding method lacking the first exogenous nucleic acid construct. The method can produce the heme-binding protein in a titer that is at least 20% greater than a corresponding method lacking the first exogenous nucleic acid construct. The method can produce the heme-binding protein in a titer that is at least 5% greater than a corresponding method lacking the first mutation. The method can produce the heme-binding protein in a titer that is at least 10% greater than a corresponding method lacking the first mutation. The method can produce the heme-binding protein in a titer that is at least 15% greater than a corresponding method lacking the first mutation. The method can produce the heme-binding protein in a titer that is at least 20% greater than a corresponding method lacking the first mutation. The method can produce the heme-binding protein in a titer that is at least 5% greater than a corresponding method lacking the first mutation and the second mutation. The method can produce the heme-binding protein in a titer that is at least 10% greater than a corresponding method lacking the first mutation and the second mutation. The method can produce the heme-binding protein in a titer that is at least 15% greater than a corresponding method lacking the first mutation and the second mutation. The method can produce the heme-binding protein in a titer that is at least 20% greater than a corresponding method lacking the first mutation and the second mutation. The method can be carried out in the absence of added methanol. The methylotrophic yeast cell can be a *Pichia* cell, a *Candida* cell, a *Hansenula* cell, or a *Torulopsis* cell. The methylotrophic yeast cell can be a *Pichia methanolica* cell, a *Pichia pastoris* cell, a *Candida boidinii* cell, or a *Hansenula polymorpha* cell. The methylotrophic yeast cell can be a *Pichia pastoris* cell. The first mutation can be a cysteine to serine mutation. The first mutation can be a cysteine to alanine mutation. The second mutation can be a cysteine to serine mutation. The second mutation can be a cysteine to alanine mutation. The first exogenous nucleic acid construct can include a nucleic acid sequence having at least 90% sequence identity to the nucleic acid sequence in SEQ ID NO: 28. The first exogenous nucleic acid construct can include a nucleic acid sequence having at least 95% sequence identity to the nucleic acid sequence in SEQ ID NO: 28. The ALAS protein can include an amino acid sequence having at least 90% sequence identity to the amino acid sequence in SEQ ID NO: 29. The ALAS protein can include an amino acid sequence having at least 95% sequence identity to the amino acid sequence in SEQ ID NO: 29. The heme-binding protein can be selected from the group consisting of a globin, a cytochrome, a cytochrome c oxidase, a ligninase, a catalase, and a peroxidase. The heme-binding protein can be selected from the group consisting of an androglobin, a chlorocruorin, a cytoglobin, an erythrocruorin, a flavohemoglobin, a globin E, a globin X, a globin Y, a hemoglobin, a histoglobin, a leghemoglobin, a myoglobin, a neuroglobin, a non-symbiotic hemoglobin, a protoglobin, and a truncated hemoglobin. The heme-binding protein can be a non-symbiotic hemoglobin. The heme-binding protein can be a leghemoglobin. The heterologous heme-binding protein can include an amino acid sequence having at least 90% sequence identity to an amino acid sequence in any one of SEQ ID NOs: 1-27. The method can further include expressing a third nucleic acid construct comprising a nucleotide sequence encoding a transcription factor, wherein the third nucleic acid construct is operably linked to the first promoter element, the second promoter element, or a third promoter element. The first promoter element can include a recognition sequence for the transcription factor. The second exogenous nucleic acid construct can be operably linked to a second promoter element, and wherein the second promoter element includes a recognition sequence for the transcription factor. The third nucleic acid construct can be operably linked to the third promoter element, and wherein the third promoter element includes a recognition sequence for the transcription factor. The method can further include expressing a fourth nucleic acid construct comprising a nucleotide sequence encoding a protein involved in heme biosynthesis, wherein the fourth nucleic acid construct is operably linked to the first promoter element, the second promoter element, the third promoter element, or a fourth promoter element. The protein involved in heme biosynthesis can be selected from the group consisting of ALA dehydratase, porphobilinogen deaminase, UPG III synthase, UPG III decarboxylase, CPG oxidase, PPG oxidase, and ferrochelatase. The first exogenous nucleic acid construct can be a heterologous nucleic acid construct. The second exogenous nucleic acid construct can be a heterologous nucleic acid construct. The heme-binding protein can be an exogenous heme-binding protein. The heme-binding protein can be a heterologous heme-binding protein.

In another aspect, provided herein is a *Pichia pastoris* cell including a first exogenous nucleic acid construct comprising a nucleotide sequence encoding an aminolevulinate synthase (ALAS) protein operably linked to a first promoter element, wherein the ALAS includes a first mutation in a first heme responsive motif (HRM) and a second mutation in a second HRM and a second exogenous nucleic acid construct comprising a nucleotide sequence encoding leghemoglobin, wherein the second exogenous nucleic acid construct comprising a nucleotide sequence encoding leghemoglobin is operably linked to the first promoter element, or the second exogenous nucleic acid construct comprising a nucleotide sequence encoding leghemoglobin is operably linked to a second promoter element.

Implementations can include one or more of the following features. The first mutation can be a cysteine to serine mutation. The second mutation can be a cysteine to serine mutation.

In another aspect, provided herein is a method of producing leghemoglobin, the method including expressing a first exogenous nucleic acid construct comprising a nucleotide sequence encoding an aminolevulinate synthase (ALAS) protein operably linked to a first promoter element, wherein the ALAS includes a first mutation in a first heme responsive motif (HRM) and a second mutation in a second HRM and expressing a second exogenous nucleic acid construct comprising a nucleotide sequence encoding leghemoglobin, wherein the second exogenous nucleic acid construct comprising a nucleotide sequence encoding leghemoglobin is operably linked to the first promoter element, or the second exogenous nucleic acid construct comprising a nucleotide sequence encoding leghemoglobin is operably linked to a second promoter element.

Implementations can have one or more of the following features. The method can produce the leghemoglobin in a titer that is at least 5% greater than a corresponding method lacking the first exogenous nucleic acid construct. The method can produce the leghemoglobin in a titer that is at least 10% greater than a corresponding method lacking the first exogenous nucleic acid construct. The method can produce the leghemoglobin in a titer that is at least 15% greater than a corresponding method lacking the first exogenous nucleic acid construct. The method can produce the leghemoglobin in a titer that is at least 20% greater than a corresponding method lacking the first exogenous nucleic acid construct. The method can produce the leghemoglobin in a titer that is at least 5% greater than a corresponding method lacking the first mutation and the second mutation. The method can produce the leghemoglobin in a titer that is at least 10% greater than a corresponding method lacking the first mutation and the second mutation. The method can produce the leghemoglobin in a titer that is at least 15% greater than a corresponding method lacking the first mutation and the second mutation. The method can produce the leghemoglobin in a titer that is at least 20% greater than a corresponding method lacking the first mutation and the second mutation. The method can be carried out in the absence of added methanol.

In another aspect, provided herein is a *Pichia pastoris* cell including a first exogenous nucleic acid construct comprising a nucleotide sequence encoding a protein with at least 90% sequence identity to SEQ ID NO: 29, wherein the nucleic acid encodes a serine residue in a position corresponding to position 12 of SEQ ID NO: 29, and wherein the nucleic acid encodes a serine residue in a position corresponding to position 39 of SEQ ID NO: 29, operably linked to a first promoter element.

Implementations can include one or more of the following features. The *Pichia pastoris* cell can further include a second exogenous nucleic acid construct comprising a nucleotide sequence encoding a protein with at least 90% sequence identity to any of SEQ ID NOs: 1-27, wherein the second exogenous nucleic acid construct is operably linked to the first promoter element, or the second exogenous nucleic acid construct is operably linked to a second promoter element. The *Pichia pastoris* cell can further include a second exogenous nucleic acid construct comprising a nucleotide sequence encoding a protein with at least 90% sequence identity to SEQ ID NO: 4, wherein the second exogenous nucleic acid construct is operably linked to the first promoter element, or the second exogenous nucleic acid construct is operably linked to a second promoter element.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the disclosure are set forth in the accompanying drawings and the description below. Other features, objects, and advantages of the disclosure will be apparent from the description and drawings, and from the claims. The word "comprising" in the claims may be replaced by "consisting essentially of" or with "consisting of," according to standard practice in patent law.

DESCRIPTION OF THE DRAWINGS

FIG. 4 provides the sequences of exemplary heme-binding proteins (SEQ ID NOs: 1-27).

FIG. 6 provides the nucleic acid sequence (SEQ ID NO: 28) and amino acid sequence (SEQ ID NO: 29) of wild-type ALAS.

FIG. 7 provides the nucleic acid sequence (SEQ ID NO: 30) and amino acid sequence (SEQ ID NO: 31) of an exemplary mutant ALAS.

FIG. 8 provides the sequences of SEQ ID NOs: 32-66.

DETAILED DESCRIPTION

This document is related to materials and methods for protein production. In particular, this document is related to materials and method for the production of heme and heme-binding proteins.

Methylotrophic yeast, such as *Pichia pastoris*, are commonly used to produce recombinant proteins. *Pichia* strains are typically able to grow using methanol as the sole carbon source. It will be understood that *Pichia pastoris* has been reclassified as *Komagataella* species, such as *Komagataella phaffii*, *Komagataella pastoris*, or *Komagataella pseudopastoris*, though the term '*Pichia pastoris*' is still in use and may refer to any appropriate *Komagataella* species. Commonly, laboratory strains of *P. pastoris* are *Komagataella phaffii*.

Figure 1:
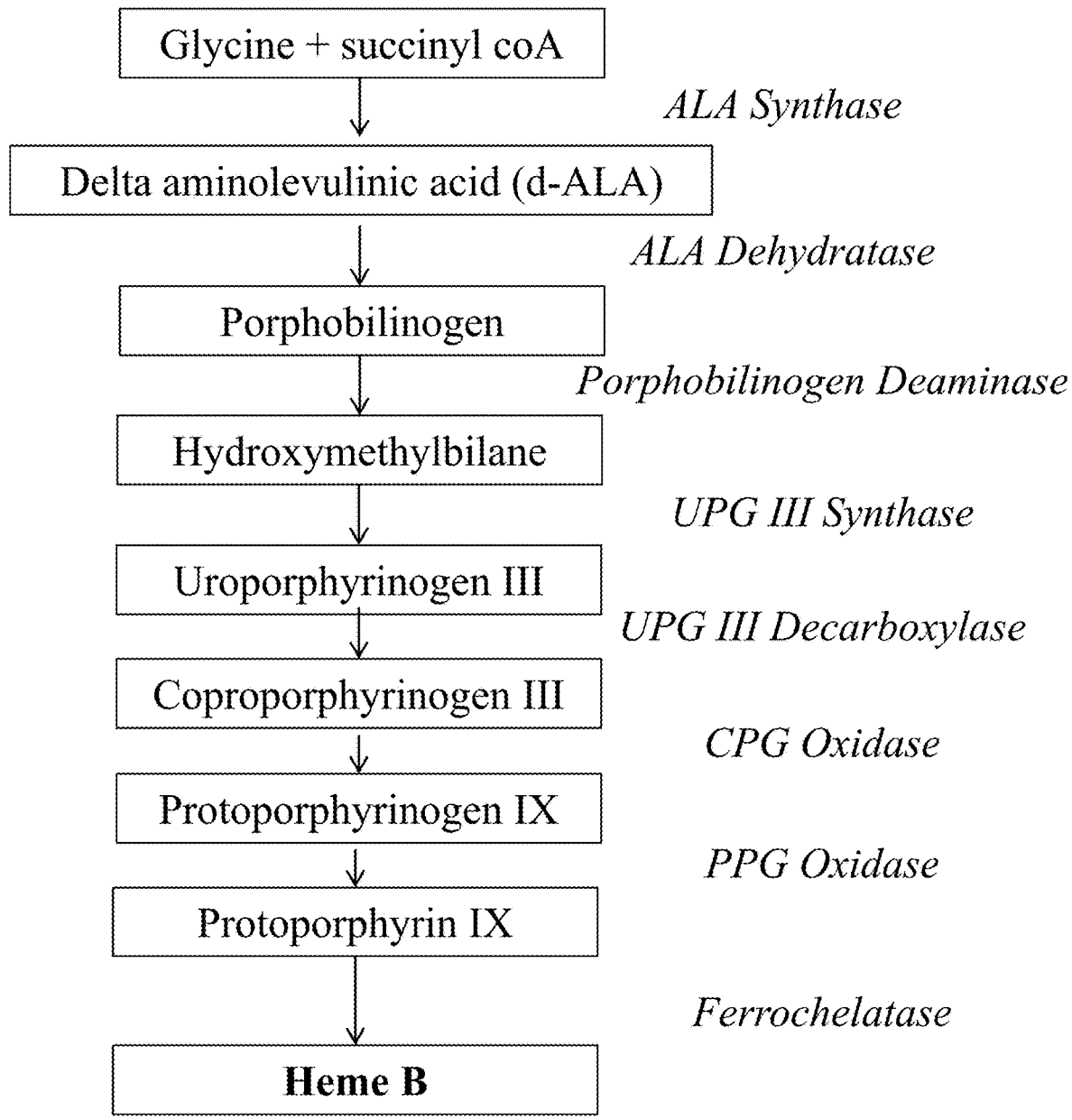
FIG. 1 provides a schematic depicting the steps involved in the heme biosynthesis pathway.
Figure 2:
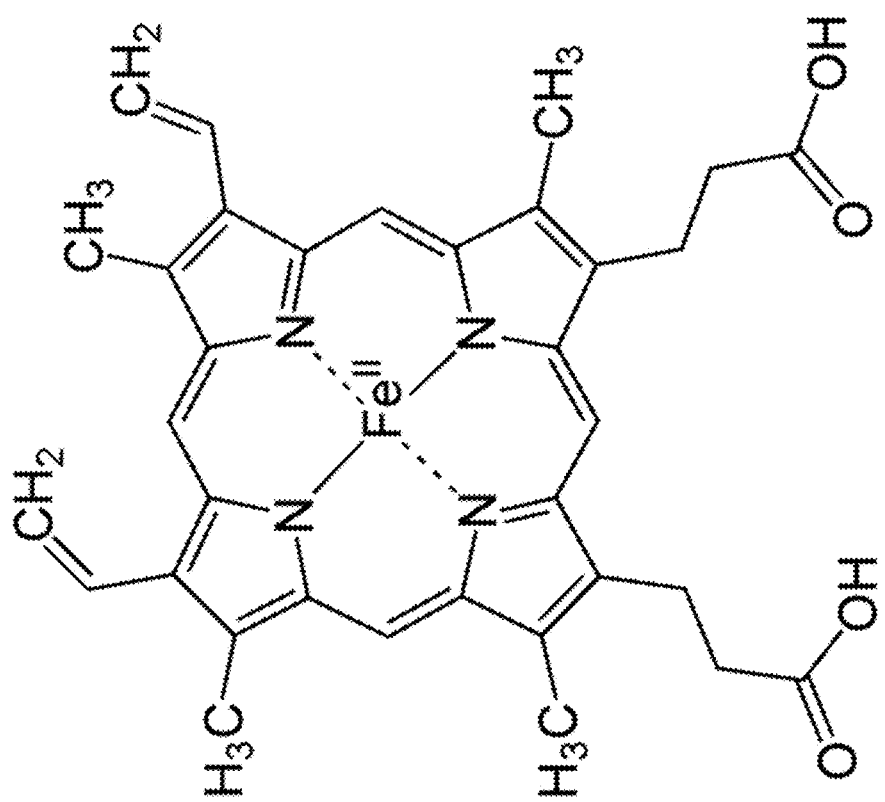
FIG. 2 provides a structure of Heme b.
Figure 3:
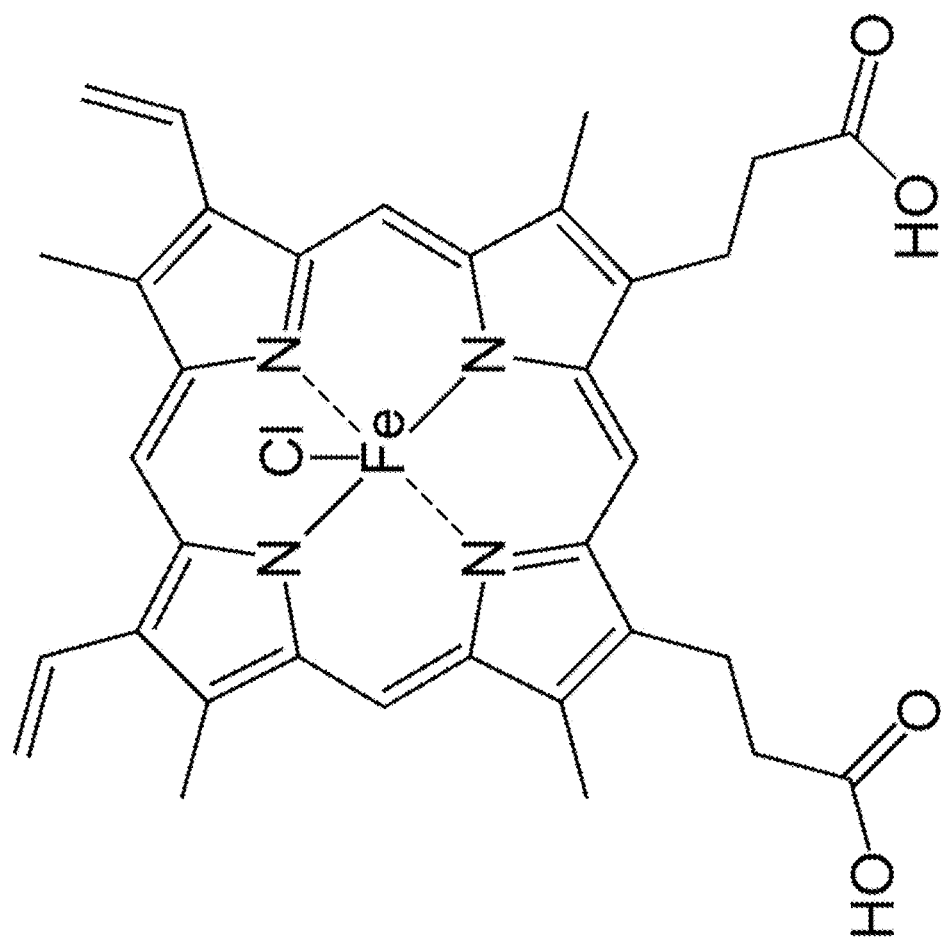
FIG. 3 provides a structure of hemin.

Proteins that bind heme include cytochromes, catalase, myoglobin and hemoglobin among others. Aminolevulinic acid synthase (ALAS) is an enzyme (EC 2.3.1.37) that catalyzes the first step in heme biosynthesis (See FIG. 1 for a diagram of a Heme b biosynthesis pathway), catalyzing the transformation of glycine and succinyl-CoA to aminolevulinic acid. ALAS is translocated to the mitochondria for this step of heme biosynthesis. Aminolevulinic acid is transformed by other enzymes (e.g., ALA dehydratase (ALAD), porphobilinogen deaminase (PBGD), uroporphyrinogen III synthase (UPG3 S), uroporphyrinogen III decarboxylase (UPG3D), coprotoporphyrinogen oxidase (COPROX), protoporphyrinogen IX oxidase (PROTOX), and/or ferrochelatase (FC)) to Heme b (FIG. 2). In some cases, the action of ALAS can be rate-limiting for the heme biosynthesis pathway. Other hemes (e.g., Heme o, Heme a, Heme c) can be made through the action of enzymes on Heme b. Hemin (FIG. 3) is a complex of protoporphyrin IX (e.g., the protoporphyrin of Heme b) with a ferric (+3 oxidation state) iron and a chloride ligand.

As used herein, "intermediate of the heme biosynthesis pathway" refers to one or more of: delta aminolevulinic acid (d-ALA), porphobilinogen, hydroxymethylbilane, uroporphyrinogen III, coproporphyrinogen III, protoporphyrinogen IX, or protoporphyrin IX. In some embodiments, an intermediate of the heme biosynthesis pathway can be selected from the group consisting of delta aminolevulinic acid (d-ALA), porphobilinogen, hydroxymethylbilane, uroporphyrinogen III, coproporphyrinogen III, protoporphyrinogen IX, and protoporphyrin IX. In some embodiments, an intermediate of the heme biosynthesis pathway can be selected from the group consisting of porphobilinogen, hydroxymethylbilane, uroporphyrinogen III, coproporphyrinogen III, protoporphyrinogen IX, or protoporphyrin IX.

Translocation of some ALAS proteins to the mitochondria can be affected by one or more heme regulatory motifs (HRMs; sometimes also called heme responsive motifs)

contained within the ALAS protein. Many HRMs include a C-P motif, and the cysteine is often an axial ligand for heme. In some embodiments, a HRM has a sequence of R/L/N/A/C/S/H/I/G/Q-C-P-L/N/I/F/C-L/M/P/V (SEQ ID NO: 32) (e.g., a HRM can have a sequence of A-C-P-F-V (SEQ ID NO: 33), H-C-P-V-V (SEQ ID NO: 34), I-C-P-F-M (SEQ ID NO: 35), or G-C-P-V-V (SEQ ID NO: 36); see, e.g., FIG. 8). Some organisms have 3 HRMs in their ALAS sequence, while other organisms (e.g., a methylotrophic yeast such as *Pichia pastoris*) have two. In general, a HRM can be called HRM1, HRM2, HRM3, and so forth, depending on where the HRM occurs in the protein sequence, e.g., the first-occurring HRM in the protein sequence (read as N-terminus to C-terminus) would be called HRM1. Mutation of the cysteine (e.g., to serine or alanine) in the HRMs can increase the translocation of ALAS to the mitochondria (see, e.g., González-Domínguez, et al., Yeast. 2001 Jan 15;18(1):41-8. (PubMed ID (PMID) 11124700); Munakata et al., J Biochem. 2004 Aug;136(2):233-8. (PMID 15496594); Dailey et al, Biochem J. 2005 Mar 1;386(Pt 2):381-6. (PMID 15482256)), each of which is herein incorporated by reference in its entirety). Without being bound by any particular theory, it is believed that heme binding to the HRMs of wild type ALAS can inhibit the translocation of ALAS to the mitochondria in a negative feedback manner. Heme is also believed to be involved in the degradation of some ALAS proteins (see, e.g., Kubota, et al., J Biol Chem. 2016 Sep 23;291(39):20516-29. doi: 10.1074/jbc.M116.719161. Epub 2016 Aug 5. (PMID 27496948), incorporated by reference herein in its entirety).

It will be appreciated that a "first HRM" can be an HRM in any part of a protein sequence; a "first HRM" can be, but is not necessarily, the first-occurring HRM (HRM1) in a protein sequence. In some embodiments, a first HRM is HRM1, and a second HRM is HRM2. In some embodiments, a first HRM is HRM1, and a second HRM is HRM3. In some embodiments, a first HRM is HRM2, and a second HRM is HRM1. In some embodiments, a first HRM is HRM2, and a second HRM is HRM3. In some embodiments, a first HRM is HRM3, and a second HRM is HRM1. In some embodiments, a first HRM is HRM3, and a second HRM is HRM2.

In some embodiments, a mutation in a nucleic acid can be an insertion, a deletion, or a substitution. In some embodiments, a mutation in a nucleic acid can be a substitution (e.g., a guanosine to cytosine mutation). In some embodiments, a substitution in a coding sequence (e.g., encoding a protein) can be a silent mutation (e.g., the same amino acid is encoded). In some embodiments, a substitution in a coding sequence can be a nonsynonymous mutation (e.g., a missense mutation or a nonsense mutation). In some embodiments, a substitution in a coding sequence can be a missense mutation (e.g., a different amino acid is encoded). In some embodiments, a substitution in a coding sequence can be nonsense mutation (e.g., a premature stop codon is encoded). In some embodiments, a mutation in a nucleic acid can be can be a deletion. It will be understood that mutations can be used to alter an endogenous nucleic acid, using, for example, CRISPR, TALEN, and/or Zinc-finger nucleases.

In some embodiments, a mutation in a protein sequence can be an insertion, a deletion, or a substitution. It will be understood that a mutation in a nucleic acid that encodes a protein can cause a mutation in a protein sequence. In some embodiments, a mutation in a protein sequence is a substitution (e.g., a cysteine to serine mutation, a cysteine to alanine mutation, a cysteine to valine mutation, a cysteine to leucine mutation, a cysteine to isoleucine mutation, a cysteine to glycine mutation, a cysteine to phenylalanine mutation, a cysteine to threonine mutation, a cysteine to methionine mutation, a cysteine to tryptophan mutation, a cysteine to tyrosine mutation, a cysteine to asparagine mutation, a cysteine to glutamine mutation, a cysteine to proline mutation, a cysteine to arginine mutation, a cysteine to histidine mutation, a cysteine to lysine mutation, a cysteine to aspartic acid mutation, or a cysteine to glutamic acid mutation). In some embodiments, a mutation in a protein sequence can be a deletion.

In some embodiments, an ALAS protein as described herein can include a mutation in at least one HRM; for example, a first HRM, a second HRM, a third HRM, a fourth HRM, a fifth HRM, and so forth.

In some embodiments, an ALAS protein as described herein can include a mutation in at least one HRM (e.g., a first HRM). In some embodiments, an ALAS protein as described herein can include a mutation in a single HRM (e.g., a first HRM or a second HRM). In some embodiments, an ALAS protein as described herein can include a mutation in a cysteine of at least one HRM (e.g., a first HRM). In some embodiments, an ALAS protein as described herein can include a mutation in a cysteine in a single HRM (e.g., a first HRM or a second HRM).

In some embodiments, an ALAS protein as described herein can include a mutation in at least two HRMs (e.g., a first HRM and a second HRM). In some embodiments, an ALAS protein as described herein can include a mutation in each of two HRMs (e.g., a first HRM and a second HRM). In some embodiments, the mutation in the first HRM and the mutation in the second HRM can be the same (e.g., both cysteine to serine or alanine mutations). In some embodiments, the mutation in the first HRM and the mutation in the second HRM can be different (e.g., one is a cysteine to serine mutation and one is a cysteine to alanine mutation). In some embodiments, an ALAS protein as described herein can include a mutation in a cysteine of at least two HRMs (e.g., a first HRM and a second HRM). In some embodiments, an ALAS protein as described herein can include a mutation in a cysteine in each of two HRMs (e.g., a first HRM and a second HRM). In some embodiments, the mutation in the first HRM and the mutation in the second HRM can be the same (e.g., both cysteine to serine or alanine mutations). In some embodiments, the mutation in the first HRM and the mutation in the second HRM can be different (e.g., one is a cysteine to serine mutation and one is a cysteine to alanine mutation).

In some embodiments, an ALAS protein as described herein can include a mutation in at least three HRMs (e.g., a first HRM, a second HRM, and a third HRM). In some embodiments, an ALAS protein as described herein can include a mutation in each of three HRMs (e.g., a first HRM, a second HRM, and a third HRM). In some embodiments, an ALAS protein as described herein can include a mutation in a cysteine at least three HRMs (e.g., a first HRM, a second HRM, and a third HRM). In some embodiments, an ALAS protein as described herein can include a mutation in a cysteine in each of three HRMs (e.g., a first HRM, a second HRM, and a third HRM). In some embodiments, the mutation in each of the first HRM, the second HRM, and the third HRM can be the same (e.g., both cysteine to serine or alanine mutations). In some embodiments, the mutation in one or two of the three HRMs can be different.

In some embodiments, a substitution (a mutation to a different amino acid) can be a substitution for an amino acid (e.g., a cysteine) in a HRM. In some embodiments, a mutation in a first HRM can be a substitution for an amino acid (e.g., a cysteine) in the first HRM. In some embodiments, a mutation in a second HRM can be a substitution for an amino acid (e.g., a cysteine) in the second HRM. In some embodiments, a mutation in a third HRM can be a substitution for an amino acid (e.g., a cysteine) in the third HRM. A substitution can be any appropriate substitution. In some embodiments, a different amino acid can be selected from group consisting of arginine, histidine, lysine, serine, threonine, asparagine, glutamine, selenocysteine, glycine, proline, alanine, isoleucine, leucine, methionine, phenylalanine, tryptophan, tyrosine, and valine. In some embodiments, a different amino acid can be selected from group consisting of arginine, histidine, lysine, serine, threonine, asparagine, glutamine, selenocysteine, glycine, proline, alanine, isoleucine, leucine, methionine, aspartic acid, glutamic acid, phenylalanine, tryptophan, tyrosine, and valine. In some embodiments, a different amino acid is selected from a nonpolar aliphatic amino acid (e.g., glycine, proline, alanine, isoleucine, leucine, methionine, or valine), an aromatic amino acid (e.g., phenylalanine, tryptophan, or tyrosine), a polar uncharged amino acid (e.g., serine, threonine, asparagine, or glutamine), or a positively charged amino acid (arginine, histidine, or lysine). In some embodiments, the different amino acid is serine. In some embodiments, the different amino acid is alanine. In some embodiments, the different amino acid is phenylalanine. In some embodiments, the different amino acid is aspartic acid. In some embodiments, the different amino acid is histidine.

Surprisingly, when an ALAS protein with a cysteine to serine mutation in each of its two HRMs is co-expressed with an exogenous heme-binding protein, the titer of the exogenous heme-binding protein can increase significantly.

Generally, a "titer" is the measurement of the amount of a substance in solution. As used herein, the "titer" of a heme-binding protein refers to the overall amount of the polypeptide, whether or not it is bound to heme, unless otherwise specified. The titer of a protein can be measured by suitable method, such as high-performance liquid chromatography (HPLC or UPLC), liquid chromatography-mass spectrometry (LC-MS), an enzyme-linked immunosorbent assay (ELISA), enzyme activity measurements, iron measurement techniques such as atomic absorption spectroscopy, LC-MS, or ultraviolet and/or visible light spectroscopy.

Mutations in ALAS, such as those described herein, can be used to increase heme production. In some embodiments, the titer of a heme-binding protein can be increased. In some embodiments, the titer of a leghemoglobin (LegH) can be increased. The materials and methods of this disclosure can be useful to increase the production of heme.

The materials and methods described herein can have applications in many industries. For example, heme proteins can be used in food. As another example, heme proteins (e.g., hemoglobins, cytochrome P450s) can be produced for research purposes (e.g., to study drug metabolism). Heme proteins can also be used in industry (e.g., catalases, laccases, and/or peroxidases for uses such as washing detergents, pulp bleaching, lignin degradation). Another potential application for heme proteins is in biocatalysis (e.g. cytochrome P450s, lipoxygenases, and/or laccases can be used for the production of pharmaceutical and commodity chemicals). Some heme proteins can be used as therapeutic agents (e.g., nitric oxide synthases or as part of a blood replacement). In some cases, heme proteins can be used for electronic purposes (e.g. for the production of renewable electricity). As another example, heme therapy can be a treatment option for patients with acute porphyrias, a group of eight genetic diseases that result from inability to produce heme.

Nucleic acid constructs (sometimes also called nucleic acid molecules) are provided herein that allow for genetically engineering a cell (e.g., fungal cell, such as an *Aspergillus* cell, a *Trichoderma* cell, or a yeast cell (e.g., a methylotrophic yeast cell)) to produce a mutant ALAS. In addition, nucleic acid constructs are provided herein that allow for genetically engineering a cell (e.g., fungal cell, such as an *Aspergillus* cell, a *Trichoderma* cell, or a yeast cell (e.g., a methylotrophic yeast cell)) to increase the expression of a heme-binding protein. In some embodiments, nucleic acid constructs are provided herein that allow for genetically engineering a cell (e.g., fungal cell, such as an *Aspergillus* cell, a *Trichoderma* cell, or a yeast cell (e.g., a methylotrophic yeast cell)) to increase the expression of a heme-binding protein from an inducible promoter in the absence of the inducing molecule.

Nucleic acid constructs are provided herein that allow for genetically engineering a cell. A cell can be any appropriate cell. For example, a cell can be a bacterial cell (e.g., an *E. coli* cell, a *B. subtilis* cell, or a *Lactococcus lactis* cell), a fungal cell, an algal cell, a plant cell, an insect cell, or a mammalian cell. In some embodiments, a cell can be a fungal cell. In some embodiments, a cell can be a filamentous fungus cell. In some embodiments, a cell can be an *Aspergillus* or *Trichoderma* cell. In some embodiments, a cell can be a yeast cell. Non-limiting examples of yeast cells include *Pichia* (e.g., *Pichia methanolica, Pichia pastoris*), *Candida* (e.g., *Candida boidinii*) cells, *Hansenula* (e.g., *Hansenula polymorpha*) cells, *Torulopsis* cells, and *Sacharomyces* (e.g., *Sacharomyces cerevisae*) cells. In some embodiments, a cell can be a methylotrophic yeast cell. Non-limiting examples of methylotrophic yeast cells include *Pichia* cells, *Candida* cells, *Hansenula* cells, and *Torulopsis* cells. In some embodiments, a cell can be a *Pichia* cell or a *Sacharomyces* cell. In some embodiments, a cell is a eukaryotic cell. In some embodiments, a cell is a fungal cell. In some embodiments, a cell is a plant cell. In some embodiments, a cell is an algal cell. In some embodiments, a cell is a yeast cell. In some embodiments, a cell is a *Saccharomyces cerevisiae* cell. In some embodiments, a cell is a methylotrophic yeast cell. While the methods are exemplified herein using a *Pichia* species (e.g., *P. pastoris*), other cells can be used, such as other species of the *Pichia* genus or species from any of the *Candida, Hansenula, Pichia,* and *Torulopsis* genera. Non-limiting examples of species of methylotrophic yeast include *Pichia methanolica, Pichia pastoris, Candida boidinii,* and *Hansenula polymorpha*.

Accordingly, in one aspect, this document provides materials and methods for expressing protein. In some embodiments, this document provides a cell (e.g., fungal cell, such as an *Aspergillus* cell, a *Trichoderma* cell, or a yeast cell (e.g., a methylotrophic yeast cell)) including a first nucleic acid construct comprising a nucleotide sequence encoding an ALAS protein. In some embodiments, the first nucleic acid encodes an ALAS protein operably linked to a first promoter element. In some embodiments, an ALAS protein includes at least 1 HRM (e.g., 1, 2, 3, or more HRMs). In some embodiments, an ALAS protein includes at least 2 HRMs (e.g., 2, 3 or more HRMs). In some embodiments, an ALAS protein includes at least 3 HRMs (e.g., 3 or more HRMs). In some embodiments, the ALAS protein includes a mutation in a first HRM (sometimes also called "a first mutation in a first HRM"). In some embodiments, the ALAS protein includes a mutation in a second HRM (sometimes also called "a second mutation in a second HRM"). In some embodiments, the ALAS protein includes a mutation in a first HRM and a mutation in a second HRM. In some embodiments, the first HRM is HRM1. In some embodiments, the second HRM is HRM2. In some embodiments, the ALAS protein includes a mutation in a third HRM (sometimes also called "a third mutation in a third HRM"). In some embodiments, the ALAS protein includes a mutation in a first HRM, a mutation in a second HRM, and a mutation in a third HRM.

In some embodiments, the mutation in the first HRM is a substitution. In some embodiments, the mutation in the first HRM is a cysteine substitution. In some embodiments, the mutation in the first HRM is a cysteine to serine mutation. In some embodiments, the mutation in the first HRM is a cysteine to alanine mutation. In some embodiments, the mutation in the first HRM is a cysteine to phenylalanine mutation. In some embodiments, the mutation in the first HRM is a cysteine to aspartic acid mutation. In some embodiments, the mutation in the first HRM is a cysteine to histidine mutation.

In some embodiments, the mutation in the second HRM is a substitution. In some embodiments, the mutation in the second HRM is a cysteine substitution. In some embodiments, the mutation in the second HRM is a cysteine to serine mutation. In some embodiments, the mutation in the second HRM is a cysteine to alanine mutation. In some embodiments, the mutation in the second HRM is a cysteine to phenylalanine mutation. In some embodiments, the mutation in the second HRM is a cysteine to aspartic acid mutation. In some embodiments, the mutation in the second HRM is a cysteine to histidine mutation.

In some embodiments, the mutation in the third HRM is a substitution. In some embodiments, the mutation in the third HRM is a cysteine substitution. In some embodiments, the mutation in the third HRM is a cysteine to serine mutation. In some embodiments, the mutation in the third HRM is a cysteine to alanine mutation. In some embodiments, the mutation in the third HRM is a cysteine to phenylalanine mutation. In some embodiments, the mutation in the third HRM is a cysteine to aspartic acid mutation. In some embodiments, the mutation in the third HRM is a cysteine to histidine mutation.

In some embodiments, the mutation in the first HRM corresponds to a mutation in residue 12 in SEQ ID NO: 29. In some embodiments, the mutation in the second HRM corresponds to a mutation in residue 39 in SEQ ID NO: 29. In some embodiments, the mutation in the first HRM is a cysteine to serine mutation corresponding to a cysteine to serine mutation in residue 12 in SEQ ID NO: 29. In some embodiments, the mutation in the first HRM is a cysteine to alanine mutation corresponding to a cysteine to alanine mutation in residue 12 in SEQ ID NO: 29. In some embodiments, the mutation in the first HRM is a cysteine to phenylalanine mutation corresponding to a cysteine to phenylalanine mutation in residue 12 in SEQ ID NO: 29. In some embodiments, the mutation in the first HRM is a cysteine to histidine mutation corresponding to a cysteine to histidine mutation in residue 12 in SEQ ID NO: 29. In some embodiments, the mutation in the second HRM is a cysteine to serine mutation corresponding to a cysteine to serine mutation in residue 39 in SEQ ID NO: 29. In some embodiments, the mutation in the second HRM is a cysteine to alanine mutation corresponding to a cysteine to alanine mutation in residue 39 in SEQ ID NO: 29. In some embodiments, the mutation in the second HRM is a cysteine to phenylalanine mutation corresponding to a cysteine to phenylalanine mutation in residue 39 in SEQ ID NO: 29. In some embodiments, the mutation in the second HRM is a cysteine to histidine mutation corresponding to a cysteine to histidine mutation in residue 39 in SEQ ID NO: 29.

In some embodiments, the first nucleic acid includes a mutation corresponding to a guanosine to cytosine mutation at nucleotide position 35 in SEQ ID NO: 28. In some embodiments, the first nucleic acid includes a mutation corresponding to a thymine to guanosine mutation at nucleotide position 34 in SEQ ID NO: 28 and a guanosine to cytosine mutation at nucleotide position 35 in SEQ ID NO: 28. In some embodiments, the first nucleic acid includes a mutation corresponding to a guanosine to cytosine mutation at nucleotide position 116 in SEQ ID NO: 28. In some embodiments, the first nucleic acid includes a mutation corresponding to a thymine to guanosine mutation in nucleotide position 115 in SEQ ID NO: 28 and a guanosine to cytosine mutation at nucleotide position 116 in SEQ ID NO: 28. It will be appreciated that cysteine to serine mutations can be accomplished by mutations at nucleotides other than those specifically disclosed herein. It will be appreciated that cysteine to alanine mutations can be accomplished by mutations at nucleotides other than those specifically disclosed herein. In some embodiments, the first nucleic acid construct includes SEQ ID NO: 30. In some embodiments, the ALAS protein has the sequence of SEQ ID NO: 31. (See, e.g., FIG. 7).

As used herein, "operably linked" means that a promoter or other expression element(s) are positioned relative to a nucleic acid coding sequence in such a way as to direct or regulate expression of the coding sequence (e.g., in-frame).

A "corresponding" amino acid position (or substitution) in a protein sequence different from a reference protein sequence (e.g., in the ALAS protein sequence of a different organism compared to a reference ALAS protein sequence, such as SEQ ID NO: 29) can be identified by performing a sequence alignment between the protein sequences of interest. It will be understood that in some cases, a gap exists in a protein alignment. Similarly, a "corresponding" nucleic acid position (or substitution) in a nucleic acid sequence different from a reference nucleic acid sequence (e.g., in the ALAS nucleic acid sequence of a different organism compared to a reference ALAS nucleic acid sequence, such as SEQ ID NO: 28) can be identified by performing a sequence alignment between the nucleic acid sequences of interest. It will be understood that in some cases, a gap exists in a nucleic acid alignment. As used herein, a nucleotide or amino acid position "relative to" a reference sequence can be the corresponding nucleotide or amino acid position in a reference sequence.

Nucleic acid molecules used in the methods described herein are typically DNA, but RNA molecules can be used under the appropriate circumstances. As used herein, "exogenous" refers to any nucleic acid sequence that is introduced into a cell from, for example, the same or a different organism or a nucleic acid generated synthetically (e.g., a codon-optimized nucleic acid sequence). For example, an exogenous nucleic acid can be a nucleic acid from one microorganism (e.g., one genus or species of methylotrophic yeast) that is introduced into a different genus or species of methylotrophic yeast; however, an exogenous nucleic acid also can be a nucleic acid from a methylotrophic yeast that is introduced recombinantly into a methylotrophic yeast as an additional copy despite the presence of a corresponding native nucleic acid sequence, or a nucleic acid from a methylotrophic yeast that is introduced recombinantly into a methylotrophic yeast containing one or more mutations, insertions, or deletions compared to the sequence native to the methylotrophic yeast. For example, *P. pastoris* contains an endogenous nucleic acid encoding an ALAS; an additional copy of the *P. pastoris* ALAS nucleic acid (e.g., introduced recombinantly into *P. pastoris*) is considered to be exogenous. Similarly, an "exogenous" protein is a protein encoded by an exogenous nucleic acid.

In some instances, an exogenous nucleic acid can be a heterologous nucleic acid. As used herein, a "heterologous" nucleic acid refers to any nucleic acid sequence that is not native to an organism (e.g., a heterologous nucleic acid can be a nucleic acid from one microorganism (e.g., one genus or species of methylotrophic yeast, whether or not it has been codon-optimized) that is introduced into a different genus or species of methylotrophic yeast)). Similarly, a "heterologous" protein is a protein encoded by a heterologous nucleic acid.

A nucleic acid molecule is considered to be exogenous to a host organism when any portion thereof (e.g., a promoter sequence or a sequence of an encoded protein) is exogenous to the host organism. A nucleic acid molecule is considered to be heterologous to a host organism when any portion thereof (e.g., a promoter sequence or a sequence of an encoded protein) is heterologous to the host organism.

In some embodiments, this document provides a cell (e.g., fungal cell, such as an *Aspergillus* cell, a *Trichoderma* cell, or a yeast cell (e.g., a methylotrophic yeast cell)) comprising a first nucleic acid construct as disclosed herein and a second nucleic acid construct comprising a nucleotide sequence encoding a heme-binding protein. In some embodiments, the second nucleic acid encodes a heme-binding protein operably linked to the first promoter element. In some embodiments, the second nucleic acid encodes a heme-binding protein operably linked to a second promoter element. In some embodiments, a heme-binding protein can be an exogenous heme-binding protein. In some embodiments, a heme-binding protein can be a heterologous heme-binding protein. In some embodiments, a heme-binding protein can be selected from the group consisting of a globin (PF00042 in the Pfam database), a cytochrome (e.g., a cytochrome P450, a cytochrome a, a cytochrome b, a cytochrome c), a cytochrome c oxidase, a ligninase, a catalase, and a peroxidase. In some embodiments, a globin can be selected from the group consisting of an androglobin, a chlorocruorin, a cytoglobin, an erythrocruorin, a flavohemoglobin, a globin E, a globin X, a globin Y, a hemoglobin (e.g., a beta hemoglobin, an alpha hemoglobin), a histoglobin, a leghemoglobin, a myoglobin, a neuroglobin, a non-symbiotic hemoglobin, a protoglobin, and a truncated hemoglobin (e.g., a HbN, a HbO, a Glb3, a cyanoglobin). In some embodiments, the heme-binding protein can be a non-symbiotic hemoglobin. In some embodiments, the heme-binding protein can be a leghemoglobin. In some embodiments, the heme-binding protein can be soybean leghemoglobin (LegH). A reference amino acid sequence for LegH is provided in FIG. 4 as SEQ ID NO: 4. LegH is a protein that binds to heme, which results in a characteristic absorption at 415 nm and a distinct red color. The LegH protein (also known as LGB2) is naturally found in root nodules of soybean (see, for example, UniprotKB Accession No. P02236). See, also, WO 2014/110539 and WO 2014/110532, each of which is herein incorporated by reference in its entirety. In some embodiments, a heme-binding protein can have an amino acid sequence that is at least 70% (e.g., at least 75%, 80%, 85%, 90%, 91%, 92%, 93%, 94%, 95%, 96%, 97%, 98%, or 99%) identical to the amino acid sequence set forth in any of SEQ ID NOs: 1-27 (FIG. 4). In some embodiments, a heme-binding protein can have an amino acid sequence set forth in any of SEQ ID NOs: 1-27. In some embodiments, a heme-binding protein uses heme as a cofactor. As used herein, a "cofactor" is a molecule or ion that is directly involved in enzyme catalysis. In some embodiments, a heme-binding protein may or may not be an enzyme. In some embodiments, the heme-binding protein may or may not be part of the heme biosynthesis pathway. In some embodiments, the heme-binding protein may or may not be an ALAS. In some embodiments, the heme-binding protein may or may not be a ferrochelatase. In some embodiments, the heme-binding protein may or may not be a coprotoporphyrinogen oxidase. In some embodiments, the heme binding protein may or may not be ALAD, PBGD, UPG3S, UPG3D, COPROX, PROTOX, or FC. In some embodiments, a heme-binding protein has an amino acid sequence that is at least 70% (e.g., at least 75%, 80%, 85%, 90%, or 95%) identical to an amino acid sequence in any of SEQ ID NOs: 1-27. In some embodiments, a heme-binding protein is a bacteria-derived heme-binding protein, a yeast-derived heme-binding protein, an algae-derived heme-binding protein, a fungus-derived heme-binding protein, or a plant-derived heme-binding protein.

As used herein, a "bacteria-derived protein", "yeast-derived protein", "algae-derived protein", "fungus-derived protein", or "plant-derived protein" refers to the immediate source of the protein, and can mean any protein that is produced in a bacterium, a yeast, an algae, a fungus, or a plant, respectively, independently of whether the protein is natively expressed in the bacterium, yeast, algae, fungus, or plant, respectively.

Provided herein are methods of producing an ALAS protein. Also provided herein are methods of producing an ALAS protein using any of the cells (e.g., fungal cells, such as *Aspergillus* cells, *Trichoderma* cells, or yeast cells (e.g., methylotrophic yeast cells)) described herein. Also provided herein are methods of producing an ALAS protein using any of the nucleic acid constructs described herein. In some embodiments, provided herein are methods comprising expressing a first nucleic acid construct comprising a nucleotide sequence encoding an ALAS protein comprising a mutation in a first HRM. In some embodiments, the titer of an ALAS protein can be increased by at least 5% (e.g., at least 6%, 7%, 8%, 9%, 10%, 15%, 20%, 25%, 30%, 40%, 50%, 60%, 70%, 80%, 90%, 100%, 120%, 140%, 150%, 160%, 180%, 200%, 220%, 240%, 250%, or more) compared to a corresponding method lacking a nucleic acid construct comprising a nucleotide sequence encoding an ALAS protein comprising a mutation in a first HRM. In some embodiments, the titer of an ALAS protein can be increased by at least 5% (e.g., at least 6%, 7%, 8%, 9%, 10%, 15%, 20%, 25%, 30%, 40%, 50%, 60%, 70%, 80%, 90%, 100%, 120%, 140%, 150%, 160%, 180%, 200%, 220%, 240%, 250%, or more) compared to a corresponding method expressing a nucleic acid encoding an ALAS protein that does not comprise a mutation in a first HRM. In some embodiments, provided herein are methods comprising expressing a first nucleic acid construct comprising a nucleotide sequence encoding an ALAS protein comprising a mutation in a first HRM and a mutation in a second HRM. In some embodiments, the titer of an ALAS protein can be increased by at least 5% (e.g., at least 6%, 7%, 8%, 9%, 10%, 15%, 20%, 25%, 30%, 40%, 50%, 60%, 70%, 80%, 90%, 100%, 120%, 140%, 150%, 160%, 180%, 200%, 220%, 240%, 250%, or more) compared to a corresponding method lacking a nucleic acid construct comprising a nucleotide sequence encoding an ALAS protein comprising a mutation in a first HRM and a mutation in a second HRM. In some embodiments, the titer of an ALAS protein can be increased by at least 5% (e.g., at least 6%, 7%, 8%, 9%, 10%, 15%, 20%, 25%, 30%, 40%, 50%, 60%, 70%, 80%, 90%, 100%, 120%, 140%, 150%, 160%, 180%, 200%, 220%, 240%, 250%, or more) compared to a corresponding method expressing a nucleic acid encoding an ALAS protein that does not comprise a mutation in a first HRM and a mutation in a second HRM.

Provided herein are methods of producing a tetrapyrrole or a derivative thereof. Also provided herein are methods of producing a tetrapyrrole or a derivative thereof using any of the cells (e.g., fungal cells, such as *Aspergillus* cells, *Trichoderma* cells, or yeast cells (e.g., methylotrophic yeast cells)) described herein. Also provided herein are methods of producing a tetrapyrrole or a derivative thereof using any of the nucleic acid constructs described herein. In some embodiments, provided herein are methods of producing a tetrapyrrole or a derivative thereof comprising expressing a first nucleic acid construct comprising a nucleotide sequence encoding an ALAS protein comprising a mutation in a first HRM. In some embodiments, the titer of a tetrapyrrole or a derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method lacking a nucleic acid construct comprising a nucleotide sequence encoding an ALAS protein comprising a mutation in a first HRM. In some embodiments, the titer of a tetrapyrrole or a derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method expressing a nucleic acid encoding an ALAS protein that does not comprise a mutation in a first HRM. In some embodiments, provided herein are methods of producing a tetrapyrrole or a derivative thereof comprising expressing a first nucleic acid construct comprising a nucleotide sequence encoding an ALAS protein comprising a mutation in a first HRM and a second mutation in a second HRM. In some embodiments, the titer of a tetrapyrrole or a derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method lacking a nucleic acid construct comprising a nucleotide sequence encoding an ALAS protein comprising a mutation in a first HRM and a mutation in a second HRM. In some embodiments, the titer of a tetrapyrrole or a derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method expressing a nucleic acid encoding an ALAS protein that does not comprise a mutation in a first HRM and a mutation in a second HRM. In some embodiments, a tetrapyrrole or a derivative thereof is a chlorin (e.g., a chlorophyll) or a derivative thereof. In some embodiments, a tetrapyrrole or a derivative thereof is a precorrin, a co-precorrin, a corrin (e.g., vitamin B12), or a derivative thereof. In some embodiments, a tetrapyrrole or a derivative thereof is a porphyrin or a derivative thereof. In some embodiments, a tetrapyrrole or a derivative thereof is a heme or a derivative thereof. In some embodiments, a tetrapyrrole or a derivative thereof is heme B. In some embodiments, a tetrapyrrole or a derivative thereof is a metabolic product of heme (e.g., bilirubin or a derivative thereof).

Provided herein are methods of producing an intermediate of the heme biosynthesis pathway, a heme (e.g., heme B, heme o, heme a, heme c), a corrin (e.g., Vitamin B12), a chlorophyll, or a derivative thereof. Also provided herein are methods of producing an intermediate of the heme biosynthesis pathway, a heme, a corrin, a chlorophyll, or a derivative thereof using any of the cells (e.g., fungal cells, such as *Aspergillus* cells, *Trichoderma* cells, or yeast cells (e.g., methylotrophic yeast cells))described herein. Also provided herein are methods of producing an intermediate of the heme biosynthesis pathway, a heme, a corrin, a chlorophyll, or a derivative thereof using any of the nucleic acid constructs described herein. In some embodiments, provided herein are methods of producing an intermediate of the heme biosynthesis pathway, a heme, a corrin, a chlorophyll, or a derivative thereof comprising expressing a first nucleic acid construct comprising a nucleotide sequence encoding an ALAS protein comprising a mutation in a first HRM. In some embodiments, the titer of an intermediate of the heme biosynthesis pathway, a heme, a corrin, a chlorophyll, or a derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method lacking a nucleic acid construct comprising a nucleotide sequence encoding an ALAS protein comprising a mutation in a first HRM. In some embodiments, the titer of an intermediate of the heme biosynthesis pathway, a heme, a corrin, a chlorophyll, or a derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method expressing a nucleic acid encoding an ALAS protein that does not comprise a mutation in a first HRM. In some embodiments, provided herein are methods of producing an intermediate of the heme biosynthesis pathway, a heme, a corrin, a chlorophyll, or a derivative thereof comprising expressing a first nucleic acid construct comprising a nucleotide sequence encoding an ALAS protein comprising a mutation in a first HRM and a mutation in a second HRM. In some embodiments, the titer of an intermediate of the heme biosynthesis pathway, a heme, a corrin, a chlorophyll, or a derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method lacking a nucleic acid construct comprising a nucleotide sequence encoding an ALAS protein comprising a mutation in a first HRM and a mutation in a second HRM. In some embodiments, the titer of an intermediate of the heme biosynthesis pathway, a heme, a corrin, a chlorophyll, or a derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method expressing a nucleic acid encoding an ALAS protein that does not comprise a mutation in a first HRM and a mutation in a second HRM. In some embodiments, an intermediate of the heme biosynthesis pathway, a heme, or a derivative thereof is a heme. In some embodiments, an intermediate of the heme biosynthesis pathway, a heme, or a derivative thereof is heme B.

Provided herein are methods of producing a heme (e.g., heme B, heme o, heme a, heme c) or a derivative thereof Also provided herein are methods of producing a heme or derivative thereof using any of the cells (e.g., fungal cells, such as *Aspergillus* cells, *Trichoderma* cells, or yeast cells (e.g., methylotrophic yeast cells)) described herein. Also provided herein are methods of producing a heme or derivative thereof using any of the nucleic acid constructs described herein. In some embodiments, provided herein are methods of producing a heme or derivative thereof comprising expressing a first nucleic acid construct comprising a nucleotide sequence encoding an ALAS protein comprising a mutation in a first HRM. In some embodiments, the titer of a heme or derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method lacking a nucleic acid construct comprising a nucleotide sequence encoding an ALAS protein comprising a mutation in a first HRM. In some embodiments, the titer of a heme or derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method expressing a nucleic acid encoding an ALAS protein that does not comprise a mutation in a first HRM. In some embodiments, provided herein are methods of producing a heme or derivative thereof comprising expressing a first nucleic acid construct comprising a nucleotide sequence encoding an ALAS protein comprising a mutation in a first HRM and a mutation in a second HRM. In some embodiments, the titer of a heme or derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method lacking a nucleic acid construct comprising a nucleotide sequence encoding an ALAS protein comprising a mutation in a first HRM and a mutation in a second HRM. In some embodiments, the titer of a heme or derivative thereof can be increased by at least 5% (e.g., at least 10%, 20%, 30%, 40%, 50%, 60%, 70%, 80%, 90%, 100%, 120%, 140%, 150%, 160%, 180%, 200%, 220%, 240%, 250%, 280%, 300%, 320%, 340%, 350%, or more) compared to a corresponding method expressing a nucleic acid encoding an ALAS protein that does not comprise a mutation in a first HRM and a mutation in a second HRM. In some embodiments, a heme or a derivative thereof is heme B.

Provided herein are methods of producing a heme-binding protein. Also provided herein are methods of producing a heme-binding protein using any of the cells (e.g., fungal cells, such as *Aspergillus* cells, *Trichoderma* cells, or yeast cells (e.g., methylotrophic yeast cells))described herein. Also provided herein are methods of producing a heme-binding protein using any of the nucleic acid constructs described herein. In some embodiments, provided herein are methods comprising expressing a first nucleic acid construct comprising a nucleotide sequence encoding an ALAS protein comprising a mutation in a first HRM and expressing a second nucleic acid construct comprising a nucleotide sequence encoding a heme-binding protein. In some embodiments, provided herein are methods comprising expressing a first nucleic acid construct comprising a nucleotide sequence encoding an ALAS protein comprising a mutation in a first HRM and a mutation in a second HRM and expressing a second nucleic acid construct comprising a nucleotide sequence encoding a heme-binding protein. In some embodiments, provided herein are methods comprising expressing a first nucleic acid construct comprising a nucleotide sequence encoding an ALAS protein comprising a mutation in a first HRM and a mutation in a second HRM and expressing a second nucleic acid construct comprising a nucleotide sequence encoding a heme-binding protein. In some embodiments of any of the methods described herein, the methods allow for an increase in the titer of a heme-binding protein. In some embodiments, the titer of a heme-binding protein can be increased by at least 5% (e.g., at least 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or more) compared to a corresponding method lacking a nucleic acid construct comprising a nucleotide sequence encoding an ALAS protein comprising a mutation in a first HRM. In some embodiments, the titer of a heme-binding protein can be increased by at least 5% (e.g., at least 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or more) compared to a corresponding method expressing a nucleic acid encoding an ALAS protein that does not comprise a mutation in a first HRM. In some embodiments, the titer of a heme-binding protein can be increased by at least 5% (e.g., at least 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or more) compared to a corresponding method lacking a nucleic acid construct comprising a nucleotide sequence encoding an ALAS protein comprising a mutation in a first HRM and a mutation in a second HRM. In some embodiments, the titer of a heme-binding protein can be increased by at least 5% (e.g., at least 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or more) compared to a corresponding method expressing a nucleic acid encoding an ALAS protein that does not comprise a mutation in a first HRM and a mutation in a second HRM.

Provided herein are methods of producing a tetrapyrrole-binding protein. Also provided herein are methods of producing a tetrapyrrole-binding protein using any of the cells (e.g., fungal cells, such as *Aspergillus* cells, *Trichoderma* cells, or yeast cells (e.g., methylotrophic yeast cells)) described herein. Also provided herein are methods of producing a tetrapyrrole-binding protein using any of the nucleic acid constructs described herein. In some embodiments, provided herein are methods comprising expressing a first nucleic acid construct comprising a nucleotide sequence encoding an ALAS protein comprising a mutation in a first HRM and expressing a second nucleic acid construct comprising a nucleotide sequence encoding a tetrapyrrole-binding protein. In some embodiments, provided herein are methods comprising expressing a first nucleic acid construct comprising a nucleotide sequence encoding an ALAS protein comprising a mutation in a first HRM and expressing a second nucleic acid construct comprising a nucleotide sequence encoding a tetrapyrrole-binding protein. In some embodiments, provided herein are methods comprising expressing a first nucleic acid construct comprising a nucleotide sequence encoding an ALAS protein comprising a mutation in a first HRM and a mutation in a second HRM and expressing a second nucleic acid construct comprising a nucleotide sequence encoding a tetrapyrrole-binding protein. In some embodiments, provided herein are methods comprising expressing a first nucleic acid construct comprising a nucleotide sequence encoding an ALAS protein comprising a mutation in a first HRM and a mutation in a second HRM and expressing a second nucleic acid construct comprising a nucleotide sequence encoding a tetrapyrrole-binding protein. In some embodiments of any of the methods described herein, the methods allow for an increase in the titer of a tetrapyrrole-binding protein. In some embodiments, the titer of a tetrapyrrole-binding protein can be increased by at least 5% (e.g., at least 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or more) compared to a corresponding method lacking a nucleic acid construct comprising a nucleotide sequence encoding an ALAS protein comprising a mutation in a first HRM. In some embodiments, the titer of a tetrapyrrole-binding protein can be increased by at least 5% (e.g., at least 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or more) compared to a corresponding method expressing a nucleic acid encoding an ALAS protein that does not comprise a mutation in a first HRM. In some embodiments, the titer of a tetrapyrrole-binding protein can be increased by at least 5% (e.g., at least 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or more) compared to a corresponding method lacking a nucleic acid construct comprising a nucleotide sequence encoding an ALAS protein comprising a mutation in a first HRM and a mutation in a second HRM. In some embodiments, the titer of a tetrapyrrole-binding protein can be increased by at least 5% (e.g., at least 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, or more) compared to a corresponding method expressing a nucleic acid encoding an ALAS protein that does not comprise a mutation in a first HRM and a mutation in a second HRM. In some embodiments, a tetrapyrrole is a chlorin (e.g., a chlorophyll) or a derivative thereof. In some embodiments, a tetrapyrrole is a precorrin, a co-precorrin, a corrin (e.g., vitamin B12), or a derivative thereof. In some embodiments, a tetrapyrrole is a porphyrin or a derivative thereof. In some embodiments, a tetrapyrrole is a heme or a derivative thereof. In some embodiments, a tetrapyrrole is heme B. In some embodiments, a tetrapyrrole is a metabolic product of heme (e.g., bilirubin or a derivative thereof).

As used herein, a "corresponding method" is a method that is essentially identical to a reference method in all ways except for the identified difference. For example, a corresponding method expressing a nucleic acid encoding an ALAS protein that does not comprise a mutation in a first HRM and a mutation in a second HRM would be the same in all aspects (e.g., genetic makeup of cell, temperature and time of culture, and so forth), except that the corresponding method would express a nucleic acid encoding an ALAS protein that does not comprise a mutation in a first HRM and a mutation in a second HRM.

Genetically engineering a cell (e.g., fungal cell, such as an *Aspergillus* cell, a *Trichoderma* cell, or a yeast cell (e.g., a methylotrophic yeast cell)) typically includes introducing a recombinant nucleic acid molecule (also called a nucleic acid construct) into the cell. As described herein, a recombinant nucleic acid molecule typically includes an exogenous nucleic acid that encodes a protein (e.g., a protein involved in heme biosynthesis, a heme-binding protein, or a transcription factor) operably linked to at least one promoter element (e.g., an inducible or constitutive promoter element). In some embodiments, a recombinant nucleic acid molecule can include a linear sequence of two or more protein-coding sequences operably linked to the same or separate promoter elements (e.g., a first promoter operably linked to a first nucleic acid encoding a first protein and a second promoter operably linked to a second nucleic acid encoding a second protein, or a promoter operably linked to a first nucleic acid encoding a first protein and a second nucleic acid encoding a second protein). In some cases, a recombinant nucleic acid molecule including at least one promoter operably linked to a nucleotide sequence encoding a protein can be called a cassette.

A recombinant nucleic acid can include expression elements. Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins.

Nucleic acids can be detected using any number of amplification techniques (see, e.g., *PCR Primer: A Laboratory Manual*, 1995, Dieffenbach & Dveksler, Eds., Cold Spring Harbor Laboratory Press, Cold Spring Harbor, NY; and U.S. Pat. Nos. 4,683,195; 4,683,202; 4,800,159; and 4,965,188) with an appropriate pair of oligonucleotides (e.g., primers). A number of modifications to the original PCR method have been developed and can be used to detect selected nucleic acids.

Methanol utilization is typically initiated by the conversion of methanol to formaldehyde by the action of alcohol oxidase. *Pichia pastoris* contains two genes for alcohol oxidases, AOX1 and AOX2. Strains with reduced alcohol oxidase activity ("methanol utilization slow" or MutS strains) can produce more of a recombinant protein expressed from the AOX1 promoter than strains that do not have reduced alcohol oxidase activity. Strains mutated in both AOX genes and completely lacking alcohol oxidase activity cannot metabolize methanol, but can still be induced for expression from the AOX1 promoter by methanol. These strains retain the ability to use other carbon sources for growth, but still express heterologous proteins from the AOX1 promoter upon the addition of methanol. Because these strains do not metabolize methanol ("methanol utilization minus" or Mut-strains), much less methanol is required for induction of protein expression, and strains carrying these mutations avoid issues related to methanol feeding in large-scale fermentations. See, for example, Chiruvolu et al., 1997, Enzyme Microb. Technol., 21:277-83.

Suitable transcription factors, and nucleic acids encoding transcription factors (e.g., exogenous nucleic acids encoding transcription factors), include, for example, Mxr1 from a *P. pastoris*. A representative *K. pastoris* Mxr1 nucleic acid sequence can be found, for example, in GenBank Accession No. DQ395124, while a representative *K. pastoris* Mxr1 protein sequence can be found, for example, in GenBank Accession No. ABD57365. In some embodiments, the transcription factor is a Mit1 sequence from *K. phaffii* (see, for example, UniParc Accession No. UPI0001A4D18B). Suitable transcription factors also can be found in *Hansenula polymorpha* (e.g., the Adr1 sequence; see, for example, GenBank Accession No. AEOI02000005, bases 858873 to 862352, for the nucleic acid sequence and GenBank Accession No. ESX01253 for the amino acid sequence) and *Candida boidinii* (e.g., the Trm1 sequence; see, for example, GenBank Accession No. AB365355 for the nucleic acid sequence and GenBank Accession No. BAF99700 for the amino acid sequence; and Trm2 sequence; see, for example, GenBank Accession No. AB548760 for the nucleic acid sequence and GenBank Accession No. BAJ07608 for the amino acid sequence).

Transcription factors such as Mxr1 may be normally expressed at low levels. In some embodiments, it is desirable to place an exogenous nucleic acid (e.g., a transcription factor) under control of a promoter that is inducible.

Methanol-regulated transcription factors in *Pichia* can bind to an AOX1 promoter and act cooperatively with Mxr1 to activate transcription from an AOX1 promoter. In some embodiments, two methanol-regulated transcription factors (e.g., Mxr1 and Mit1) can be operably linked to a methanol inducible promoter element.

There are a number of inducible promoters that can be used when genetically engineering cells (e.g., fungal cells such as *Aspergillus, Trichoderma* cells, or yeast cells (e.g., methylotrophic yeast cells)). Suitable methanol inducible promoters include pAOX1, (e.g., a pAOX1 such as the promoter for *K. pastoris* AOX1 (see, for example, the promoter for GenBank Accession No. U96967.1) or a promoter described in U.S. Provisional Patent Application No. 62/835,338, filed Apr. 17, 2019, incorporated herein by reference in its entirety), as well as other methanol-inducible promoters, or promoter elements therefrom. These include, without limitation, a pAOX2 promoter (e.g., from *K. phaffii* or *K. pastoris* (see, for example, GenBank Accession No. X79871.1)), an alcohol oxidase (AOD1) promoter from, e.g., *Candida boidinii* (see, for example, GenBank Accession No. E06147.1), the alcohol oxidase (MOX) promoter from *Hansenula polymorpha* (see, for example, GenBank Accession No. AJ313360.1), the MOD1 or MOD2 promoter from *Pichia methanolica* (see, for example, Raymond et al., 1998, Yeast, 14:11-23; and Nakagawa et al., 1999, Yeast, 15:1223-30), the DHAS promoter from *P. pastoris* (see, for example, the promoter for GenBank Accession No. FJ752551) or a promoter element therefrom, the formaldehyde dehydrogenase (FLD1) promoter from *K. pastoris* (see, for example, GenBank Accession No. KJ755994.1), or the PEX8 promoter from *P. pastoris* (see, for example, Kranthi et al., 2010, Yeast, 27:705-11). Typically, these promoters can be induced by methanol. Suitable constitutive promoters and constitutive promoter elements include, without limitation, the *P. pastoris* promoter (or a portion thereof) from the transcriptional elongation factor EF-1α gene (TEF1), which is strongly transcribed in a constitutive manner. Other suitable constitutive promoters (or promoter elements therefrom) also can be used, including, without limitation, the glyceraldehyde-3-phosphate dehydrogenase (GAPDH) promoter from *K. pastoris* (see, for example, the promoter for GenBank Accession No. U62648.1), the promoter from the potential glycosyl phosphatidyl inositol (GPI)-anchored protein, GCW14p (PAS_chr1-4_0586) from *K. phaffii* (see, for example, the promoter for GenBank Accession No. XM_002490678), and the promoter from the 3-phosphoglycerate kinase gene (PGK1) from *K. pastoris* (see, for example, GenBank Accession No. AY288296). It will be appreciated that a choice of promoter may be influenced by the expression system. For example, for expression in *K. phaffii*, a *K. phaffii* promoter might be chosen, while for expression in *C. boidinii*, a *C. boidinii* promoter might be chosen. However, in some cases, a promoter from one organism (e.g., *K. phaffii*) may be appropriate to be used in another organism (e.g., *C. boidinii* or *K. pastoris*). Further, it is noted that a combination of inducible (e.g., methanol-inducible) and constitutive promoters (or promoter elements therefrom) can be combined to further increase the expression of any of the nucleic acids operably linked thereto.

Any of the encoded proteins as described herein can be operably linked to an inducible promoter element (e.g., a methanol-inducible promoter element) or a constitutive promoter element. Inducible promoters and elements therefrom are discussed above. Constitutive promoters and constitutive promoter elements are known in the art. For example, a commonly used constitutive promoter from *P. pastoris* is the promoter, or a portion thereof, from the transcriptional elongation factor EF-1α gene (TEF1), which is strongly transcribed in a constitutive manner. Other constitutive promoters, or promoter elements therefrom, however, can be used, including, without limitation, the glyceraldehyde-3-phosphate dehydrogenase (GAPDH) promoter from *K. pastoris* (see, for example, the promoter for GenBank Accession No. U62648.1), the promoter from the potential glycosyl phosphatidyl inositol (GPI)-anchored protein, GCW14p (PAS_chr1-4_0586), from *K. phaffii* (see, for example, the promoter for GenBank Accession No. XM_002490678), or the promoter from the 3-phosphoglycerate kinase gene (PGK1) from *K. pastoris* (see, for example, the promoter for GenBank Accession No. AY288296).

In some embodiments, any of the cells (e.g., fungal cell, such as an *Aspergillus* cell, a *Trichoderma* cell, or a yeast cell (e.g., a methylotrophic yeast cell)) herein can further include a third nucleic acid construct comprising a nucleotide sequence encoding a third protein operably linked to the first promoter element, the second promoter element, or a third promoter element. In some embodiments, any of the cells (e.g., fungal cell, such as an *Aspergillus* cell, a *Trichoderma* cell, or a yeast cell (e.g., a methylotrophic yeast cell)) herein can further include a fourth nucleic acid construct comprising a nucleotide sequence encoding a fourth protein operably linked to the first promoter element, the second promoter element, the third promoter element, or a fourth promoter element. In some embodiments, the third protein can be a transcription factor. In some embodiments, the fourth protein can be a transcription factor. In some embodiments, any of the promoter elements herein (e.g., a first promoter element, a second promoter element, a third promoter element, or a fourth promoter element) can contain one or more recognition sequences for a transcription factor. Therefore, in some embodiments, a feedback loop may be constructed such that the transcription factor drives the expression of additional copies of the transcription factor, as well as the expression of one or more of an ALAS and a heme-binding protein. In some embodiments, a transcription factor can be Mxr1 (see, e.g., U.S. Pat. No. 9,938,327, which is incorporated by reference in its entirety). In some embodiments, a third protein can be a protein involved in heme biosynthesis. In some embodiments, a fourth protein can be a protein involved in heme biosynthesis. In some embodiments, a protein involved in heme biosynthesis can be selected from the group consisting of δ-aminolevulinic acid dehydratase (ALAD), porphobilinogen deaminase (PBGD), uroporphyrinogen III synthase (UPG3S), uroporphyrinogen III decarboxylase (UPG3D), coprotoporphyrinogen oxidase (COPROX), protoporphyrinogen IX oxidase (PROTOX), and/or ferrochelatase (FC). In some embodiments, a protein involved in heme biosynthesis can be selected from the group consisting of δ-aminolevulinic acid dehydratase (ALAD), porphobilinogen deaminase (PBGD), uroporphyrinogen III synthase (UPG3 S), uroporphyrinogen III decarboxylase (UPG3D), coproporphyrinogen oxidase (COPROX), and/or protoporphyrinogen IX oxidase (PROTOX).

Previous studies in *Saccharomyces cerevisiae* identified ALA dehydratase and porphobilinogen deaminase as rate limiting enzymes in heme biosynthesis (see, for example, Hoffman et al., 2003, Biochem. Biophys. Res. Commun., 310(4):1247-53). However, heterologous expression of individual heme enzymes in *P. pastoris* from the glyceraldehyde-3-phosphate dehydrogenase (GAP) promoter failed to overcome limitations associated with the expression of a recombinant protein containing a heme (see Krainer et al., 2015, Microb. Cell Fact., 13;14:4). Expression of a recombinant heme containing protein in *P. pastoris* can be achieved by co-expressing one or more enzymes of the heme biosynthetic pathway from methanol-inducible promoters, although it would be appreciated that one or more of the genes involved in the heme biosynthetic pathway could be expressed from one or more constitutive promoters (see, e.g., U.S. Pat. No. 9,938,327, which is incorporated by reference in its entirety).

In addition, it is noted that a first nucleic acid encoding a first protein (e.g., an ALAS protein) operably linked to a promoter element as described herein can be physically separate from a second nucleic acid encoding a second protein (e.g., a heme-binding protein) operably linked to a promoter element (that is, the first and second nucleic acids can be completely separate molecules). Alternatively, a first nucleic acid encoding a first protein operably linked to a promoter element and a second nucleic acid encoding a second protein operably linked to a promoter element can be included in the same nucleic acid construct. In some embodiments, a first nucleic acid encoding a first protein operably linked to a promoter element can be contiguous with a second nucleic acid encoding a second protein operably linked to a promoter element. It would be appreciated by a skilled artisan that, if the second nucleic acid molecule encoding a second protein is contiguous with the first nucleic acid encoding a protein of interest, a single promoter, or promoter element therefrom, can be used to drive transcription of both or all of the genes (e.g., the nucleic acid encoding the first protein as well as the second protein).

Methods of introducing nucleic acids into cells (e.g., fungal cells, such as *Aspergillus* cells, *Trichoderma* cells, or yeast cells (e.g., methylotrophic yeast cells))are known in the art, and include, without limitation, transduction, electroporation, biolistic particle delivery, and chemical transformation.

In addition, methods of culturing cells (e.g., fungal cells, such as *Aspergillus* cells, *Trichoderma* cells, or yeast cells (e.g., methylotrophic yeast cells))are known in the art. See, for example, Pichia Protocols, *Methods In Molecular Biology*, 389, Cregg, Ed., 2007, $2^{nd}$ Ed., Humana Press, Inc. Under some circumstances, it may be desirable to introduce or add methanol to the culture media, although, as demonstrated herein, methanol is not required to obtain efficient expression at high levels of one or more proteins of interest. Under some circumstances (e.g., when one or more nucleic acids encoding enzyme(s) involved in heme biosynthesis are expressed), it may be desirable to supplement the culture media with iron or a pharmaceutically or metabolically acceptable (or GRAS) salt thereof.

The recombinant nucleic acid molecules described herein can be stably integrated into the genome of the cell (e.g., the fungal cell, such as *Aspergillus* cell, *Trichoderma* cell, or yeast cell (e.g., the methylotrophic yeast cell)), or can be extrachromosomally expressed from a replication-competent plasmid. Methods of achieving both are known and used in the art.

The methods provided herein also can include purifying the expressed protein. As used herein, an "enriched" protein is a protein that accounts for at least 5% (e.g., at least 6%, 7%, 8%, 9%, 10%, 15%, 20%, 25%, 30%, 35%, 40%, 45%, 50%, 55%, 60%, or more) by dry weight, of the mass of the production cell (e.g., fungal cell, such as *Aspergillus* cell, *Trichoderma* cell, or yeast cell (e.g., methylotrophic yeast cell)), or at least 10% (e.g., at least 15%, 20%, 25%, 30%, 35%, 40%, 45%, 50%, 55%, 60%, 65%, 70%, 75%, 80%, 90%, 95%, or 99%) by dry weight, the mass of the production cell lysate (e.g., excluding cell wall or membrane material). As used herein, a "purified" protein is a protein that has been separated or purified from cellular components that naturally accompany it. Typically, the protein is considered "purified" when it is at least 60% (e.g., at least 65%, 70% 75%, 80%, 85%, 90%, 95%, or 99%) by dry weight, free from the proteins and naturally occurring molecules with which it is naturally associated.

As used herein, nucleic acids can include DNA and RNA, and includes nucleic acids that contain one or more nucleotide analogs or backbone modifications. A nucleic acid can be single stranded or double stranded, which usually depends upon its intended use. Also provided are nucleic acids and polypeptides that differ from a given sequence. Nucleic acids and polypeptides can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to a given nucleic acid or polypeptide sequence.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, *Nucleic Acids Res.*, 31(13):3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule, thereby leading to changes in the amino acid sequence of the encoded polypeptide. For example, changes can be introduced into nucleic acid coding sequences using mutagenesis (e.g., site-directed mutagenesis, PCR-mediated mutagenesis, transposon mutagenesis, chemical mutagenesis, UV mutagenesis or radiation induced mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al., 1978, *Atlas of Protein Sequence and Structure,* 5(Suppl. 3):345-352, which provides frequency tables for amino acid substitutions), and a non-conservative substitution is one in which an amino acid residue is replaced with an amino acid residue that does not have a similar side chain. Nucleic acid and/or polypeptide sequences may be modified as described herein to improve one or more properties such as, without limitation, increased expression (e.g., transcription and/or translation), tighter regulation, deregulation, loss of catabolite repression, modified specificity, secretion, thermostability, solvent stability, oxidative stability, protease resistance, catalytic activity, and/or color.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

Vectors as described herein can be introduced into a host cell (e.g., fungal cell, such as an *Aspergillus* cell, a *Trichoderma* cell, or a yeast cell (e.g., a methylotrophic yeast cell)). As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as *E. coli,* or in insect cells, yeast or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in *PCR Primer: A Laboratory Manual,* Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A construct or vector containing a nucleic acid (e.g., a nucleic acid that encodes a polypeptide) also is provided. Constructs or vectors, including expression constructs or vectors, are commercially available or can be produced by recombinant DNA techniques routine in the art. A construct or vector containing a nucleic acid can have expression elements operably linked to such a nucleic acid, and further can include sequences such as those encoding a selectable marker (e.g., an antibiotic resistance gene). A construct or vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides include those that can be used in purification of the encoded polypeptide (e.g., 6xHis tag, glutathione S-transferase (GST)).

Nucleic acids also can be detected using hybridization. Hybridization between nucleic acids is discussed in detail in Sambrook et al. (1989, *Molecular Cloning: A Laboratory Manual,* 2nd Ed., Cold Spring Harbor Laboratory Press, Cold Spring Harbor, NY; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, CA).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Methods are described herein that can be used to generate a strain that lacks sequences for selection (i.e., that lacks a selectable marker). These methods include using a circular plasmid DNA vector and a linear DNA sequence; the circular plasmid DNA vector contains a selection marker and an origin of DNA replication (also known as an autonomously replicating sequence (ARS)), and the linear DNA sequence contains sequences for integration into the genome (e.g., the *Pichia* genome) by homologous recombination. The linear DNA molecule additionally can include nucleic acid sequences encoding one or more proteins of interest such as, without limitation, an ALAS, a heme-binding protein, or a third protein (e.g., a transcription factor or a protein involved in heme biosynthesis).

Cells (e.g., *Pichia* cells) can be transformed with both DNA molecules and the transformants selected by the presence of the selectable marker on the circular plasmid. Transformants then can be screened for integration of the linear DNA molecule into the genome using, for example, PCR. Once transformants with the correct integration of the marker-free linear DNA molecule are identified, the cells can be grown in the absence of selection for the circular plasmid. Because the marker-bearing plasmid is not stably maintained in the absence of selection, the plasmid is lost, often very quickly, after selection is relaxed. The resulting strain carries the integrated linear DNA in the absence of heterologous sequences for selection. Therefore, this approach can be used to construct strains (e.g., *Pichia* strains) that lack a selectable marker (e.g., a heterologous selection marker) with little to no impact on recombinant protein yield.

In accordance with the present disclosure, there may be employed conventional molecular biology, microbiology, biochemical, and recombinant DNA techniques within the skill of the art. Such techniques are explained fully in the literature. The materials and methods of the disclosure will be further described in the following examples, which do not limit the scope of the methods and compositions of matter described in the claims.

The materials and methods of the disclosure will be further described in the following examples, which do not limit the scope the claims.

EXEMPLARY EMBODIMENTS

Embodiment 1 is a cell comprising:
a first exogenous nucleic acid construct comprising a nucleotide sequence encoding an aminolevulinate synthase (ALAS) protein operably linked to a first promoter element, wherein the ALAS comprises at least a first heme responsive motif (HRM), and wherein the ALAS comprises a mutation in the first HRM; and
a second exogenous nucleic acid construct comprising a nucleotide sequence encoding a heme-binding protein, wherein the second exogenous nucleic acid construct comprising a nucleotide sequence encoding the heme-binding protein is operably linked to the first promoter element or is operably linked to a second promoter element.

Embodiment 2 is the cell of embodiment 1, wherein the cell is a fungal cell.

Embodiment 3 is the cell of embodiment 2, wherein the cell is an *Aspergillus* or *Trichoderma* cell.

Embodiment 4 is the cell of any one of embodiments 1-3, wherein the cell is a yeast cell.

Embodiment 5 is the cell of embodiment 4, wherein the yeast cell is a methylotrophic yeast cell.

Embodiment 6 is the cell of embodiment 5, wherein the methylotrophic yeast cell is a *Pichia* cell, a *Candida* cell, a *Hansenula* cell, or a *Torulopsis* cell.

Embodiment 7 is the cell of any one of embodiments 5-6, wherein the methylotrophic yeast cell is a *Pichia methanolica* cell, a *Pichia pastoris* cell, a *Candida boidinii* cell, or a *Hansenula polymorpha* cell.

Embodiment 8 is the cell of any one of embodiments 5-7, wherein the methylotrophic yeast cell is a *Pichia pastoris* cell.

Embodiment 9 is the cell of any one of embodiments 1-8, wherein the mutation in the first HRM is a mutation from a cysteine to a different amino acid.

Embodiment 10 is the cell of any one of embodiments 1-9, wherein the ALAS protein comprises a second HRM, and wherein the ALAS protein comprises a mutation in the second HRM.

Embodiment 11 is the cell of embodiment 10, wherein the mutation in the second HRM is a mutation from a cysteine to a different amino acid.

Embodiment 12 is the cell of embodiment 10 or embodiment 11, wherein the different amino acid is the same for the mutation in the first HRM and the mutation in the second HRM.

Embodiment 13 is the cell of embodiment 10 or embodiment 11, wherein the different amino acid is not the same for the mutation in the first HRM and the mutation in the second HRM.

Embodiment 14 is the cell of any one of embodiments 10-13, wherein the ALAS protein comprises a third HRM, and wherein the ALAS protein comprises a mutation in the third HRM.

Embodiment 15 is the cell of embodiment 14, wherein the mutation in the third HRM is a mutation from a cysteine to a different amino acid.

Embodiment 16 is the cell of embodiment 15, wherein the different amino acid is the same for the mutation in the first HRM, the mutation in the second HRM, and the mutation in the third HRM.

Embodiment 17 is the cell of any one of embodiments 9-16, wherein the different amino acid is selected from the group consisting of arginine, histidine, lysine, serine, threonine, asparagine, glutamine, selenocysteine, glycine, proline, alanine, isoleucine, leucine, methionine, glutamic acid, aspartic acid, phenylalanine, tryptophan, tyrosine, and valine.

Embodiment 18 is the cell of any one of embodiments 9-16, wherein the different amino acid is selected from a nonpolar aliphatic amino acid, an aromatic amino acid, a polar uncharged amino acid, or a positively charged amino acid.

Embodiment 19 is the cell of embodiment 18, wherein the nonpolar aliphatic amino acid is selected from the group consisting of glycine, proline, alanine, isoleucine, leucine, methionine, and valine.

Embodiment 20 is the cell of embodiment 18, wherein the aromatic amino acid is selected from the group consisting of phenylalanine, tryptophan, and tyrosine.

Embodiment 21 is the cell of embodiment 18, wherein the polar uncharged amino acid is selected from the group consisting of a polar uncharged amino acid serine, threonine, asparagine, or glutamine.

Embodiment 22 is the cell of embodiment 18, wherein the positively charged amino acid is selected from the group consisting of arginine, histidine, and lysine.

Embodiment 23 is the cell of any one of embodiments 9-22, wherein the different amino acid is serine.

Embodiment 24 is the cell of any one of embodiments 9-22, wherein the different amino acid is alanine.

Embodiment 25 is the cell of any one of embodiments 9-22, wherein the different amino acid is phenylalanine.

Embodiment 26 is the cell of any one of embodiments 9-22, wherein the different amino acid is histidine.

Embodiment 27 is the cell of any one of embodiments 1-26, wherein the first HRM is HRM1.

Embodiment 28 is the cell of any one of embodiments 10-27, wherein the second HRM is HRM2.

Embodiment 29 is the cell of any one of embodiments 1-26, wherein the first HRM is HRM2.

Embodiment 30 is the cell of any one of embodiments 10-27, wherein the second HRM is HRM1.

Embodiment 31 is the cell of any one of embodiments 1-30, wherein the first exogenous nucleic acid construct comprises a nucleic acid sequence having at least 90% sequence identity to the nucleic acid sequence in SEQ ID NO: 28.

Embodiment 32 is the cell of any one of embodiments 1-30, wherein the first exogenous nucleic acid construct comprises a nucleic acid sequence having at least 95% sequence identity to the nucleic acid sequence in SEQ ID NO: 28.

Embodiment 33 is the cell of any one of embodiments 1-30, wherein the first exogenous nucleic acid construct comprises the nucleic acid sequence in SEQ ID NO: 30.

Embodiment 34 is the cell of any one of embodiments 1-32, wherein the ALAS protein comprises an amino acid sequence having at least 90% sequence identity to the amino acid sequence in SEQ ID NO: 29.

Embodiment 35 is the cell of any one of embodiments 1-32, wherein the ALAS protein comprises an amino acid sequence having at least 95% sequence identity to the amino acid sequence in SEQ ID NO: 29.

Embodiment 36 is the cell of any one of embodiments 1-35, wherein the ALAS protein comprises the amino acid sequence in SEQ ID NO: 31.

Embodiment 37 is the cell of any one of embodiments 1-36, wherein the heme-binding protein is selected from the group consisting of a globin, a cytochrome, a cytochrome c oxidase, a ligninase, a catalase, and a peroxidase.

Embodiment 38 is the cell of any one of embodiments 1-36, wherein the heme-binding protein is selected from the group consisting of an androglobin, a chlorocruorin, a cytoglobin, an erythrocruorin, a flavohemoglobin, a globin E, a globin X, a globin Y, a hemoglobin, a histoglobin, a leghemoglobin, a myoglobin, a neuroglobin, a non-symbiotic hemoglobin, a protoglobin, and a truncated hemoglobin.

Embodiment 39 is the cell of any one of embodiments 1-36, wherein the heme-binding protein is a non-symbiotic hemoglobin.

Embodiment 40 is the cell of any one of embodiments 1-36, wherein the heme-binding protein is a leghemoglobin.

Embodiment 41 is the cell of any one of embodiments 1-40, wherein the heme-binding protein comprises an amino acid sequence having at least 90% sequence identity to an amino acid sequence in any one of SEQ ID NOs: 1-27.

Embodiment 42 is the cell of any one of embodiments 1-41, further comprising a third nucleic acid construct comprising a nucleotide sequence encoding a transcription factor, wherein the third nucleic acid construct is operably linked to the first promoter element, the second promoter element, or a third promoter element.

Embodiment 43 is the cell of embodiment 42, wherein the first promoter element comprises a recognition sequence for the transcription factor.

Embodiment 44 is the cell of any one of embodiments 42 or 43, wherein the second exogenous nucleic acid construct is operably linked to a second promoter element, and wherein the second promoter element comprises a recognition sequence for the transcription factor.

Embodiment 45 is the cell any one of embodiments 42 or 43, wherein the third nucleic acid construct is operably linked to the third promoter element, and wherein the third promoter element comprises a recognition sequence for the transcription factor.

Embodiment 46 is the cell of any one of embodiments 1-45, further comprising a fourth nucleic acid construct comprising a nucleotide sequence encoding a protein involved in heme biosynthesis, wherein the fourth nucleic acid construct is operably linked to the first promoter element, the second promoter element, the third promoter element, or a fourth promoter element.

Embodiment 47 is the cell of embodiment 46, wherein the protein involved in heme biosynthesis is selected from the group consisting of ALA dehydratase, porphobilinogen deaminase, UPG III synthase, UPG III decarboxylase, CPG oxidase, PPG oxidase, and ferrochelatase.

Embodiment 48 is the cell of any one of embodiments 1-47, wherein the first exogenous nucleic acid construct is a heterologous nucleic acid construct.

Embodiment 49 is the cell of any one of embodiments 1-48, wherein the second exogenous nucleic acid construct is a heterologous nucleic acid construct.

Embodiment 50 is the cell of any one of embodiments 1-47, wherein the heme-binding protein is an exogenous heme-binding protein.

Embodiment 51 is the cell of any one of embodiments 1-47 or 50, wherein the heme-binding protein is a heterologous heme-binding protein.

Embodiment 52 is a method of producing a heme-binding protein in a cell comprising:
  expressing a first exogenous nucleic acid construct comprising a nucleotide sequence encoding an aminolevulinate synthase (ALAS) protein operably linked to a first promoter element, wherein the ALAS comprises at least a first heme responsive motif (HRM), and wherein the ALAS comprises a mutation in the first HRM; and
  expressing a second exogenous nucleic acid construct comprising a nucleotide sequence encoding a heme-binding protein,
wherein the second exogenous nucleic acid construct comprising a nucleotide sequence encoding the heme-binding protein is operably linked to the first promoter element or is operably linked to a second promoter element.

Embodiment 53 is the method of 52, wherein the method produces the heme-binding protein in a titer that is at least 5% greater than a corresponding method lacking the first exogenous nucleic acid construct.

Embodiment 54 is the method of embodiment 52 or embodiment 53, wherein the method produces the heme-binding protein in a titer that is at least 10% greater than a corresponding method lacking the first exogenous nucleic acid construct.

Embodiment 55 is the method of embodiment 52 or embodiment 53, wherein the method produces the heme-binding protein in a titer that is at least 15% greater than a corresponding method lacking the first exogenous nucleic acid construct.

Embodiment 56 is the method of embodiment 52 or embodiment 53, wherein the method produces the heme-binding protein in a titer that is at least 20% greater than a corresponding method lacking the first exogenous nucleic acid construct.

Embodiment 57 is the method of embodiment 52, wherein the method produces the heme-binding protein in a titer that is at least 5% greater than a corresponding method lacking the mutation in the first HRM.

Embodiment 58 is the method of embodiment 52, wherein the method produces the heme-binding protein in a titer that is at least 10% greater than a corresponding method lacking the mutation in the first HRM.

Embodiment 59 is the method of embodiment 52, wherein the method produces the heme-binding protein in a titer that is at least 15% greater than a corresponding method lacking the mutation in the first HRM.

Embodiment 60 is the method of embodiment 52, wherein the method produces the heme-binding protein in a titer that is at least 20% greater than a corresponding method lacking the mutation in the first HRM.

Embodiment 61 is the method of any one of embodiments 52-60, wherein the method is carried out in the absence of added methanol.

Embodiment 62 is the method of any one of embodiments 52-61, wherein the cell is a fungal cell.

Embodiment 63 is the method of embodiment 62, wherein the cell is an *Aspergillus* or *Trichoderma* cell.

Embodiment 64 is the method of any one of embodiments 62-63, wherein the cell is a yeast cell.

Embodiment 65 is the method of embodiment 64, wherein the yeast cell is a methylotrophic yeast cell.

Embodiment 66 is the method of embodiment 65, wherein the methylotrophic yeast cell is a *Pichia* cell, a *Candida* cell, a *Hansenula* cell, or a *Torulopsis* cell.

Embodiment 67 is the method of any one of embodiments 65-66, wherein the methylotrophic yeast cell is a *Pichia methanolica* cell, a *Pichia pastoris* cell, a *Candida boidinii* cell, or a *Hansenula polymorpha* cell.

Embodiment 68 is the method of any one of embodiments 51-53, wherein the methylotrophic yeast cell is a *Pichia pastoris* cell.

Embodiment 69 is the method of any one of embodiments 52-68, wherein the mutation in the first HRM is a mutation from a cysteine to a different amino acid.

Embodiment 70 is the method of any one of embodiments 52-69, wherein the ALAS protein comprises a second HRM, and wherein the ALAS protein comprises a mutation in the second HRM.

Embodiment 71 is the method of embodiment 70, wherein the method produces the heme-binding protein in a titer that is at least 5% greater than a corresponding method lacking the mutations in the first HRM and second HRM.

Embodiment 72 is the method of embodiment 70, wherein the method produces the heme-binding protein in a titer that is at least 10% greater than a corresponding method lacking the mutations in the first HRM and second HRM.

Embodiment 73 is the method of embodiment 70, wherein the method produces the heme-binding protein in a titer that is at least 15% greater than a corresponding method lacking the mutations in the first HRM and second HRM.

Embodiment 74 is the method of embodiment 70, wherein the method produces the heme-binding protein in a titer that is at least 20% greater than a corresponding method lacking the mutations in the first HRM and second HRM.

Embodiment 75 is the method of any one of embodiments 70-74, wherein the mutation in the second HRM is a mutation from a cysteine to a different amino acid.

Embodiment 76 is the method of any one of embodiments 70-75, wherein the different amino acid is the same for the mutation in the first HRM and the mutation in the second HRM.

Embodiment 77 is the method of any one of embodiments 70-75, wherein the different amino acid is not the same for the mutation in the first HRM and the mutation in the second HRM.

Embodiment 78 is the cell of any one of embodiments 70-77, wherein the ALAS protein comprises a third HRM, and wherein the ALAS protein comprises a mutation in the third HRM.

Embodiment 79 is the cell of embodiment 78, wherein the mutation in the third HRM is a mutation from a cysteine to a different amino acid.

Embodiment 80 is the cell of embodiment 79, wherein the different amino acid is the same for the mutation in the first HRM, the mutation in the second HRM, and the mutation in the third HRM.

Embodiment 81 is the method any one of embodiments 69-80, wherein the different amino acid is selected from the group consisting of arginine, histidine, lysine, serine, threonine, asparagine, glutamine, selenocysteine, glycine, proline, alanine, isoleucine, leucine, methionine, aspartic acid, glutamic acid, phenylalanine, tryptophan, tyrosine, and valine.

Embodiment 82 is the method of any one of embodiments 69-80, wherein the different amino acid is selected from a nonpolar aliphatic amino acid, an aromatic amino acid, a polar uncharged amino acid, or a positively charged amino acid.

Embodiment 83 is the method of embodiment 82, wherein the nonpolar aliphatic amino acid is selected from the group consisting of glycine, proline, alanine, isoleucine, leucine, methionine, and valine.

Embodiment 84 is the method of embodiment 82, wherein the aromatic amino acid is selected from the group consisting of phenylalanine, tryptophan, and tyrosine.

Embodiment 85 is the cell of embodiment 82, wherein the polar uncharged amino acid is selected from the group consisting of a polar uncharged amino acid serine, threonine, asparagine, or glutamine.

Embodiment 86 is the method of embodiment 82, wherein the positively charged amino acid is selected from the group consisting of arginine, histidine, and lysine.

Embodiment 87 is the method of any one of embodiments 69-86, wherein the different amino acid is serine.

Embodiment 88 is the method of any one of embodiments 69-86, wherein the different amino acid is alanine.

Embodiment 89 is the method of any one of embodiments 69-86, wherein the different amino acid is phenylalanine.

Embodiment 90 is the method of any one of embodiments 69-86, wherein the different amino acid is histidine.

Embodiment 91 is the cell of any one of embodiments 52-90, wherein the first HRM is HRM1.

Embodiment 92 is the cell of any one of embodiments 70-91, wherein the second HRM is HRM2.

Embodiment 93 is the cell of any one of embodiments 52-90, wherein the first HRM is HRM2.

Embodiment 94 is the cell of any one of embodiments 70-91, wherein the second HRM is HRM1.

Embodiment 95 is the method of any one of embodiments 52-94, wherein the first exogenous nucleic acid construct comprises a nucleic acid sequence having at least 90% sequence identity to the nucleic acid sequence in SEQ ID NO: 28.

Embodiment 96 is the method of any one of embodiments 52-95, wherein the first exogenous nucleic acid construct comprises a nucleic acid sequence having at least 95% sequence identity to the nucleic acid sequence in SEQ ID NO: 28.

Embodiment 97 is the method of any one of embodiments 52-96, wherein the first exogenous nucleic acid construct comprises the nucleic acid sequence in SEQ ID NO: 30.

Embodiment 98 is the method of any one of embodiments 52-97, wherein the ALAS protein comprises an amino acid sequence having at least 90% sequence identity to the amino acid sequence in SEQ ID NO: 29.

Embodiment 99 is the method of any one of embodiments 52-98, wherein the ALAS protein comprises an amino acid sequence having at least 95% sequence identity to the amino acid sequence in SEQ ID NO: 29.

Embodiment 100 is the method of any one of embodiments 52-99, wherein the ALAS protein comprises the amino acid sequence in SEQ ID NO: 31.

Embodiment 101 is the method of any one of embodiments 52-100, wherein the heme-binding protein is selected from the group consisting of a globin, a cytochrome, a cytochrome c oxidase, a ligninase, a catalase, and a peroxidase.

Embodiment 102 is the method of any one of embodiments 52-100, wherein the heme-binding protein is selected from the group consisting of an androglobin, a chlorocruorin, a cytoglobin, an erythrocruorin, a flavohemoglobin, a globin E, a globin X, a globin Y, a hemoglobin, a histoglobin, a leghemoglobin, a myoglobin, a neuroglobin, a non-symbiotic hemoglobin, a protoglobin, and a truncated hemoglobin.

Embodiment 103 is the method of any one of embodiments 52-100, wherein the heme-binding protein is a non-symbiotic hemoglobin.

Embodiment 104 is the method of any one of embodiments 52-100, wherein the heme-binding protein is a leghemoglobin.

Embodiment 105 is the method of any one of embodiments 52-100, wherein the heterologous heme-binding protein comprises an amino acid sequence having at least 90% sequence identity to an amino acid sequence in any one of SEQ ID NOs: 1-27.

Embodiment 106 is the method of any one of embodiments 52-105, further comprising expressing a third nucleic acid construct comprising a nucleotide sequence encoding a transcription factor, wherein the third nucleic acid construct is operably linked to the first promoter element, the second promoter element, or a third promoter element.

Embodiment 107 is the method of embodiment 106, wherein the first promoter element comprises a recognition sequence for the transcription factor.

Embodiment 108 is the method of embodiment 107, wherein the second exogenous nucleic acid construct is operably linked to a second promoter element, and wherein the second promoter element comprises a recognition sequence for the transcription factor.

Embodiment 109 is the method of any one of embodiments 107-108, wherein the third nucleic acid construct is operably linked to the third promoter element, and wherein the third promoter element comprises a recognition sequence for the transcription factor.

Embodiment 110 is the method of any one of embodiments 52-109, further comprising expressing a fourth nucleic acid construct comprising a nucleotide sequence encoding a protein involved in heme biosynthesis, wherein the fourth nucleic acid construct is operably linked to the first promoter element, the second promoter element, the third promoter element, or a fourth promoter element.

Embodiment 111 is the method of embodiment 110, wherein the protein involved in heme biosynthesis is selected from the group consisting of ALA dehydratase, porphobilinogen deaminase, UPG III synthase, UPG III decarboxylase, CPG oxidase, PPG oxidase, and ferrochelatase.

Embodiment 112 is the method of any one of embodiments 52-111, wherein the first exogenous nucleic acid construct is a heterologous nucleic acid construct.

Embodiment 113 is the method of any one of embodiments 52-112, wherein the second exogenous nucleic acid construct is a heterologous nucleic acid construct.

Embodiment 114 is the method of any one of embodiments 52-113, wherein the heme-binding protein is an exogenous heme-binding protein.

Embodiment 115 is the method of any one of embodiments 52-111 or 114, wherein the heme-binding protein is a heterologous heme-binding protein.

EXAMPLES

Example 1

Polymerase Chain Reaction

Genes of interest were amplified from genomic DNA or plasmid DNA templates using Phusion High-fidelity PCR master mix (New England Biolabs, Cat #M0531), 0.6 µM each of forward and reverse primers and 10-50 ng of template DNA. The reaction conditions were as follows:

| 1 cycle | Initial Denaturation | 98° C. | 1 min |
|---|---|---|---|
| 25 cycles | Denaturation | 98° C. | 10 sec |
| | Annealing | 60° C. | 20 sec |
| | Extension | 72° C. | 30 sec per kb |
| 1 cycle | Final Extension | 72° C. | 5 min |
| | Hold | 4° C. | Forever |

*Pichia pastoris* ALAS gene (KEGG identifier PAS_chr2-1_0716, which can be accessed at the Kyoto Encyclopedia of Genes and Genomes (KEGG) website) was amplified using primers (ATGGAGTTTGTCGCCCGTCAG; SEQ ID NO: 65) and (CTACAATCTGACTCCTGATGAGGTTTC; SEQ ID NO: 66) from genomic DNA. In the examples, wtALAS denotes this native sequence of ALAS (SEQ ID NO: 28).

Example 2

Cloning of ALAS and Mutagenesis

PCR product was purified using NucleoSpin Gel and PCR Clean-Up (Takara Bio, Cat #740609) and cloned in pCR-BluntII-TOPO vector using Zero Blunt TOPO PCR Cloning Kit (Thermo Fisher Scientific, Cat #K280020) following the manufacturer's recommendation. Site directed mutagenesis was carried out on the resulting vector (40 ng of purified plasmid) using two sets of primers (set1: CGTCAGTCCAT-GAATGCCTCTCCCTTTGTCAGGTCAACTTC; SEQ ID NO: 37 and GAAGTTGACCTGACAAAGGGAGAGG-CATTCATGGACTGACG; SEQ ID NO: 38, set2: GCTGC-TACTGCTAGTCATTCTCCCGTGGTTGGCCCTG; SEQ ID NO: 39 and CAGGGCCAACCACGG-GAGAATGACTAGCAGTAGCAGC; SEQ ID NO: 40) and QuikChange II XL Site-Directed Mutagenesis Kit (Agilent, Cat #200521) to create mutALAS carrying mutations of cysteine residues at positions 12 and 39 to serine residues (SEQID NO: 30). In the Examples, mutALAS specifically denotes these two mutations unless specified otherwise. The reaction conditions were as follows:

| 1 cycle | Initial Denaturation | 95° C. | 1 min |
|---|---|---|---|
| 18 cycles | Denaturation | 95° C. | 50 sec |
| | Annealing | 60° C. | 50 sec |
| | Extension | 68° C. | 11 min |
| 1 cycle | Final Extension | 68° C. | 7 min |
| | Hold | 4° C. | Forever |

Single cysteine to serine mutation, C12S or C39S was performed by site directed mutagenesis on vector carrying wtALAS using primer set1 (SEQ ID NO: 37, SEQ ID NO: 38) and set2 (SEQ ID NO: 39, SEQ ID NO: 40) respectively.

Example 3

Figure 5:
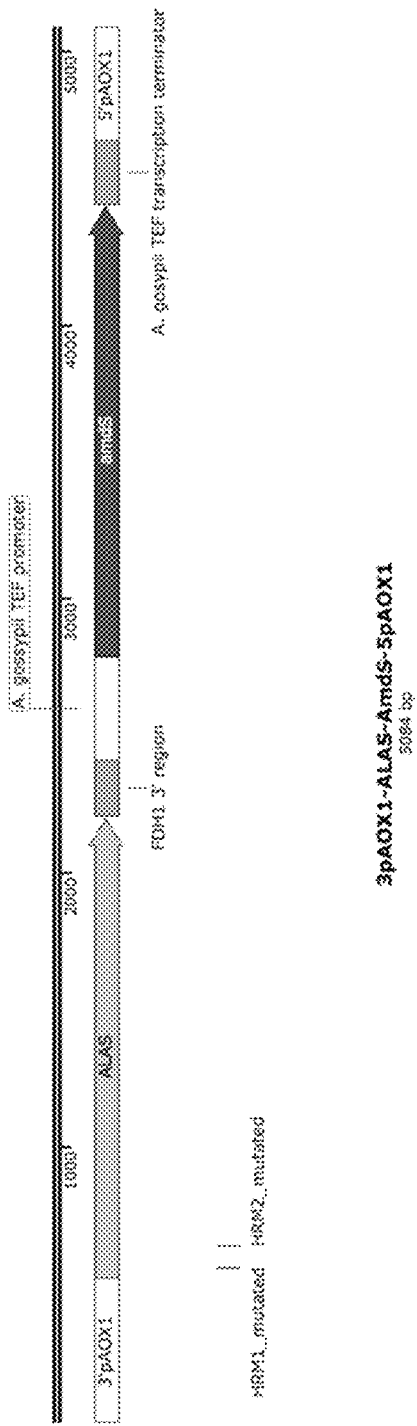
FIG. 5 provides an exemplary construct diagram of a mutated ALAS.

Construction of ALAS (Wild-Type or Mutated, C12S, C39S) Gene Integration Cassette Integration cassette of wtALAS or mutALAS was designed such that gene integration occurred under the methanol-inducible alcohol oxidase 1 (AOX1) promoter element from *Pichia pastoris* and before the translation stop signal immediately followed by the transcription terminator sequence from the *Pichia pastoris* FDH1 gene. The linear constructs contained the 3' half of the promoter element, followed by ALAS gene (wild-type or mutant), followed by the FDH1 transcription terminator. This was immediately followed by the selection cassette containing the pTEF promoter element from *Ashbya gossypii*, the acetamidase gene (amdS) from *Aspergillus nidulans* and the TEF terminator from *Ashbya gossypii*. Finally, the construct contained the 5' half of the promoter element (See, e.g., FIG. 5).

Overlapping PCR was used to create the linear constructs [3'pAOX1-ALAS (wt/mut)-FDH1tt-pTEF-amdS-TEFtt-5'pAOX1). Primers Used to Amplify the Linear Constructs:

| Overlapping PCR | Primer sequences | SEQ ID NO: |
|---|---|---|
| PCR1 | AAACGCTGTCTTGGAACCTAATATGAC | 41 |
| | GACGGGCGACAAACTCCATCGTTTCGA ATAATTAGTTG | 42 |
| PCR2 | CAACTAATTATTCGAAACGATGGAGTTT GTCGCCCGTCAG | 43 |
| | AATTAAATACATTTCAACTACAATCTGA CTCCTGATGAGGTTTCG | 44 |
| PCR3 | CCTCATCAGGAGTCAGATTGTAGTTGAA ATGTATTTAATTTG | 45 |
| | AAACTGTCAGTTTTGGGCCATTTG | 46 |

Individual PCR reaction conditions were performed as indicated above. PCR products were purified using Nucleo-Spin Gel and PCR Clean-Up (Takara Bio, Cat #740609). The final overlapping PCR product was performed using 0.5 U Platinum Pfx DNA Polymerase (Thermo Fisher Scientific, Cat#11708039), 1× amplification buffer, 0.3 mM dNTPs and 1 mM $MgCl_2$ by mixing the three purified PCR amplicons in an equimolar ratio in a 2-part PCR reaction. The PCR conditions were:

Part 1:

| 1 cycle | Initial Denaturation | 94° C. | 2 min |
|---|---|---|---|
| 15 cycles | Denaturation | 94° C. | 15 sec |
| | Annealing | 58° C. | 30 sec |
| | Extension | 68° C. | 5 min |
| | Hold | 4° C. | |

Following part 1, the reaction mixes were spiked with primers AAACGCTGTCTTGGAACCTAATATGAC (SEQ ID NO: 41) and AAACTGTCAGTTTTGGGCCATTTG (SEQ ID NO: 46) (0.3 uM final concentration) and 1.5U Pfx and continued to part 2.

Part 2:

| 1 cycle | Initial Denaturation | 94° C. | 2 min |
|---|---|---|---|
| 20 cycles | Denaturation | 94° C. | 15 sec |
| | Annealing | 58° C. | 30 sec |
| | Extension | 68° C. | 5 min |
| | Hold | 4° C. | Forever |

Sequences of exemplary mutant nucleic acids (e.g., SEQ ID NO: 30) and proteins (e.g., SEQ ID NO: 31) are provided in FIG. 7.

Expression plasmids of wtALAS and mutALAS were constructed in an autonomous replicating vector (panARS) under a modified pAOX1 followed by the transcription terminator sequence from the *Pichia pastoris* FDH1 gene. The vector conferred resistance to G418 (Geneticin). Cloning of inserts GFP, wtALAS and mutALAS in the vector was performed using Gibson Assembly Master Mix (New England Biolabs, catalog # E2611L) following manufacturer's recommendation.

Example 4

Preparation of *P. pastoris* Transformation-Competent Cells

Selected strains of *P. pastoris* (*K. phaffii*) were grown to mid-exponential growth phase (~2 OD) in 25 ml YPD medium. Cells were collected by centrifugation at 930×g for 15 minutes. The cell pellet was resuspended in 2 ml of a solution of 80% YPD and 200 mM HEPES, pH 6.8. 75 µl of 1 M DTT was added. The resuspended cell pellet was mixed at 100 rpm at 30° C. for 25 minutes. A 40 ml volume of ice cold, sterile water was added to the suspension, and the cells were collected by centrifugation at 1125×g for 15 minutes and placed on ice. The cell pellet was resuspended in 40 ml ice cold water and collected as before for two additional wash steps. The cell pellet was then resuspended in 20 ml of ice cold 1 M sorbitol and collected by centrifugation as before. The final cell pellet was suspended in 0.3 ml ice cold, sterile 1 M sorbitol, aliquoted and frozen at −80° C.

Example 5

Transformation into *P. pastoris*

For genome integration, 100-300 ng of linearized DNA was transformed into 30 µl of electrocompetent *P. pastoris* cells using a 1 mm gap GenePulser cuvette (Bio-Rad, Cat# 1652083) with a GenePulser (Bio-Rad) set at 1.15 kV. 1 ml of YPD/1M sorbitol (1:1 vol/vol) was added immediately to the cells. The cells were allowed to recover for 3 h at 30° C. with shaking at 100 rpm. 100 µl of the recovery mixture was plated on yeast carbon base plates containing 5 mM acetamide (Teknova, Cat#Y5216). Plates were incubated at 30° C. for 48 hours. Individual clones were streaked onto yeast carbon base plates containing acetamide to obtain single colonies and the isolated colonies were used to do colony PCR or gDNA prep to confirm gene integration into the chromosome and sequence the integration construct.

For plasmid DNA transformation, the same steps were followed as for genome integration except that after electroporation and recovery of cells, 50-100 µl of the recovery mixture was plated on YPD plates containing 300 ug/ml G418 (Geneticin).

Example 6

Construction of Strains St2, St3, St5 and St6

A high yielding parent strain (St1) had pre-existing recombinant ALAS under the methanol-inducible strong promoter pAOX1 (alcohol oxidase 1) in addition to other pAOX1-driven heme enzymes, the carbon-responsive transcription factor MxR1 and multiple copies of LegH. A low yielding parent LegH strain (St4) lacked recombinant MxR1, ALAS and other heme enzymes except aminolevulinate dehydratase (ALAD).

Competent St1 cells (Table 1; a high LegH titer strain) were transformed with each of the linear cassettes (for wtALAS and mutALAS) and transformants containing the amdS selection cassette were selected based on their ability to grow on agar plates containing acetamide as the sole nitrogen source. The resulting strains (St2 and St3 with integrated cassette for wtALAS and mutALAS respectively, Table 1) were purified, isolated and the presence of pAOX1 driven wtALAS or mutALAS was verified by colony PCR and sequencing. Similarly, competent St4 cells (a low LegH titer strain) were transformed with linear cassettes for wtALAS and mutALAS to obtain St5 and St6 respectively.

TABLE 1

Strains with LegH integrated in genome

| Parent | 1 extra copy of recombinant wtALAS added | 1 extra copy of recombinant mutALAS added |
|---|---|---|
| High LegH titer strain (Strain St1) | Strain St2 | Strain St3 |
| Low LegH titer strain (Strain St4) | Strain St5 | Strain St6 |

Example 7

ALAS Gene Copy Number Analysis

ALAS gene copy number in different strains was measured by probe-based qPCR. Briefly, genomic DNA (20ng) was amplified with 1x PrimeTime gene expression mastermix (Integrated DNA Technologies, Cat #1055770) and PrimeTime qPCR Probe Assays in a real-time qPCR CFX96 machine (Bio-Rad). qPCR normalization was performed with respect to actin. A double delta Ct analysis method was followed to calculate the relative copy number of gene of interest between strains. Primer and probe sequences were:

| Gene | Primer sequence | SEQ ID. NO. | Probe sequence | SEQ ID. NO. |
|---|---|---|---|---|
| ALAS | GCTCTCCAACA GCAGAGATAC | 47 | 6-FAM/AAGCCCAAA/ Zen/CCTCCGACATTG CTA/3IABkFQ | 51 |
|  | GTCCATACGGA TCGGAGAAAC | 48 |  |  |
| Actin | AGCAACATCC CTGATTCCG | 49 | HEX/TCGCCGTAA/ Zen/GTTCTTGGTT TAGACGTTC/ 3IABkFQ | 52 |
|  | ATGCGTACCTT CAATCCTGG | 50 |  |  |

The engineered strains (Table 1) contained identical number of extra ALAS gene copies, either one copy of wtALAS or mutALAS, as measured by qPCR of ALAS normalized to actin levels. Hence, ALAS gene dosage was ruled out for any difference in the phenotype of the resulting strains (e.g., St2 vs St3 and St5 vs St6).

Example 8

PCR Detection of Heme Enzyme, MxR1, LegH and Mb Genes

Strain characterization was done by PCR for pAOX1-driven recombinant heme biogenesis pathway enzyme, MxR1 and LegH genes. Forward primer sequence for PCR was TAGCGCAGTCTCTCTATCGCTTC (SEQ ID NO: 53) specific to pAOX1. Reverse primer was specific to each gene of interest as shown below.

| Gene | Reverse Primer | Amplicon size | SEQ ID NO: |
|---|---|---|---|
| 5-aminolevulinate synthase | CACTGGGTTG TGCACATTGG | 1995 bp | 54 |
| Delta-aminolevulinate dehydratase | ACAATATTCT TCTCTGCCGC | 1268 bp | 55 |
| Phorphobilinogen deaminase | TTGATCTCGTC AAGAATGCG | 1358 bp | 56 |
| Uroporphyrinogen III synthase | TAGGTGCCACAA CTTTTGGTTTC | 1102 bp | 57 |
| Uroporphyrinogen decarboxylase | GATCCAATGCGA TGACATTCTTGT | 1430 bp | 58 |
| Coproporphyrinogen III oxidase | ACCTGCAATAAC TCCTCTTCTCTG | 1301 bp | 59 |
| Protoporphyrinogen oxidase | CCACTGAGGGTA GCCGAATC | 2027 bp | 60 |
| Ferrochelatase | GGGCTCTGAAAA ACTCTTTTGG | 1486 bp | 61 |
| MxR1 | GCATGTCTCAATAA CAGATCTCGACGG | 629 bp | 62 |
| LegH | AAGCCTCTTGTTTT TCTGTAAATGCAC | 382 bp | 63 |
| Bovine Mb | TGATGGCGTCCGA GATGAACTC | 688 bp | 64 |

Results of these reactions are shown below.

| Recombinant Gene (under pAOX1) | St1 | St2 | St3 | St4 | St5 | St6 | St7 |
|---|---|---|---|---|---|---|---|
| 5-aminolevulinate synthase | x | x | x | — | x | x | x |
| Delta-aminolevulinate dehydratase | x | x | x | x | x | x | x |
| Phorphobilinogen deaminase | x | x | x | — | — | — | x |
| Uroporphyrinogen III synthase | x | x | x | — | — | — | x |
| Uroporphyrinogen decarboxylase | x | x | x | — | — | — | x |
| Coproporphyrinogen III oxidase | x | x | x | — | — | — | x |
| Protoporphyrinogen oxidase | x | x | x | — | — | — | x |
| Ferrochelatase | x | x | x | — | — | — | x |
| MxR1 | x | x | x | — | — | — | x |
| LegH | x | x | x | x | x | x | — |
| Mb (Bovine Myoglobin) | — | — | — | — | — | — | x |

Example 9

Shake Flask Cultivation of Strains St4, St5 and St6

The strains were inoculated into growth media (1% yeast extract, 2% peptone, supplemented with 1% glycerol) overnight at 30° C. with shaking at 200 rpm. The next day the overnight cultures were diluted to an OD600 of 0.5-0.7 with YP media supplemented with 1% methanol and 1% dextrose. The cultures were grown for 48 hours and harvested by centrifugation at ~4000 g for 15 mins at 4° C.

The low LegH titer strain, St4, didn't have a pre-existing copy of recombinant ALAS, unlike St1. Integrating a copy of mutALAS (St6) led to a ~30% improvement in LegH titer compared to St5 (wtALAS). The titer calculation is based on LegH content as measured by a liquid chromatography method as described in Example 13.

The relative LegH titer is shown in Table 2.

TABLE 2

|  | St5 | St6 |
|---|---|---|
| Relative LegH titer | 1.00 | 1.32 |

Example 10

2L Cultivation of Strains St1, St2 and St3

Strains St1, St2 and St3 were grown in 2L fermentation tanks in media containing dextrose as the principal carbon source at 30° C. No methanol was used. In the background of a high LegH titer strain (St1) that contained pre-existing recombinant ALAS, St3 overexpressing mutALAS improved LegH titer by >30% over the parent St1. When compared to wtALAS (in St2), mutALAS (in St3) resulted in a 20% improvement in LegH titer. The titer calculation is based on LegH content as measured by a liquid chromatography method as described in Example 13.

The relative LegH titer is shown in Table 3.

TABLE 3

|  | St1 | St2 | St3 |
|---|---|---|---|
| Relative LegH titer | 1.00 | 1.10 | 1.37 |

Hence, mutating both the ALAS HRMs and overexpressing the mutated ALAS (mutALAS) in Pichia strains with different LegH titer led to further improvement in LegH titer. Furthermore, this suggested that mutALAS improved LegH titer independent of the strain genetic makeup (MxR1 and heme enzymes other than ALAS), and presence of methanol.

Example 11 mutALAS Improved Heme Levels

A quantitative assay for total heme based on reversed-phase high-performance liquid chromatography indicated that strains with mutALAS accumulated more heme levels than wtALAS containing strains. Shown in Table 4 is heme quantification in strain St3 (mutALAS) vs strain St2 (wtALAS). Additionally, mutALAS increased heme loading in multiple strains.

TABLE 4

|  | St2 | St3 |
|---|---|---|
| Relative heme titer | 1.00 | 2.7 |

Example 12

ALAS Protein Levels with mutALAS

It is generally believed that heme regulates ALAS levels in a feedback fashion to regulate its own levels. At the protein level, the ALAS level was higher 3-fold in St3 (mutALAS) compared to St2 (wtALAS) (Table 5) as quantitated by shotgun mass spectrometry, when the strains were grown in 2L fermenter tanks with dextrose.

TABLE 5

|  | St2 | St3 |
| --- | --- | --- |
| Relative ALAS titer | 1.00 | 3.3 |

Example 13

Quantification of Leghemoglobin

Cell broth samples were pelleted down (at 4000×g, 4° C., 30 min) and decanted. The pellet samples were then diluted four times with lysis buffer (150 mM NaCl, 50 mM Potassium Phosphate, pH 7.4). 300 uL of each resuspension was dispensed into a 96 well deep plate with 120 uL of beads (Zirconium/silica beads (0.5 mm)) per well for cell lysis. The lysis was done with a mini bead beater for 3 minutes, then the plate was cooled down on ice for 5 minutes, and followed with another 2 minutes of bead beating. The plate was then spun down (at 4000×g, 4° C., 30 min). The supernatant was filtered through a 0.2 um filter plate (at 4000×g, 4° C., 60 min).

The filtered lysate was loaded onto a UHPLC with a size-exclusion column (Acquity BEH SEC column, 200 Å, 1.7 um, 4.6×150 mm). Method parameters: 1) Mobile phase: 5 mM NaCl, 50 mM Potassium Phosphate, (pH 7.4); 2) Flow rate: 0.3 mL/min; 3) Injection volume: 10 uL; 4) Run time: 15 min; 5) Sample tray temperature: 4C. A calibration curve was built with a purified LegH standard using absorbance at 280 nm and 415 nm. The quantification was done using peak area with valley-to-valley peak integration method. The absorbance at 280 nm is proportional to the amount of the polypeptide present and the absorbance at 415 nm is proportional to the amount of heme present. Where a peak is seen at the same elution time at both wavelengths, a heme containing protein is detected.

Example 14 mutALAS Improved Levels of Bovine Myoglobin

In addition to LegH, the production of bovine myoglobin was evaluated. Strain, St7, was generated by integrating myoglobin cDNA of *Bos taurus* (NM_173881.2) in a strain containing recombinant copies of heme enzymes and MxR1 (St7 characterization is described in Example 8) integrated under pAOX1.

Three expression plasmids for expression of GFP (control), wtALAS and mutALAS were constructed as described in Example 3. Three strains, St8, St9 and St10 were generated using a method as described in Example 5 by transforming these three plasmids overexpressing GFP, wtALAS and mutALAS respectively in strain S7, as shown in Table 6. Episomal expression of wtALAS or mutALAS was obtained by growing transformants using a method described in Example 9, except that the growth media was supplemented with 300 ug/ml G418.

TABLE 6

| Plasmid | expressing | Host strain | Host strain expressing | Resulting Strain |
| --- | --- | --- | --- | --- |
| 1 | GFP | St7 | Mb | St8 |
| 2 | wtALAS |  |  | St9 |

TABLE 6-continued

| Plasmid | expressing | Host strain | Host strain expressing | Resulting Strain |
| --- | --- | --- | --- | --- |
| 3 | mutALAS (C12S, C39S) |  |  | St10 |

The cells were pelleted, and shotgun proteomics by LC-MS was performed to quantitate Mb. When normalized to the myoglobin level in Strain St8 (GFP), the average myoglobin levels in St9 and St10 were as shown in Table 7.

TABLE 7

| Strains | Normalized Myoglobin levels |
| --- | --- |
| St8 (GFP) | 1 |
| St9 (wt ALAS) | 1.60 |
| St10 (mutALAS) | 2.58 |

Example 15

Mutations to Other Amino Acids

In addition to cysteine to serine mutations, additional mutations were evaluated. Expression plasmids of mutALAS variants were constructed by gene synthesis and cloning in an autonomous replicating vector (panARS) under a modified pAOX1 followed by the FDH1 transcription terminator sequence. Furthermore, these plasmids were transformed in strain St1, using a method as described in Example 5 and the resulting transformants produced LegH when cultured, using a method described in Example 9, except that the growth media was supplemented with 300 ug/ml G418. The titer of LegH produced by these strains was normalized to the titer of LegH produced by wtALAS, as determined by the method described in Example 13. The results are shown in Table 8.

TABLE 8

| Variant | Normalized LegH titer fold |
| --- | --- |
| C12, C39 (wtALAS) | 1 |
| C12S, C39S (mutALAS) | 1.14 |
| C12A, C39A | 1.22 |
| C12D, C39D | 0.91 |
| C12F, C39F | 1.17 |
| C12H, C39H | 1.12 |

Example 16

Single Cysteine to Serine Mutants in *Pichia pastoris*

In addition to evaluating the double mutant (C12S, C39S) of ALAS in *P. pastoris*, single cysteine to serine mutants were also evaluated. Single mutations were created in wtALAS by site directed mutagenesis as described in Example 2. Expression_plasmids for expression of wtALAS, mutALAS and single ALAS mutants (C12S and C39S) were constructed as described in Example 3 and were transformed in strain St1, using a method as described in Example 5. The resulting transformants produced LegH when cultured, using a method described in Example 9, except that the growth media was supplemented with 300 ug/ml G418. The titer of LegH produced by these strains was normalized to the titer of LegH produced by wtALAS, as determined by the method described in Example 13. The results are shown in Table 9.

TABLE 9

| Variant | Normalized LegH titer fold |
|---|---|
| C12, C39 (wtALAS) | 1 |
| C12S, C39S | 1.27 |
| C12S | 1.03 |
| C39S | 1.01 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
<160> NUMBER OF SEQ ID NOS: 66

<210> SEQ ID NO 1
<211> LENGTH: 161
<212> TYPE: PRT
<213> ORGANISM: Vigna radiata

<400> SEQUENCE: 1

Met Thr Thr Thr Leu Glu Arg Gly Phe Thr Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met Thr Cys Asp Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Arg Thr Gly Val Ala Asn Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asp Ala Ile Lys Tyr Glu Met Lys Pro Pro Ser
145                 150                 155                 160

Ser

<210> SEQ ID NO 2
<211> LENGTH: 133
<212> TYPE: PRT
<213> ORGANISM: Methylacidiphilum infernorum

<400> SEQUENCE: 2

Met Ile Asp Gln Lys Glu Lys Glu Leu Ile Lys Glu Ser Trp Lys Arg
1               5                   10                  15

Ile Glu Pro Asn Lys Asn Glu Ile Gly Leu Leu Phe Tyr Ala Asn Leu
            20                  25                  30

Phe Lys Glu Glu Pro Thr Val Ser Val Leu Phe Gln Asn Pro Ile Ser
        35                  40                  45

Ser Gln Ser Arg Lys Leu Met Gln Val Leu Gly Ile Leu Val Gln Gly
    50                  55                  60

Ile Asp Asn Leu Glu Gly Leu Ile Pro Thr Leu Gln Asp Leu Gly Arg
```

```
            65                  70                  75                  80
Arg His Lys Gln Tyr Gly Val Val Asp Ser His Tyr Pro Leu Val Gly
                    85                  90                  95

Asp Cys Leu Leu Lys Ser Ile Gln Glu Tyr Leu Gly Gln Gly Phe Thr
                    100                 105                 110

Glu Glu Ala Lys Ala Ala Trp Thr Lys Val Tyr Gly Ile Ala Ala Gln
                    115                 120                 125

Val Met Thr Ala Glu
                130

<210> SEQ ID NO 3
<211> LENGTH: 139
<212> TYPE: PRT
<213> ORGANISM: Aquifex aeolicus

<400> SEQUENCE: 3

Met Leu Ser Glu Glu Thr Ile Arg Val Ile Lys Ser Thr Val Pro Leu
1               5                   10                  15

Leu Lys Glu His Gly Thr Glu Ile Thr Ala Arg Met Tyr Glu Leu Leu
                    20                  25                  30

Phe Ser Lys Tyr Pro Lys Thr Lys Glu Leu Phe Ala Gly Ala Ser Glu
                    35                  40                  45

Glu Gln Pro Lys Lys Leu Ala Asn Ala Ile Ile Ala Tyr Ala Thr Tyr
                    50                  55                  60

Ile Asp Arg Leu Glu Glu Leu Asp Asn Ala Ile Ser Thr Ile Ala Arg
65                  70                  75                  80

Ser His Val Arg Arg Asn Val Lys Pro Glu His Tyr Pro Leu Val Lys
                    85                  90                  95

Glu Cys Leu Leu Gln Ala Ile Glu Glu Val Leu Asn Pro Gly Glu Glu
                    100                 105                 110

Val Leu Lys Ala Trp Glu Glu Ala Tyr Asp Phe Leu Ala Lys Thr Leu
                    115                 120                 125

Ile Thr Leu Glu Lys Lys Leu Tyr Ser Gln Pro
                130                 135

<210> SEQ ID NO 4
<211> LENGTH: 145
<212> TYPE: PRT
<213> ORGANISM: Glycine max

<400> SEQUENCE: 4

Met Gly Ala Phe Thr Glu Lys Gln Glu Ala Leu Val Ser Ser Ser Phe
1               5                   10                  15

Glu Ala Phe Lys Ala Asn Ile Pro Gln Tyr Ser Val Val Phe Tyr Thr
                    20                  25                  30

Ser Ile Leu Glu Lys Ala Pro Ala Ala Lys Asp Leu Phe Ser Phe Leu
                    35                  40                  45

Ser Asn Gly Val Asp Pro Ser Asn Pro Lys Leu Thr Gly His Ala Glu
                    50                  55                  60

Lys Leu Phe Gly Leu Val Arg Asp Ser Ala Gly Gln Leu Lys Ala Asn
65                  70                  75                  80

Gly Thr Val Val Ala Asp Ala Ala Leu Gly Ser Ile His Ala Gln Lys
                    85                  90                  95

Ala Ile Thr Asp Pro Gln Phe Val Val Lys Glu Ala Leu Leu Lys
                    100                 105                 110

Thr Ile Lys Glu Ala Val Gly Asp Lys Trp Ser Asp Glu Leu Ser Ser
```

-continued

```
        115                 120                 125

Ala Trp Glu Val Ala Tyr Asp Glu Leu Ala Ala Ala Ile Lys Lys Ala
    130                 135                 140
Phe
145

<210> SEQ ID NO 5
<211> LENGTH: 162
<212> TYPE: PRT
<213> ORGANISM: Hordeum vulgare

<400> SEQUENCE: 5

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met Thr Cys Glu
65                  70                  75                  80

Ala Ala Ala Gln Leu Arg Lys Ala Gly Lys Ile Thr Val Arg Glu Thr
                85                  90                  95

Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Gly Pro Glu Met Arg Asn Ala Trp Gly
    130                 135                 140

Glu Ala Tyr Asp Gln Leu Val Ala Ala Ile Lys Gln Glu Met Lys Pro
145                 150                 155                 160

Ala Glu

<210> SEQ ID NO 6
<211> LENGTH: 1153
<212> TYPE: PRT
<213> ORGANISM: Magnaporthe oryzae

<400> SEQUENCE: 6

Met Asp Gly Ala Val Arg Leu Asp Trp Thr Gly Leu Asp Leu Thr Gly
1               5                   10                  15

His Glu Ile His Asp Gly Val Pro Ile Ala Ser Arg Val Gln Val Met
            20                  25                  30

Val Ser Phe Pro Leu Phe Lys Asp Gln His Ile Ile Met Ser Ser Lys
        35                  40                  45

Glu Ser Pro Ser Arg Lys Ser Ser Thr Ile Gly Gln Ser Thr Arg Asn
    50                  55                  60

Gly Ser Cys Gln Ala Asp Thr Gln Lys Gly Gln Leu Pro Pro Val Gly
65                  70                  75                  80

Glu Lys Pro Lys Pro Val Lys Glu Asn Pro Met Lys Lys Leu Lys Glu
                85                  90                  95

Met Ser Gln Arg Pro Leu Pro Thr Gln His Gly Asp Gly Thr Tyr Pro
            100                 105                 110

Thr Glu Lys Lys Leu Thr Gly Ile Gly Glu Asp Leu Lys His Ile Arg
        115                 120                 125
```

-continued

Gly Tyr Asp Val Lys Thr Leu Leu Ala Met Val Lys Ser Lys Leu Lys
130                 135                 140

Gly Glu Lys Leu Lys Asp Asp Lys Thr Met Leu Met Glu Arg Val Met
145                 150                 155                 160

Gln Leu Val Ala Arg Leu Pro Thr Glu Ser Lys Lys Arg Ala Glu Leu
                165                 170                 175

Thr Asp Ser Leu Ile Asn Glu Leu Trp Glu Ser Leu Asp His Pro Pro
                180                 185                 190

Leu Asn Tyr Leu Gly Pro Glu His Ser Tyr Arg Thr Pro Asp Gly Ser
            195                 200                 205

Tyr Asn His Pro Phe Asn Pro Gln Leu Gly Ala Ala Gly Ser Arg Tyr
        210                 215                 220

Ala Arg Ser Val Ile Pro Thr Val Thr Pro Pro Gly Ala Leu Pro Asp
225                 230                 235                 240

Pro Gly Leu Ile Phe Asp Ser Ile Met Gly Arg Thr Pro Asn Ser Tyr
                245                 250                 255

Arg Lys His Pro Asn Asn Val Ser Ser Ile Leu Trp Tyr Trp Ala Thr
                260                 265                 270

Ile Ile Ile His Asp Ile Phe Trp Thr Asp Pro Arg Asp Ile Asn Thr
            275                 280                 285

Asn Lys Ser Ser Ser Tyr Leu Asp Leu Ala Pro Leu Tyr Gly Asn Ser
        290                 295                 300

Gln Glu Met Gln Asp Ser Ile Arg Thr Phe Lys Asp Gly Arg Met Lys
305                 310                 315                 320

Pro Asp Cys Tyr Ala Asp Lys Arg Leu Ala Gly Met Pro Pro Gly Val
                325                 330                 335

Ser Val Leu Leu Ile Met Phe Asn Arg Phe His Asn His Val Ala Glu
            340                 345                 350

Asn Leu Ala Leu Ile Asn Glu Gly Gly Arg Phe Asn Lys Pro Ser Asp
        355                 360                 365

Leu Leu Glu Gly Glu Ala Arg Glu Ala Ala Trp Lys Lys Tyr Asp Asn
370                 375                 380

Asp Leu Phe Gln Val Ala Arg Leu Val Thr Ser Gly Leu Tyr Ile Asn
385                 390                 395                 400

Ile Thr Leu Val Asp Tyr Val Arg Asn Ile Val Asn Leu Asn Arg Val
                405                 410                 415

Asp Thr Thr Trp Thr Leu Asp Pro Arg Gln Asp Ala Gly Ala His Val
            420                 425                 430

Gly Thr Ala Asp Gly Ala Glu Arg Gly Thr Gly Asn Ala Val Ser Ala
        435                 440                 445

Glu Phe Asn Leu Cys Tyr Arg Trp His Ser Cys Ile Ser Glu Lys Asp
    450                 455                 460

Ser Lys Phe Val Glu Ala Gln Phe Gln Asn Ile Phe Gly Lys Pro Ala
465                 470                 475                 480

Ser Glu Val Arg Pro Asp Glu Met Trp Lys Gly Phe Ala Lys Met Glu
                485                 490                 495

Gln Asn Thr Pro Ala Asp Pro Gly Gln Arg Thr Phe Gly Gly Phe Lys
            500                 505                 510

Arg Gly Pro Asp Gly Lys Phe Asp Asp Asp Leu Val Arg Cys Ile
        515                 520                 525

Ser Glu Ala Val Glu Asp Val Ala Gly Ala Phe Gly Ala Arg Asn Val
530                 535                 540

```
Pro Gln Ala Met Lys Val Val Glu Thr Met Gly Ile Ile Gln Gly Arg
545                 550                 555                 560

Lys Trp Asn Val Ala Gly Leu Asn Glu Phe Arg Lys His Phe His Leu
                565                 570                 575

Lys Pro Tyr Ser Thr Phe Glu Asp Ile Asn Ser Asp Pro Gly Val Ala
            580                 585                 590

Glu Ala Leu Arg Arg Leu Tyr Asp His Pro Asp Asn Val Glu Leu Tyr
        595                 600                 605

Pro Gly Leu Val Ala Glu Asp Lys Gln Pro Met Val Pro Gly Val
610                 615                 620

Gly Ile Ala Pro Thr Tyr Thr Ile Ser Arg Val Val Leu Ser Asp Ala
625                 630                 635                 640

Val Cys Leu Val Arg Gly Asp Arg Phe Tyr Thr Thr Asp Phe Thr Pro
                645                 650                 655

Arg Asn Leu Thr Asn Trp Gly Tyr Lys Glu Val Asp Tyr Asp Leu Ser
            660                 665                 670

Val Asn His Gly Cys Val Phe Tyr Lys Leu Phe Ile Arg Ala Phe Pro
        675                 680                 685

Asn His Phe Lys Gln Asn Ser Val Tyr Ala His Tyr Pro Met Val Val
690                 695                 700

Pro Ser Glu Asn Lys Arg Ile Leu Glu Ala Leu Gly Arg Ala Asp Leu
705                 710                 715                 720

Phe Asp Phe Glu Ala Pro Lys Tyr Ile Pro Pro Arg Val Asn Ile Thr
                725                 730                 735

Ser Tyr Gly Gly Ala Glu Tyr Ile Leu Glu Thr Gln Glu Lys Tyr Lys
            740                 745                 750

Val Thr Trp His Glu Gly Leu Gly Phe Leu Met Gly Glu Gly Gly Leu
        755                 760                 765

Lys Phe Met Leu Ser Gly Asp Asp Pro Leu His Ala Gln Arg Lys
770                 775                 780

Cys Met Ala Ala Gln Leu Tyr Lys Asp Gly Trp Thr Glu Ala Val Lys
785                 790                 795                 800

Ala Phe Tyr Ala Gly Met Met Glu Glu Leu Leu Val Ser Lys Ser Tyr
                805                 810                 815

Phe Leu Gly Asn Asn Lys His Arg His Val Asp Ile Ile Arg Asp Val
            820                 825                 830

Gly Asn Met Val His Val His Phe Ala Ser Gln Val Phe Gly Leu Pro
        835                 840                 845

Leu Lys Thr Ala Lys Asn Pro Thr Gly Val Phe Thr Glu Gln Glu Met
850                 855                 860

Tyr Gly Ile Leu Ala Ala Ile Phe Thr Thr Ile Phe Phe Asp Leu Asp
865                 870                 875                 880

Pro Ser Lys Ser Phe Pro Leu Arg Thr Lys Thr Arg Glu Val Cys Gln
                885                 890                 895

Lys Leu Ala Lys Leu Val Glu Ala Asn Val Lys Leu Ile Asn Lys Ile
            900                 905                 910

Pro Trp Ser Arg Gly Met Phe Val Gly Lys Pro Ala Lys Asp Glu Pro
        915                 920                 925

Leu Ser Ile Tyr Gly Lys Thr Met Ile Lys Gly Leu Lys Ala His Gly
930                 935                 940

Leu Ser Asp Tyr Asp Ile Ala Trp Ser His Val Val Pro Thr Ser Gly
945                 950                 955                 960

Ala Met Val Pro Asn Gln Ala Gln Val Phe Ala Gln Ala Val Asp Tyr
```

```
                    965                 970                 975
Tyr Leu Ser Pro Ala Gly Met His Tyr Ile Pro Glu Ile His Met Val
            980                 985                 990

Ala Leu Gln Pro Ser Thr Pro Glu Thr Asp Ala Leu Leu Leu Gly Tyr
        995                 1000                1005

Ala Met Glu Gly Ile Arg Leu Ala Gly Thr Phe Gly Ser Tyr Arg
        1010                1015                1020

Glu Ala Ala Val Asp Asp Val Val Lys Glu Asp Asn Gly Arg Gln
        1025                1030                1035

Val Pro Val Lys Ala Gly Asp Arg Val Phe Val Ser Phe Val Asp
        1040                1045                1050

Ala Ala Arg Asp Pro Lys His Phe Pro Asp Pro Glu Val Val Asn
        1055                1060                1065

Pro Arg Arg Pro Ala Lys Lys Tyr Ile His Tyr Gly Val Gly Pro
        1070                1075                1080

His Ala Cys Leu Gly Arg Asp Ala Ser Gln Ile Ala Ile Thr Glu
        1085                1090                1095

Met Phe Arg Cys Leu Phe Arg Arg Asn Val Arg Arg Val Pro
        1100                1105                1110

Gly Pro Gln Gly Glu Leu Lys Lys Val Pro Arg Pro Gly Gly Phe
        1115                1120                1125

Tyr Val Tyr Met Arg Glu Asp Trp Gly Gly Leu Phe Pro Phe Pro
        1130                1135                1140

Val Thr Met Arg Val Met Trp Asp Asp Glu
        1145                1150

<210> SEQ ID NO 7
<211> LENGTH: 530
<212> TYPE: PRT
<213> ORGANISM: Fusarium oxysporum

<400> SEQUENCE: 7

Met Lys Gly Ser Ala Thr Leu Ala Phe Ala Leu Val Gln Phe Ser Ala
1               5                   10                  15

Ala Ser Gln Leu Val Trp Pro Ser Lys Trp Asp Glu Val Glu Asp Leu
            20                  25                  30

Leu Tyr Met Gln Gly Gly Phe Asn Lys Arg Gly Phe Ala Asp Ala Leu
        35                  40                  45

Arg Thr Cys Glu Phe Gly Ser Asn Val Pro Gly Thr Gln Asn Thr Ala
    50                  55                  60

Glu Trp Leu Arg Thr Ala Phe His Asp Ala Ile Thr His Asp Ala Lys
65                  70                  75                  80

Ala Gly Thr Gly Gly Leu Asp Ala Ser Ile Tyr Trp Glu Ser Ser Arg
                85                  90                  95

Pro Glu Asn Pro Gly Lys Ala Phe Asn Asn Thr Phe Gly Phe Phe Ser
            100                 105                 110

Gly Phe His Asn Pro Arg Ala Thr Ala Ser Asp Leu Thr Ala Leu Gly
        115                 120                 125

Thr Val Leu Ala Val Gly Ala Cys Asn Gly Pro Arg Ile Pro Phe Arg
    130                 135                 140

Ala Gly Arg Ile Asp Ala Tyr Lys Ala Gly Pro Ala Gly Val Pro Glu
145                 150                 155                 160

Pro Ser Thr Asn Leu Lys Asp Thr Phe Ala Ala Phe Thr Lys Ala Gly
                165                 170                 175
```

```
Phe Thr Lys Glu Glu Met Thr Ala Met Val Ala Cys Gly His Ala Ile
            180                 185                 190

Gly Gly Val His Ser Val Asp Phe Pro Glu Ile Val Gly Ile Lys Ala
        195                 200                 205

Asp Pro Asn Asn Asp Thr Asn Val Pro Phe Gln Lys Asp Val Ser Ser
    210                 215                 220

Phe His Asn Gly Ile Val Thr Glu Tyr Leu Ala Gly Thr Ser Lys Asn
225                 230                 235                 240

Pro Leu Val Ala Ser Lys Asn Ala Thr Phe His Ser Asp Lys Arg Ile
                245                 250                 255

Phe Asp Asn Asp Lys Ala Thr Met Lys Lys Leu Ser Thr Lys Ala Gly
            260                 265                 270

Phe Asn Ser Met Cys Ala Asp Ile Leu Thr Arg Met Ile Asp Thr Val
        275                 280                 285

Pro Lys Ser Val Gln Leu Thr Pro Val Leu Glu Ala Tyr Asp Val Arg
    290                 295                 300

Pro Tyr Ile Thr Glu Leu Ser Leu Asn Asn Lys Asn Lys Ile His Phe
305                 310                 315                 320

Thr Gly Ser Val Arg Val Arg Ile Thr Asn Asn Ile Arg Asp Asn Asn
                325                 330                 335

Asp Leu Ala Ile Asn Leu Ile Tyr Val Gly Arg Asp Gly Lys Lys Val
            340                 345                 350

Thr Val Pro Thr Gln Gln Val Thr Phe Gln Gly Gly Thr Ser Phe Gly
        355                 360                 365

Ala Gly Glu Val Phe Ala Asn Phe Glu Phe Asp Thr Thr Met Asp Ala
    370                 375                 380

Lys Asn Gly Ile Thr Lys Phe Phe Ile Gln Glu Val Lys Pro Ser Thr
385                 390                 395                 400

Lys Ala Thr Val Thr His Asp Asn Gln Lys Thr Gly Gly Tyr Lys Val
                405                 410                 415

Asp Asp Thr Val Leu Tyr Gln Leu Gln Gln Ser Cys Ala Val Leu Glu
            420                 425                 430

Lys Leu Pro Asn Ala Pro Leu Val Val Thr Ala Met Val Arg Asp Ala
        435                 440                 445

Arg Ala Lys Asp Ala Leu Thr Leu Arg Val Ala His Lys Lys Pro Val
    450                 455                 460

Lys Gly Ser Ile Val Pro Arg Phe Gln Thr Ala Ile Thr Asn Phe Lys
465                 470                 475                 480

Ala Thr Gly Lys Lys Ser Ser Gly Tyr Thr Gly Phe Gln Ala Lys Thr
                485                 490                 495

Met Phe Glu Glu Gln Ser Thr Tyr Phe Asp Ile Val Leu Gly Gly Ser
            500                 505                 510

Pro Ala Ser Gly Val Gln Phe Leu Thr Ser Gln Ala Met Pro Ser Gln
        515                 520                 525

Cys Ser
    530

<210> SEQ ID NO 8
<211> LENGTH: 358
<212> TYPE: PRT
<213> ORGANISM: Fusarium graminearum

<400> SEQUENCE: 8

Met Ala Ser Ala Thr Arg Gln Phe Ala Arg Ala Ala Thr Arg Ala Thr
1               5                   10                  15
```

Arg Asn Gly Phe Ala Ile Ala Pro Arg Gln Val Ile Arg Gln Gln Gly
            20                  25                  30

Arg Arg Tyr Tyr Ser Ser Glu Pro Ala Gln Lys Ser Ser Ser Ala Trp
        35                  40                  45

Ile Trp Leu Thr Gly Ala Ala Val Ala Gly Ala Gly Tyr Tyr Phe
 50                  55                  60

Tyr Gly Asn Ser Ala Ser Ser Ala Thr Ala Lys Val Phe Asn Pro Ser
 65                  70                  75                  80

Lys Glu Asp Tyr Gln Lys Val Tyr Asn Glu Ile Ala Ala Arg Leu Glu
                85                  90                  95

Glu Lys Asp Asp Tyr Asp Asp Gly Ser Tyr Gly Pro Val Leu Val Arg
            100                 105                 110

Leu Ala Trp His Ala Ser Gly Thr Tyr Asp Lys Glu Thr Gly Thr Gly
            115                 120                 125

Gly Ser Asn Gly Ala Thr Met Arg Phe Ala Pro Glu Ser Asp His Gly
        130                 135                 140

Ala Asn Ala Gly Leu Ala Ala Arg Asp Phe Leu Gln Pro Val Lys
145                 150                 155                 160

Glu Lys Phe Pro Trp Ile Thr Tyr Ser Asp Leu Trp Ile Leu Ala Gly
                165                 170                 175

Val Cys Ala Ile Gln Glu Met Leu Gly Pro Ala Ile Pro Tyr Arg Pro
            180                 185                 190

Gly Arg Ser Asp Arg Asp Val Ser Gly Cys Thr Pro Asp Gly Arg Leu
        195                 200                 205

Pro Asp Ala Ser Lys Arg Gln Asp His Leu Arg Gly Ile Phe Gly Arg
210                 215                 220

Met Gly Phe Asn Asp Gln Glu Ile Val Ala Leu Ser Gly Ala His Ala
225                 230                 235                 240

Leu Gly Arg Cys His Thr Asp Arg Ser Gly Tyr Ser Gly Pro Trp Thr
                245                 250                 255

Phe Ser Pro Thr Val Leu Thr Asn Asp Tyr Phe Arg Leu Leu Val Glu
            260                 265                 270

Glu Lys Trp Gln Trp Lys Trp Asn Gly Pro Ala Gln Tyr Glu Asp
        275                 280                 285

Lys Ser Thr Lys Ser Leu Met Met Leu Pro Ser Asp Ile Ala Leu Ile
290                 295                 300

Glu Asp Lys Lys Phe Lys Pro Trp Val Glu Lys Tyr Ala Lys Asp Asn
305                 310                 315                 320

Asp Ala Phe Phe Lys Asp Phe Ser Asn Val Val Leu Arg Leu Phe Glu
                325                 330                 335

Leu Gly Val Pro Phe Ala Gln Gly Thr Glu Asn Gln Arg Trp Thr Phe
            340                 345                 350

Lys Pro Thr His Gln Glu
        355

<210> SEQ ID NO 9
<211> LENGTH: 122
<212> TYPE: PRT
<213> ORGANISM: Chlamydomonas eugametos

<400> SEQUENCE: 9

Met Ser Leu Phe Ala Lys Leu Gly Gly Arg Glu Ala Val Glu Ala Ala
1               5                   10                  15

Val Asp Lys Phe Tyr Asn Lys Ile Val Ala Asp Pro Thr Val Ser Thr

```
                    20                  25                  30
Tyr Phe Ser Asn Thr Asp Met Lys Val Gln Arg Ser Lys Gln Phe Ala
            35                  40                  45

Phe Leu Ala Tyr Ala Leu Gly Gly Ala Ser Glu Trp Lys Gly Lys Asp
        50                  55                  60

Met Arg Thr Ala His Lys Asp Leu Val Pro His Leu Ser Asp Val His
65                  70                  75                  80

Phe Gln Ala Val Ala Arg His Leu Ser Asp Thr Leu Thr Glu Leu Gly
                85                  90                  95

Val Pro Pro Glu Asp Ile Thr Asp Ala Met Ala Val Val Ala Ser Thr
            100                 105                 110

Arg Thr Glu Val Leu Asn Met Pro Gln Gln
        115                 120

<210> SEQ ID NO 10
<211> LENGTH: 121
<212> TYPE: PRT
<213> ORGANISM: Tetrahymena pyriformis

<400> SEQUENCE: 10

Met Asn Lys Pro Gln Thr Ile Tyr Glu Lys Leu Gly Gly Glu Asn Ala
1               5                   10                  15

Met Lys Ala Ala Val Pro Leu Phe Tyr Lys Lys Val Leu Ala Asp Glu
            20                  25                  30

Arg Val Lys His Phe Phe Lys Asn Thr Asp Met Asp His Gln Thr Lys
        35                  40                  45

Gln Gln Thr Asp Phe Leu Thr Met Leu Leu Gly Gly Pro Asn His Tyr
    50                  55                  60

Lys Gly Lys Asn Met Thr Glu Ala His Lys Gly Met Asn Leu Gln Asn
65                  70                  75                  80

Leu His Phe Asp Ala Ile Ile Glu Asn Leu Ala Ala Thr Leu Lys Glu
                85                  90                  95

Leu Gly Val Thr Asp Ala Val Ile Asn Glu Ala Ala Lys Val Ile Glu
            100                 105                 110

His Thr Arg Lys Asp Met Leu Gly Lys
        115                 120

<210> SEQ ID NO 11
<211> LENGTH: 117
<212> TYPE: PRT
<213> ORGANISM: Paramecium caudatum

<400> SEQUENCE: 11

Met Ser Leu Phe Glu Gln Leu Gly Gly Gln Ala Ala Val Gln Ala Val
1               5                   10                  15

Thr Ala Gln Phe Tyr Ala Asn Ile Gln Ala Asp Ala Thr Val Ala Thr
            20                  25                  30

Phe Phe Asn Gly Ile Asp Met Pro Asn Gln Thr Asn Lys Thr Ala Ala
        35                  40                  45

Phe Leu Cys Ala Ala Leu Gly Gly Pro Asn Ala Trp Thr Gly Arg Asn
    50                  55                  60

Leu Lys Glu Val His Ala Asn Met Gly Val Ser Asn Ala Gln Phe Thr
65                  70                  75                  80

Thr Val Ile Gly His Leu Arg Ser Ala Leu Thr Gly Ala Gly Val Ala
                85                  90                  95

Ala Ala Leu Val Glu Gln Thr Val Ala Val Ala Glu Thr Val Arg Gly
```

```
                100             105             110
Asp Val Val Thr Val
            115

<210> SEQ ID NO 12
<211> LENGTH: 147
<212> TYPE: PRT
<213> ORGANISM: Aspergillus niger

<400> SEQUENCE: 12

Met Pro Leu Thr Pro Glu Gln Ile Lys Ile Ile Lys Ala Thr Val Pro
1               5                   10                  15

Val Leu Gln Glu Tyr Gly Thr Lys Ile Thr Thr Ala Phe Tyr Met Asn
            20                  25                  30

Met Ser Thr Val His Pro Glu Leu Asn Ala Val Phe Asn Thr Ala Asn
        35                  40                  45

Gln Val Lys Gly His Gln Ala Arg Ala Leu Ala Gly Ala Leu Phe Ala
    50                  55                  60

Tyr Ala Ser His Ile Asp Asp Leu Gly Ala Leu Gly Pro Ala Val Glu
65                  70                  75                  80

Leu Ile Cys Asn Lys His Ala Ser Leu Tyr Ile Gln Ala Asp Glu Tyr
                85                  90                  95

Lys Ile Val Gly Lys Tyr Leu Leu Glu Ala Met Lys Glu Val Leu Gly
            100                 105                 110

Asp Ala Cys Thr Asp Asp Ile Leu Asp Ala Trp Gly Ala Ala Tyr Trp
        115                 120                 125

Ala Leu Ala Asp Ile Met Ile Asn Arg Glu Ala Ala Leu Tyr Lys Gln
    130                 135                 140

Ser Gln Gly
145

<210> SEQ ID NO 13
<211> LENGTH: 165
<212> TYPE: PRT
<213> ORGANISM: Zea mays

<400> SEQUENCE: 13

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Glu Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

Thr Cys Glu Ala Ala Ala Gln Leu Arg Lys Ala Gly Lys Val Thr Val
                85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
        115                 120                 125

Ile Lys Glu Ala Leu Pro Ala Asp Met Trp Ser Leu Glu Met Lys Lys
    130                 135                 140

Ala Trp Ala Glu Ala Tyr Ser Gln Leu Val Ala Ala Ile Lys Arg Glu
```

```
145                 150                 155                 160

Met Lys Pro Asp Ala
                165

<210> SEQ ID NO 14
<211> LENGTH: 169
<212> TYPE: PRT
<213> ORGANISM: Oryza sativa subsp. japonica

<400> SEQUENCE: 14

Met Ala Leu Val Glu Gly Asn Asn Gly Val Ser Gly Ala Val Ser
1               5                   10                  15

Phe Ser Glu Glu Gln Glu Ala Leu Val Leu Lys Ser Trp Ala Ile Met
                20                  25                  30

Lys Lys Asp Ser Ala Asn Ile Gly Leu Arg Phe Phe Leu Lys Ile Phe
                35                  40                  45

Glu Val Ala Pro Ser Ala Ser Gln Met Phe Ser Phe Leu Arg Asn Ser
                50                  55                  60

Asp Val Pro Leu Glu Lys Asn Pro Lys Leu Lys Thr His Ala Met Ser
65                  70                  75                  80

Val Phe Val Met Thr Cys Glu Ala Ala Ala Gln Leu Arg Lys Ala Gly
                85                  90                  95

Lys Val Thr Val Arg Asp Thr Thr Leu Lys Arg Leu Gly Ala Thr His
                100                 105                 110

Phe Lys Tyr Gly Val Gly Asp Ala His Phe Glu Val Thr Arg Phe Ala
                115                 120                 125

Leu Leu Glu Thr Ile Lys Glu Ala Val Pro Val Asp Met Trp Ser Pro
                130                 135                 140

Ala Met Lys Ser Ala Trp Ser Glu Ala Tyr Asn Gln Leu Val Ala Ala
145                 150                 155                 160

Ile Lys Gln Glu Met Lys Pro Ala Glu
                165

<210> SEQ ID NO 15
<211> LENGTH: 160
<212> TYPE: PRT
<213> ORGANISM: Arabidopsis thaliana

<400> SEQUENCE: 15

Met Glu Ser Glu Gly Lys Ile Val Phe Thr Glu Gln Glu Ala Leu
1               5                   10                  15

Val Val Lys Ser Trp Ser Val Met Lys Lys Asn Ser Ala Glu Leu Gly
                20                  25                  30

Leu Lys Leu Phe Ile Lys Ile Phe Glu Ile Ala Pro Thr Thr Lys Lys
                35                  40                  45

Met Phe Ser Phe Leu Arg Asp Ser Pro Ile Pro Ala Glu Gln Asn Pro
                50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
                100                 105                 110

His Phe Glu Val Ala Lys Tyr Ala Leu Leu Glu Thr Ile Lys Glu Ala
                115                 120                 125

Val Pro Glu Met Trp Ser Pro Glu Met Lys Val Ala Trp Gly Gln Ala
```

```
                130                 135                 140
Tyr Asp His Leu Val Ala Ala Ile Lys Ala Glu Met Asn Leu Ser Asn
145                 150                 155                 160

<210> SEQ ID NO 16
<211> LENGTH: 147
<212> TYPE: PRT
<213> ORGANISM: Pisum sativum

<400> SEQUENCE: 16

Met Gly Phe Thr Asp Lys Gln Glu Ala Leu Val Asn Ser Ser Trp Glu
1               5                   10                  15

Ser Phe Lys Gln Asn Leu Ser Gly Asn Ser Ile Leu Phe Tyr Thr Ile
                20                  25                  30

Ile Leu Glu Lys Ala Pro Ala Ala Lys Gly Leu Phe Ser Phe Leu Lys
            35                  40                  45

Asp Thr Ala Gly Val Glu Asp Ser Pro Lys Leu Gln Ala His Ala Glu
        50                  55                  60

Gln Val Phe Gly Leu Val Arg Asp Ser Ala Ala Gln Leu Arg Thr Lys
65                  70                  75                  80

Gly Glu Val Val Leu Gly Asn Ala Thr Leu Gly Ala Ile His Val Gln
                85                  90                  95

Arg Gly Val Thr Asp Pro His Phe Val Val Lys Glu Ala Leu Leu
            100                 105                 110

Gln Thr Ile Lys Lys Ala Ser Gly Asn Asn Trp Ser Glu Glu Leu Asn
        115                 120                 125

Thr Ala Trp Glu Val Ala Tyr Asp Gly Leu Ala Thr Ala Ile Lys Lys
130                 135                 140

Ala Met Thr
145

<210> SEQ ID NO 17
<211> LENGTH: 145
<212> TYPE: PRT
<213> ORGANISM: Vigna unguiculata

<400> SEQUENCE: 17

Met Val Ala Phe Ser Asp Lys Gln Glu Ala Leu Val Asn Gly Ala Tyr
1               5                   10                  15

Glu Ala Phe Lys Ala Asn Ile Pro Lys Tyr Ser Val Val Phe Tyr Thr
                20                  25                  30

Thr Ile Leu Glu Lys Ala Pro Ala Ala Lys Asn Leu Phe Ser Phe Leu
            35                  40                  45

Ala Asn Gly Val Asp Ala Thr Asn Pro Lys Leu Thr Gly His Ala Glu
        50                  55                  60

Lys Leu Phe Gly Leu Val Arg Asp Ser Ala Ala Gln Leu Arg Ala Ser
65                  70                  75                  80

Gly Gly Val Val Ala Asp Ala Ala Leu Gly Ala Val His Ser Gln Lys
                85                  90                  95

Ala Val Asn Asp Ala Gln Phe Val Val Val Lys Glu Ala Leu Val Lys
            100                 105                 110

Thr Leu Lys Glu Ala Val Gly Asp Lys Trp Ser Asp Glu Leu Gly Thr
        115                 120                 125

Ala Val Glu Leu Ala Tyr Asp Glu Leu Ala Ala Ile Lys Lys Ala
130                 135                 140

Tyr
```

<210> SEQ ID NO 18
<211> LENGTH: 154
<212> TYPE: PRT
<213> ORGANISM: Bos taurus

<400> SEQUENCE: 18

Met Gly Leu Ser Asp Gly Glu Trp Gln Leu Val Leu Asn Ala Trp Gly
1               5                   10                  15

Lys Val Glu Ala Asp Val Ala Gly His Gly Gln Glu Val Leu Ile Arg
            20                  25                  30

Leu Phe Thr Gly His Pro Glu Thr Leu Glu Lys Phe Asp Lys Phe Lys
        35                  40                  45

His Leu Lys Thr Glu Ala Glu Met Lys Ala Ser Glu Asp Leu Lys Lys
    50                  55                  60

His Gly Asn Thr Val Leu Thr Ala Leu Gly Gly Ile Leu Lys Lys Lys
65                  70                  75                  80

Gly His His Glu Ala Glu Val Lys His Leu Ala Glu Ser His Ala Asn
                85                  90                  95

Lys His Lys Ile Pro Val Lys Tyr Leu Glu Phe Ile Ser Asp Ala Ile
            100                 105                 110

Ile His Val Leu His Ala Lys His Pro Ser Asp Phe Gly Ala Asp Ala
        115                 120                 125

Gln Ala Ala Met Ser Lys Ala Leu Glu Leu Phe Arg Asn Asp Met Ala
    130                 135                 140

Ala Gln Tyr Lys Val Leu Gly Phe His Gly
145                 150

<210> SEQ ID NO 19
<211> LENGTH: 154
<212> TYPE: PRT
<213> ORGANISM: Sus scrofa

<400> SEQUENCE: 19

Met Gly Leu Ser Asp Gly Glu Trp Gln Leu Val Leu Asn Val Trp Gly
1               5                   10                  15

Lys Val Glu Ala Asp Val Ala Gly His Gly Gln Glu Val Leu Ile Arg
            20                  25                  30

Leu Phe Lys Gly His Pro Glu Thr Leu Glu Lys Phe Asp Lys Phe Lys
        35                  40                  45

His Leu Lys Ser Glu Asp Glu Met Lys Ala Ser Glu Asp Leu Lys Lys
    50                  55                  60

His Gly Asn Thr Val Leu Thr Ala Leu Gly Gly Ile Leu Lys Lys Lys
65                  70                  75                  80

Gly His His Glu Ala Glu Leu Thr Pro Leu Ala Gln Ser His Ala Thr
                85                  90                  95

Lys His Lys Ile Pro Val Lys Tyr Leu Glu Phe Ile Ser Glu Ala Ile
            100                 105                 110

Ile Gln Val Leu Gln Ser Lys His Pro Gly Asp Phe Gly Ala Asp Ala
        115                 120                 125

Gln Gly Ala Met Ser Lys Ala Leu Glu Leu Phe Arg Asn Asp Met Ala
    130                 135                 140

Ala Lys Tyr Lys Glu Leu Gly Phe Gln Gly
145                 150

-continued

```
<210> SEQ ID NO 20
<211> LENGTH: 154
<212> TYPE: PRT
<213> ORGANISM: Equus caballus

<400> SEQUENCE: 20

Met Gly Leu Ser Asp Gly Glu Trp Gln Gln Val Leu Asn Val Trp Gly
1               5                   10                  15

Lys Val Glu Ala Asp Ile Ala Gly His Gly Gln Glu Val Leu Ile Arg
            20                  25                  30

Leu Phe Thr Gly His Pro Glu Thr Leu Glu Lys Phe Asp Lys Phe Lys
        35                  40                  45

His Leu Lys Thr Glu Ala Glu Met Lys Ala Ser Glu Asp Leu Lys Lys
    50                  55                  60

His Gly Thr Val Val Leu Thr Ala Leu Gly Gly Ile Leu Lys Lys Lys
65                  70                  75                  80

Gly His His Glu Ala Glu Leu Lys Pro Leu Ala Gln Ser His Ala Thr
                85                  90                  95

Lys His Lys Ile Pro Ile Lys Tyr Leu Glu Phe Ile Ser Asp Ala Ile
            100                 105                 110

Ile His Val Leu His Ser Lys His Pro Gly Asp Phe Gly Ala Asp Ala
        115                 120                 125

Gln Gly Ala Met Thr Lys Ala Leu Glu Leu Phe Arg Asn Asp Ile Ala
    130                 135                 140

Ala Lys Tyr Lys Glu Leu Gly Phe Gln Gly
145                 150

<210> SEQ ID NO 21
<211> LENGTH: 152
<212> TYPE: PRT
<213> ORGANISM: Nicotiana benthamiana

<400> SEQUENCE: 21

Met Ser Ser Phe Thr Glu Glu Gln Glu Ala Leu Val Val Lys Ser Trp
1               5                   10                  15

Asp Ser Met Lys Lys Asn Ala Gly Glu Trp Gly Leu Lys Leu Phe Leu
            20                  25                  30

Lys Ile Phe Glu Ile Ala Pro Ser Ala Lys Lys Leu Phe Ser Phe Leu
        35                  40                  45

Lys Asp Ser Asn Val Pro Leu Glu Gln Asn Ala Lys Leu Lys Pro His
    50                  55                  60

Ser Lys Ser Val Phe Val Met Thr Cys Glu Ala Ala Val Gln Leu Arg
65                  70                  75                  80

Lys Ala Gly Lys Val Val Arg Asp Ser Thr Leu Lys Lys Leu Gly
                85                  90                  95

Ala Thr His Phe Lys Tyr Gly Val Ala Asp Glu His Phe Glu Val Thr
            100                 105                 110

Lys Phe Ala Leu Leu Glu Thr Ile Lys Glu Ala Val Pro Glu Met Trp
        115                 120                 125

Ser Val Asp Met Lys Asn Ala Trp Gly Glu Ala Phe Asp Gln Leu Val
    130                 135                 140

Asn Ala Ile Lys Thr Glu Met Lys
145                 150

<210> SEQ ID NO 22
<211> LENGTH: 132
<212> TYPE: PRT
```

<213> ORGANISM: Bacillus subtilis

<400> SEQUENCE: 22

```
Met Gly Gln Ser Phe Asn Ala Pro Tyr Glu Ala Ile Gly Glu Glu Leu
1               5                   10                  15

Leu Ser Gln Leu Val Asp Thr Phe Tyr Glu Arg Val Ala Ser His Pro
            20                  25                  30

Leu Leu Lys Pro Ile Phe Pro Ser Asp Leu Thr Glu Thr Ala Arg Lys
        35                  40                  45

Gln Lys Gln Phe Leu Thr Gln Tyr Leu Gly Gly Pro Pro Leu Tyr Thr
    50                  55                  60

Glu Glu His Gly His Pro Met Leu Arg Ala Arg His Leu Pro Phe Pro
65                  70                  75                  80

Ile Thr Asn Glu Arg Ala Asp Ala Trp Leu Ser Cys Met Lys Asp Ala
                85                  90                  95

Met Asp His Val Gly Leu Glu Gly Glu Ile Arg Glu Phe Leu Phe Gly
            100                 105                 110

Arg Leu Glu Leu Thr Ala Arg His Met Val Asn Gln Thr Glu Ala Glu
        115                 120                 125

Asp Arg Ser Ser
    130
```

<210> SEQ ID NO 23
<211> LENGTH: 131
<212> TYPE: PRT
<213> ORGANISM: Corynebacterium glutamicum

<400> SEQUENCE: 23

```
Met Thr Thr Ser Glu Asn Phe Tyr Asp Ser Val Gly Gly Glu Glu Thr
1               5                   10                  15

Phe Ser Leu Ile Val His Arg Phe Tyr Glu Gln Val Pro Asn Asp Asp
            20                  25                  30

Ile Leu Gly Pro Met Tyr Pro Pro Asp Phe Glu Gly Ala Glu Gln
        35                  40                  45

Arg Leu Lys Met Phe Leu Ser Gln Tyr Trp Gly Gly Pro Lys Asp Tyr
    50                  55                  60

Gln Glu Gln Arg Gly His Pro Arg Leu Arg Met Arg His Val Asn Tyr
65                  70                  75                  80

Pro Ile Gly Val Thr Ala Ala Glu Arg Trp Leu Gln Leu Met Ser Asn
                85                  90                  95

Ala Leu Asp Gly Val Asp Leu Thr Ala Glu Gln Arg Glu Ala Ile Trp
            100                 105                 110

Glu His Met Val Arg Ala Ala Asp Met Leu Ile Asn Ser Asn Pro Asp
        115                 120                 125

Pro His Ala
    130
```

<210> SEQ ID NO 24
<211> LENGTH: 124
<212> TYPE: PRT
<213> ORGANISM: Synechocystis sp.

<400> SEQUENCE: 24

```
Met Ser Thr Leu Tyr Glu Lys Leu Gly Gly Thr Thr Ala Val Asp Leu
1               5                   10                  15

Ala Val Asp Lys Phe Tyr Glu Arg Val Leu Gln Asp Asp Arg Ile Lys
            20                  25                  30
```

His Phe Phe Ala Asp Val Asp Met Ala Lys Gln Arg Ala His Gln Lys
                35                  40                  45

Ala Phe Leu Thr Tyr Ala Phe Gly Gly Thr Asp Lys Tyr Asp Gly Arg
 50                  55                  60

Tyr Met Arg Glu Ala His Lys Glu Leu Val Glu Asn His Gly Leu Asn
 65                  70                  75                  80

Gly Glu His Phe Asp Ala Val Ala Glu Asp Leu Leu Ala Thr Leu Lys
                85                  90                  95

Glu Met Gly Val Pro Glu Asp Leu Ile Ala Glu Val Ala Ala Val Ala
                100                 105                 110

Gly Ala Pro Ala His Lys Arg Asp Val Leu Asn Gln
                115                 120

<210> SEQ ID NO 25
<211> LENGTH: 183
<212> TYPE: PRT
<213> ORGANISM: Synechococcus sp.

<400> SEQUENCE: 25

Met Asp Val Ala Leu Leu Glu Lys Ser Phe Glu Gln Ile Ser Pro Arg
1               5                   10                  15

Ala Ile Glu Phe Ser Ala Ser Phe Tyr Gln Asn Leu Phe His His His
                20                  25                  30

Pro Glu Leu Lys Pro Leu Phe Ala Glu Thr Ser Gln Thr Ile Gln Glu
                35                  40                  45

Lys Lys Leu Ile Phe Ser Leu Ala Ala Ile Glu Asn Leu Arg Asn
 50                  55                  60

Pro Asp Ile Leu Gln Pro Ala Leu Lys Ser Leu Gly Ala Arg His Ala
 65                  70                  75                  80

Glu Val Gly Thr Ile Lys Ser His Tyr Pro Leu Val Gly Gln Ala Leu
                85                  90                  95

Ile Glu Thr Phe Ala Glu Tyr Leu Ala Ala Asp Trp Thr Glu Gln Leu
                100                 105                 110

Ala Thr Ala Trp Val Glu Ala Tyr Asp Val Ile Ala Ser Thr Met Ile
                115                 120                 125

Glu Gly Ala Asp Asn Pro Ala Ala Tyr Leu Glu Pro Glu Leu Thr Phe
 130                 135                 140

Tyr Glu Trp Leu Asp Leu Tyr Gly Glu Glu Ser Pro Lys Val Arg Asn
145                 150                 155                 160

Ala Ile Ala Thr Leu Thr His Phe His Tyr Gly Glu Asp Pro Gln Asp
                165                 170                 175

Val Gln Arg Asp Ser Arg Gly
                180

<210> SEQ ID NO 26
<211> LENGTH: 118
<212> TYPE: PRT
<213> ORGANISM: Nostoc commune

<400> SEQUENCE: 26

Met Ser Thr Leu Tyr Asp Asn Ile Gly Gly Gln Pro Ala Ile Glu Gln
1               5                   10                  15

Val Val Asp Glu Leu His Lys Arg Ile Ala Thr Asp Ser Leu Leu Ala
                20                  25                  30

Pro Val Phe Ala Gly Thr Asp Met Val Lys Gln Arg Asn His Leu Val
                35                  40                  45

```
Ala Phe Leu Ala Gln Ile Phe Glu Gly Pro Lys Gln Tyr Gly Gly Arg
        50                  55                  60

Pro Met Asp Lys Thr His Ala Gly Leu Asn Leu Gln Gln Pro His Phe
 65                  70                  75                  80

Asp Ala Ile Ala Lys His Leu Gly Glu Arg Met Ala Val Arg Gly Val
                85                  90                  95

Ser Ala Glu Asn Thr Lys Ala Ala Leu Asp Arg Val Thr Asn Met Lys
            100                 105                 110

Gly Ala Ile Leu Asn Lys
        115

<210> SEQ ID NO 27
<211> LENGTH: 136
<212> TYPE: PRT
<213> ORGANISM: Bacillus megaterium

<400> SEQUENCE: 27

Met Arg Glu Lys Ile His Ser Pro Tyr Glu Leu Leu Gly Gly Glu His
 1               5                  10                  15

Thr Ile Ser Lys Leu Val Asp Ala Phe Tyr Thr Arg Val Gly Gln His
            20                  25                  30

Pro Glu Leu Ala Pro Ile Phe Pro Asp Asn Leu Thr Glu Thr Ala Arg
        35                  40                  45

Lys Gln Lys Gln Phe Leu Thr Gln Tyr Leu Gly Gly Pro Ser Leu Tyr
    50                  55                  60

Thr Glu Glu His Gly His Pro Met Leu Arg Ala Arg His Leu Pro Phe
 65                  70                  75                  80

Glu Ile Thr Pro Ser Arg Ala Lys Ala Trp Leu Thr Cys Met His Glu
                85                  90                  95

Ala Met Asp Glu Ile Asn Leu Glu Gly Pro Glu Arg Asp Glu Leu Tyr
            100                 105                 110

His Arg Leu Ile Leu Thr Ala Gln His Met Ile Asn Ser Pro Glu Gln
        115                 120                 125

Thr Asp Glu Lys Gly Phe Ser His
    130                 135

<210> SEQ ID NO 28
<211> LENGTH: 1683
<212> TYPE: DNA
<213> ORGANISM: Pichia pastoris

<400> SEQUENCE: 28
atggagtttg tcgcccgtca gtccatgaat gcctgtccct tgtcaggtc aacttctacc      60 caccatttga agaagttggc agcaaacagt tctctagctg ctactgctag tcattgtccc    120
gtggttggcc ctgctctcca acagcagaga tactactctc aaccttccaa gccagcccaa    180 gcccaaaccct ccgacattgc tactgggatc aagaaggatg tttctccgat cgtatggac    240 tctaatgaaa ccgcctttga ttacaatgga atgtatgagt ctgatcttgc gaataaacgt    300
aaagataact cgtatcgtta tttcaataac atcaaccgtc tagccaagga gtttcccaag    360
gcacatcgcc agaccgaaga tgacaaggtg accgtctggt gctctaacga ctacttagga    420
atgggtaggc atcctgagat tatcaaaacc atgaaggcta ccatggacaa gtacggttcc    480
ggagcaggag gaactaggaa cattgcaggt cataaccacg ccgctatcaa tttggaaagc    540
gagttggctt gcttgaacaa gaaggaagcg gctctggtgt tttcatcatg tttcatagct    600
```

```
aacgatgcaa tcatctcgtt gttgggacaa aaaatcaaaa atttggtcat tttctctgac    660
cagtcgaatc atgcttccat gatattgggt gtgcgtaact ccaaagcgaa gaagcacatc    720
ttcaagcaca acaatttgaa ggatctggag tcgcagttag ctcagtaccc caagtcgact    780
cctaaactga tcgccttcga gtcagtttac tctatgtgtg atctgtggc tcccattgag     840 aagatttgcg atttggctaa aaggtacggt gccctcacct tcttggatga agttcatgct    900
gttggaatgt atggtcctca tggacagggt gtagctgagc atttggactt tgatctgcat    960
ttacagtctg gaatcgccag tcctagcgtg gtggacaaac gcaccatatt ggatcgtgtc    1020
gacatgatta ctggtacttg cggaaagtca tttggtactg ttggaggtta cgttgctggt    1080
agtgccaacc taattgattg gttaagatcc tatgcgccag gtttcatttt cactaccaca    1140
cttcctcctg ctatcatggc tggtacagcc acttctgttc gtattgttag ggccgacatt    1200
gaggcccgta tcaagcaaca gcttaatact cgctacgtca aagactcatt tgaaaacctt    1260
ggtattccag tcattccaaa cccaagtcac attgttcctg ttctagttgg aaatgctgca    1320
gatgccaaga aggcatccga tatgttaatg aacaaacacc gtatttatgt tcaagctatt    1380
aactacccta ctgtgcctgt cggtgaagaa cgactaagga ttactcctac tccaggtcat    1440
ggaaaggaga tttgtgacca gctgatcagc gctgtcgacg atgtttttac tgagcttaat    1500
ttaccaagaa tcaacaaatg cagtcccaa ggtggtcatt gcggtgttgg tgatgctaat     1560
tacgtaccag aacccaatct gtggactcag gaccagctca gcttgacaaa ccaagacttg    1620
cactccaatg tgcacaaccc agtgattgag cagatcgaaa cctcatcagg agtcagattg    1680
tag                                                                 1683
```

<210> SEQ ID NO 29
<211> LENGTH: 560
<212> TYPE: PRT
<213> ORGANISM: Pichia pastoris

<400> SEQUENCE: 29

```
Met Glu Phe Val Ala Arg Gln Ser Met Asn Ala Cys Pro Phe Val Arg
1               5                   10                  15

Ser Thr Ser Thr His His Leu Lys Lys Leu Ala Ala Asn Ser Ser Leu
            20                  25                  30

Ala Ala Thr Ala Ser His Cys Pro Val Val Gly Pro Ala Leu Gln Gln
        35                  40                  45

Gln Arg Tyr Tyr Ser Gln Pro Ser Lys Pro Ala Gln Ala Gln Thr Ser
    50                  55                  60

Asp Ile Ala Thr Gly Ile Lys Lys Asp Val Ser Pro Ile Arg Met Asp
65                  70                  75                  80

Ser Asn Glu Thr Ala Phe Asp Tyr Asn Gly Met Tyr Glu Ser Asp Leu
                85                  90                  95

Ala Asn Lys Arg Lys Asp Asn Ser Tyr Arg Tyr Phe Asn Asn Ile Asn
            100                 105                 110

Arg Leu Ala Lys Glu Phe Pro Lys Ala His Arg Gln Thr Glu Asp Asp
        115                 120                 125

Lys Val Thr Val Trp Cys Ser Asn Asp Tyr Leu Gly Met Gly Arg His
    130                 135                 140

Pro Glu Ile Ile Lys Thr Met Lys Ala Thr Met Asp Lys Tyr Gly Ser
145                 150                 155                 160

Gly Ala Gly Gly Thr Arg Asn Ile Ala Gly His Asn His Ala Ala Ile
                165                 170                 175
```

Asn Leu Glu Ser Glu Leu Ala Cys Leu Asn Lys Lys Glu Ala Ala Leu
            180                 185                 190

Val Phe Ser Ser Cys Phe Ile Ala Asn Asp Ala Ile Ile Ser Leu Leu
        195                 200                 205

Gly Gln Lys Ile Lys Asn Leu Val Ile Phe Ser Asp Gln Ser Asn His
    210                 215                 220

Ala Ser Met Ile Leu Gly Val Arg Asn Ser Lys Ala Lys Lys His Ile
225                 230                 235                 240

Phe Lys His Asn Asn Leu Lys Asp Leu Glu Ser Gln Leu Ala Gln Tyr
                245                 250                 255

Pro Lys Ser Thr Pro Lys Leu Ile Ala Phe Glu Ser Val Tyr Ser Met
            260                 265                 270

Cys Gly Ser Val Ala Pro Ile Glu Lys Ile Cys Asp Leu Ala Lys Arg
        275                 280                 285

Tyr Gly Ala Leu Thr Phe Leu Asp Glu Val His Ala Val Gly Met Tyr
    290                 295                 300

Gly Pro His Gly Gln Gly Val Ala Glu His Leu Asp Phe Asp Leu His
305                 310                 315                 320

Leu Gln Ser Gly Ile Ala Ser Pro Ser Val Val Asp Lys Arg Thr Ile
                325                 330                 335

Leu Asp Arg Val Asp Met Ile Thr Gly Thr Cys Gly Lys Ser Phe Gly
            340                 345                 350

Thr Val Gly Gly Tyr Val Ala Gly Ser Ala Asn Leu Ile Asp Trp Leu
        355                 360                 365

Arg Ser Tyr Ala Pro Gly Phe Ile Phe Thr Thr Thr Leu Pro Pro Ala
    370                 375                 380

Ile Met Ala Gly Thr Ala Thr Ser Val Arg Ile Val Arg Ala Asp Ile
385                 390                 395                 400

Glu Ala Arg Ile Lys Gln Gln Leu Asn Thr Arg Tyr Val Lys Asp Ser
                405                 410                 415

Phe Glu Asn Leu Gly Ile Pro Val Ile Pro Asn Pro Ser His Ile Val
            420                 425                 430

Pro Val Leu Val Gly Asn Ala Ala Asp Ala Lys Lys Ala Ser Asp Met
        435                 440                 445

Leu Met Asn Lys His Arg Ile Tyr Val Gln Ala Ile Asn Tyr Pro Thr
    450                 455                 460

Val Pro Val Gly Glu Glu Arg Leu Arg Ile Thr Pro Thr Pro Gly His
465                 470                 475                 480

Gly Lys Glu Ile Cys Asp Gln Leu Ile Ser Ala Val Asp Asp Val Phe
                485                 490                 495

Thr Glu Leu Asn Leu Pro Arg Ile Asn Lys Trp Gln Ser Gln Gly Gly
            500                 505                 510

His Cys Gly Val Gly Asp Ala Asn Tyr Val Pro Glu Pro Asn Leu Trp
        515                 520                 525

Thr Gln Asp Gln Leu Ser Leu Thr Asn Gln Asp Leu His Ser Asn Val
    530                 535                 540

His Asn Pro Val Ile Glu Gln Ile Glu Thr Ser Ser Gly Val Arg Leu
545                 550                 555                 560

<210> SEQ ID NO 30
<211> LENGTH: 1683
<212> TYPE: DNA
<213> ORGANISM: Artificial
<220> FEATURE:
<223> OTHER INFORMATION: Mutated sequence

<400> SEQUENCE: 30

```
atggagtttg tcgcccgtca gtccatgaat gcctctccct tgtcaggtc  aacttctacc    60
caccatttga agaagttggc agcaaacagt tctctagctg ctactgctag tcattctccc   120
gtggttggcc ctgctctcca acagcagaga tactactctc aaccttccaa gccagcccaa   180
gcccaaacct ccgacattgc tactgggatc aagaaggatg tttctccgat ccgtatggac   240
tctaatgaaa ccgcctttga ttacaatgga atgtatgagt ctgatcttgc gaataaacgt   300
aaagataact cgtatcgtta tttcaataac atcaaccgtc tagccaagga gtttcccaag   360
gcacatcgcc agaccgaaga tgacaaggtg accgtctggt gctctaacga ctacttagga   420
atgggtaggc atcctgagat tatcaaaacc atgaaggcta ccatggacaa gtacggttcc   480
ggagcaggag gaactaggaa cattgcaggt cataaccacg ccgctatcaa tttggaaagc   540
gagttggctt gcttgaacaa gaaggaagcg gctctggtgt tttcatcatg tttcatagct   600
aacgatgcaa tcatctcgtt gttgggacaa aaaatcaaaa atttggtcat tttctctgac   660
cagtcgaatc atgcttccat gatattgggt gtgcgtaact ccaaagcgaa gaagcacatc   720
ttcaagcaca acaatttgaa ggatctggag tcgcagttag ctcagtaccc caagtcgact   780
cctaaactga tcgccttcga gtcagtttac tctatgtgtg gatctgtggc tcccattgag   840
aagatttgcg atttggctaa aaggtacggt gccctcacct tcttggatga agttcatgct   900
gttggaatgt atggtcctca tggacagggt gtagctgagc atttggactt tgatctgcat   960
ttacagtctg gaatcgccag tcctagcgtg gtggacaaac gcaccatatt ggatcgtgtc  1020
gacatgatta ctggtacttg cggaaagtca tttggtactg ttggaggtta cgttgctggt  1080
agtgccaacc taattgattg gttaagatcc tatgcgccag gtttcatttt cactaccaca  1140
cttcctcctg ctatcatggc tggtacagcc acttctgttc gtattgttag ggccgacatt  1200
gaggcccgta tcaagcaaca gcttaatact cgctacgtca agactcattt gaaaaacctt  1260
ggtattccag tcattccaaa cccaagtcac attgttcctg ttctagttgg aaatgctgca  1320
gatgccaaga aggcatccga tatgttaatg aacaaacacc gtatttatgt tcaagctatt  1380
aactacccta ctgtgcctgt cggtgaagaa cgactaagga ttactcctac tccaggtcat  1440
ggaaaggaga tttgtgacca gctgatcagc gctgtcgacg atgttttttac tgagcttaat  1500
ttaccaagaa tcaacaaatg gcagtcccaa ggtggtcatt gcggtgttgg tgatgctaat  1560
tacgtaccag aacccaatct gtggactcag gaccagctca gcttgacaaa ccaagacttg  1620
cactccaatg tgcacaaccc agtgattgag cagatcgaaa cctcatcagg agtcagattg  1680
tag                                                                 1683
```

<210> SEQ ID NO 31
<211> LENGTH: 560
<212> TYPE: PRT
<213> ORGANISM: Artificial
<220> FEATURE:
<223> OTHER INFORMATION: Mutated sequence

<400> SEQUENCE: 31

```
Met Glu Phe Val Ala Arg Gln Ser Met Asn Ala Ser Pro Phe Val Arg
1               5                   10                  15

Ser Thr Ser Thr His His Leu Lys Lys Leu Ala Ala Asn Ser Ser Leu
            20                  25                  30

Ala Ala Thr Ala Ser His Ser Pro Val Val Gly Pro Ala Leu Gln Gln
        35                  40                  45
```

```
Gln Arg Tyr Tyr Ser Gln Pro Ser Lys Pro Ala Gln Ala Gln Thr Ser
     50                  55                  60

Asp Ile Ala Thr Gly Ile Lys Lys Asp Val Ser Pro Ile Arg Met Asp
 65                  70                  75                  80

Ser Asn Glu Thr Ala Phe Asp Tyr Asn Gly Met Tyr Glu Ser Asp Leu
                 85                  90                  95

Ala Asn Lys Arg Lys Asp Asn Ser Tyr Arg Tyr Phe Asn Asn Ile Asn
                100                 105                 110

Arg Leu Ala Lys Glu Phe Pro Lys Ala His Arg Gln Thr Glu Asp Asp
            115                 120                 125

Lys Val Thr Val Trp Cys Ser Asn Asp Tyr Leu Gly Met Gly Arg His
        130                 135                 140

Pro Glu Ile Ile Lys Thr Met Lys Ala Thr Met Asp Lys Tyr Gly Ser
145                 150                 155                 160

Gly Ala Gly Gly Thr Arg Asn Ile Ala Gly His Asn His Ala Ala Ile
                165                 170                 175

Asn Leu Glu Ser Glu Leu Ala Cys Leu Asn Lys Lys Glu Ala Ala Leu
            180                 185                 190

Val Phe Ser Ser Cys Phe Ile Ala Asn Asp Ala Ile Ile Ser Leu Leu
        195                 200                 205

Gly Gln Lys Ile Lys Asn Leu Val Ile Phe Ser Asp Gln Ser Asn His
210                 215                 220

Ala Ser Met Ile Leu Gly Val Arg Asn Ser Lys Ala Lys Lys His Ile
225                 230                 235                 240

Phe Lys His Asn Asn Leu Lys Asp Leu Glu Ser Gln Leu Ala Gln Tyr
                245                 250                 255

Pro Lys Ser Thr Pro Lys Leu Ile Ala Phe Glu Ser Val Tyr Ser Met
            260                 265                 270

Cys Gly Ser Val Ala Pro Ile Glu Lys Ile Cys Asp Leu Ala Lys Arg
        275                 280                 285

Tyr Gly Ala Leu Thr Phe Leu Asp Glu Val His Ala Val Gly Met Tyr
    290                 295                 300

Gly Pro His Gly Gln Gly Val Ala Glu His Leu Asp Phe Asp Leu His
305                 310                 315                 320

Leu Gln Ser Gly Ile Ala Ser Pro Ser Val Val Asp Lys Arg Thr Ile
                325                 330                 335

Leu Asp Arg Val Asp Met Ile Thr Gly Thr Cys Gly Lys Ser Phe Gly
            340                 345                 350

Thr Val Gly Gly Tyr Val Ala Gly Ser Ala Asn Leu Ile Asp Trp Leu
        355                 360                 365

Arg Ser Tyr Ala Pro Gly Phe Ile Phe Thr Thr Thr Leu Pro Pro Ala
370                 375                 380

Ile Met Ala Gly Thr Ala Thr Ser Val Arg Ile Val Arg Ala Asp Ile
385                 390                 395                 400

Glu Ala Arg Ile Lys Gln Gln Leu Asn Thr Arg Tyr Val Lys Asp Ser
                405                 410                 415

Phe Glu Asn Leu Gly Ile Pro Val Ile Pro Asn Pro Ser His Ile Val
            420                 425                 430

Pro Val Leu Val Gly Asn Ala Ala Asp Ala Lys Lys Ala Ser Asp Met
        435                 440                 445

Leu Met Asn Lys His Arg Ile Tyr Val Gln Ala Ile Asn Tyr Pro Thr
450                 455                 460
```

```
Val Pro Val Gly Glu Glu Arg Leu Arg Ile Thr Pro Thr Pro Gly His
465                 470                 475                 480

Gly Lys Glu Ile Cys Asp Gln Leu Ile Ser Ala Val Asp Asp Val Phe
            485                 490                 495

Thr Glu Leu Asn Leu Pro Arg Ile Asn Lys Trp Gln Ser Gln Gly Gly
        500                 505                 510

His Cys Gly Val Gly Asp Ala Asn Tyr Val Pro Glu Pro Asn Leu Trp
        515                 520                 525

Thr Gln Asp Gln Leu Ser Leu Thr Asn Gln Asp Leu His Ser Asn Val
        530                 535                 540

His Asn Pro Val Ile Glu Gln Ile Glu Thr Ser Ser Gly Val Arg Leu
545                 550                 555                 560
```

<210> SEQ ID NO 32
<211> LENGTH: 5
<212> TYPE: PRT
<213> ORGANISM: Artificial
<220> FEATURE:
<223> OTHER INFORMATION: Exemplary HRM sequence
<220> FEATURE:
<221> NAME/KEY: misc_feature
<222> LOCATION: (1)..(1)
<223> OTHER INFORMATION: Xaa can be R/L/N/A/C/S/H/I/G/Q
<220> FEATURE:
<221> NAME/KEY: misc_feature
<222> LOCATION: (4)..(4)
<223> OTHER INFORMATION: Xaa can be L/V/I/F/C
<220> FEATURE:
<221> NAME/KEY: misc_feature
<222> LOCATION: (5)..(5)
<223> OTHER INFORMATION: Xaa can be L/M/P/V

<400> SEQUENCE: 32

```
Xaa Cys Pro Xaa Xaa
1               5
```

<210> SEQ ID NO 33
<211> LENGTH: 5
<212> TYPE: PRT
<213> ORGANISM: Artificial
<220> FEATURE:
<223> OTHER INFORMATION: Exemplary HRM sequence.

<400> SEQUENCE: 33

```
Ala Cys Pro Phe Val
1               5
```

<210> SEQ ID NO 34
<211> LENGTH: 5
<212> TYPE: PRT
<213> ORGANISM: Artificial
<220> FEATURE:
<223> OTHER INFORMATION: Exemplary HRM sequence.

<400> SEQUENCE: 34

```
His Cys Pro Val Val
1               5
```

<210> SEQ ID NO 35
<211> LENGTH: 5
<212> TYPE: PRT
<213> ORGANISM: Artificial
<220> FEATURE:
<223> OTHER INFORMATION: Exemplary HRM sequence.

<400> SEQUENCE: 35

Ile Cys Pro Phe Met
1               5

<210> SEQ ID NO 36
<211> LENGTH: 5
<212> TYPE: PRT
<213> ORGANISM: Artificial
<220> FEATURE:
<223> OTHER INFORMATION: Exemplary HRM sequence.

<400> SEQUENCE: 36

Gly Cys Pro Val Val
1               5

<210> SEQ ID NO 37
<211> LENGTH: 41
<212> TYPE: DNA
<213> ORGANISM: Artificial
<220> FEATURE:
<223> OTHER INFORMATION: Synthetic primer

<400> SEQUENCE: 37
cgtcagtcca tgaatgcctc tccctttgtc aggtcaactt c          41

<210> SEQ ID NO 38
<211> LENGTH: 41
<212> TYPE: DNA
<213> ORGANISM: Artificial
<220> FEATURE:
<223> OTHER INFORMATION: Synthetic primer

<400> SEQUENCE: 38
gaagttgacc tgacaaaggg agaggcattc atggactgac g          41

<210> SEQ ID NO 39
<211> LENGTH: 37
<212> TYPE: DNA
<213> ORGANISM: Artificial
<220> FEATURE:
<223> OTHER INFORMATION: Synthetic primer

<400> SEQUENCE: 39
gctgctactg ctagtcattc tcccgtggtt ggccctg              37

<210> SEQ ID NO 40
<211> LENGTH: 37
<212> TYPE: DNA
<213> ORGANISM: Artificial
<220> FEATURE:
<223> OTHER INFORMATION: Synthetic primer

<400> SEQUENCE: 40
cagggccaac cacgggagaa tgactagcag tagcagc              37

<210> SEQ ID NO 41
<211> LENGTH: 27
<212> TYPE: DNA
<213> ORGANISM: Artificial
<220> FEATURE:
<223> OTHER INFORMATION: Synthetic primer

<400> SEQUENCE: 41
aaacgctgtc ttggaaccta atatgac                        27

<210> SEQ ID NO 42
<211> LENGTH: 38

```
<212> TYPE: DNA
<213> ORGANISM: Artificial
<220> FEATURE:
<223> OTHER INFORMATION: Synthetic primer

<400> SEQUENCE: 42
gacgggcgac aaactccatc gtttcgaata attagttg                                 38

<210> SEQ ID NO 43
<211> LENGTH: 40
<212> TYPE: DNA
<213> ORGANISM: Artificial
<220> FEATURE:
<223> OTHER INFORMATION: Synthetic primer

<400> SEQUENCE: 43
caactaatta ttcgaaacga tggagtttgt cgcccgtcag                               40

<210> SEQ ID NO 44
<211> LENGTH: 45
<212> TYPE: DNA
<213> ORGANISM: Artificial
<220> FEATURE:
<223> OTHER INFORMATION: Synthetic primer

<400> SEQUENCE: 44
aattaaatac atttcaacta caatctgact cctgatgagg tttcg                         45

<210> SEQ ID NO 45
<211> LENGTH: 42
<212> TYPE: DNA
<213> ORGANISM: Artificial
<220> FEATURE:
<223> OTHER INFORMATION: Synthetic primer

<400> SEQUENCE: 45
cctcatcagg agtcagattg tagttgaaat gtatttaatt tg                            42

<210> SEQ ID NO 46
<211> LENGTH: 24
<212> TYPE: DNA
<213> ORGANISM: Artificial
<220> FEATURE:
<223> OTHER INFORMATION: Synthetic primer

<400> SEQUENCE: 46
aaactgtcag ttttgggcca tttg                                                24

<210> SEQ ID NO 47
<211> LENGTH: 21
<212> TYPE: DNA
<213> ORGANISM: Artificial
<220> FEATURE:
<223> OTHER INFORMATION: Synthetic primer

<400> SEQUENCE: 47
gctctccaac agcagagata c                                                   21

<210> SEQ ID NO 48
<211> LENGTH: 21
<212> TYPE: DNA
<213> ORGANISM: Artificial
<220> FEATURE:
<223> OTHER INFORMATION: Synthetic primer

<400> SEQUENCE: 48
```
gtccatacgg atcggagaaa c    21

<210> SEQ ID NO 49
<211> LENGTH: 19
<212> TYPE: DNA
<213> ORGANISM: Artificial
<220> FEATURE:
<223> OTHER INFORMATION: Synthetic primer

<400> SEQUENCE: 49
agcaacatcc ctgattccg    19

<210> SEQ ID NO 50
<211> LENGTH: 20
<212> TYPE: DNA
<213> ORGANISM: Artificial
<220> FEATURE:
<223> OTHER INFORMATION: Synthetic primer

<400> SEQUENCE: 50
atgcgtacct tcaatcctgg    20

<210> SEQ ID NO 51
<211> LENGTH: 24
<212> TYPE: DNA
<213> ORGANISM: Artificial
<220> FEATURE:
<223> OTHER INFORMATION: PCR probe. A1 labeled with 6FAM. A9 labeled
      with Zen. A21 labeled with 3IABkFQ

<400> SEQUENCE: 51
aagcccaaac ctccgacatt gcta    24

<210> SEQ ID NO 52
<211> LENGTH: 28
<212> TYPE: DNA
<213> ORGANISM: Artificial
<220> FEATURE:
<223> OTHER INFORMATION: PCR probe. T1 labeled with HEX. A9 labeled with
      Zen. C28 labeled with 3IABkFQ

<400> SEQUENCE: 52
tcgccgtaag ttcttggttt agacgttc    28

<210> SEQ ID NO 53
<211> LENGTH: 23
<212> TYPE: DNA
<213> ORGANISM: Artificial
<220> FEATURE:
<223> OTHER INFORMATION: Synthetic primer

<400> SEQUENCE: 53
tagcgcagtc tctctatcgc ttc    23

<210> SEQ ID NO 54
<211> LENGTH: 20
<212> TYPE: DNA
<213> ORGANISM: Artificial
<220> FEATURE:
<223> OTHER INFORMATION: Synthetic primer

<400> SEQUENCE: 54
cactgggttg tgcacattgg    20

<210> SEQ ID NO 55
<211> LENGTH: 20

```
<212> TYPE: DNA
<213> ORGANISM: Artificial
<220> FEATURE:
<223> OTHER INFORMATION: Synthetic primer

<400> SEQUENCE: 55
acaatattct tctctgccgc                                               20

<210> SEQ ID NO 56
<211> LENGTH: 20
<212> TYPE: DNA
<213> ORGANISM: Artificial
<220> FEATURE:
<223> OTHER INFORMATION: Synthetic primer

<400> SEQUENCE: 56
ttgatctcgt caagaatgcg                                               20

<210> SEQ ID NO 57
<211> LENGTH: 23
<212> TYPE: DNA
<213> ORGANISM: Artificial
<220> FEATURE:
<223> OTHER INFORMATION: Synthetic primer

<400> SEQUENCE: 57
taggtgccac aactttggt ttc                                            23

<210> SEQ ID NO 58
<211> LENGTH: 24
<212> TYPE: DNA
<213> ORGANISM: Artificial
<220> FEATURE:
<223> OTHER INFORMATION: Synthetic primer

<400> SEQUENCE: 58
gatccaatgc gatgacattc ttgt                                          24

<210> SEQ ID NO 59
<211> LENGTH: 24
<212> TYPE: DNA
<213> ORGANISM: Artificial
<220> FEATURE:
<223> OTHER INFORMATION: Synthetic primer

<400> SEQUENCE: 59
acctgcaata actcctcttc tctg                                          24

<210> SEQ ID NO 60
<211> LENGTH: 20
<212> TYPE: DNA
<213> ORGANISM: Artificial
<220> FEATURE:
<223> OTHER INFORMATION: Synthetic primer

<400> SEQUENCE: 60
ccactgaggg tagccgaatc                                               20

<210> SEQ ID NO 61
<211> LENGTH: 22
<212> TYPE: DNA
<213> ORGANISM: Artificial
<220> FEATURE:
<223> OTHER INFORMATION: Synthetic primer

<400> SEQUENCE: 61
```

```
gggctctgaa aaactctttt gg                                           22

<210> SEQ ID NO 62
<211> LENGTH: 27
<212> TYPE: DNA
<213> ORGANISM: Artificial
<220> FEATURE:
<223> OTHER INFORMATION: Synthetic primer

<400> SEQUENCE: 62
gcatgtctca ataacagatc tcgacgg                                      27

<210> SEQ ID NO 63
<211> LENGTH: 27
<212> TYPE: DNA
<213> ORGANISM: Artificial
<220> FEATURE:
<223> OTHER INFORMATION: Synthetic primer

<400> SEQUENCE: 63
aagcctcttg tttttctgta aatgcac                                      27

<210> SEQ ID NO 64
<211> LENGTH: 22
<212> TYPE: DNA
<213> ORGANISM: Artificial
<220> FEATURE:
<223> OTHER INFORMATION: Synthetic primer

<400> SEQUENCE: 64
tgatggcgtc cgagatgaac tc                                           22

<210> SEQ ID NO 65
<211> LENGTH: 21
<212> TYPE: DNA
<213> ORGANISM: Artificial
<220> FEATURE:
<223> OTHER INFORMATION: synthetic primers

<400> SEQUENCE: 65
atggagtttg tcgcccgtca g                                            21

<210> SEQ ID NO 66
<211> LENGTH: 27
<212> TYPE: DNA
<213> ORGANISM: Artificial
<220> FEATURE:
<223> OTHER INFORMATION: synthetic primers

<400> SEQUENCE: 66
ctacaatctg actcctgatg aggtttc                                      27
```

What is claimed is:

1. A cell comprising:
   a first exogenous nucleic acid construct comprising a nucleotide sequence encoding an aminolevulinate synthase (ALAS) protein operably linked to a first promoter element, wherein the ALAS protein comprises an amino acid sequence having at least 80% sequence identity to the amino acid sequence of SEQ ID NO: 29, wherein the ALAS protein comprises at least a first heme responsive motif (HRM), wherein the first HRM comprises the amino acid sequence of SEQ ID NO:32 except for a mutation relative to the amino acid sequence of SEQ ID NO:32, wherein the mutation relative to the amino acid sequence of SEQ ID NO:32 in the first HRM corresponds to a mutation in residue 12 of SEQ ID NO: 29, and wherein the ALAS protein catalyzes the transformation of glycine and succinyl-CoA to aminolevulinic acid; and
   a second exogenous nucleic acid construct comprising a nucleotide sequence encoding a heme-binding protein, wherein the second exogenous nucleic acid construct comprising a nucleotide sequence encoding the heme-binding protein is operably linked to the first promoter element or is operably linked to a second promoter element.

2. The cell of claim 1, wherein the cell is a bacterial cell, a fungal cell, an algal cell, a plant cell, an insect cell, or a mammalian cell.

3. The cell of claim 1, wherein the mutation relative to the amino acid sequence of SEQ ID NO:32 in the first HRM is a mutation from a cysteine to a different amino acid.

4. The cell of claim 3, wherein the ALAS protein comprises a second HRM, wherein the second HRM comprises the amino acid sequence of SEQ ID NO:32 except for a mutation relative to the amino acid sequence of SEQ ID NO:32, and wherein the mutation relative to the amino acid sequence of SEQ ID NO:32 in the second HRM corresponds to a mutation in residue 39 of SEQ ID NO: 29.

5. The cell of claim 4, wherein the mutation relative to the amino acid sequence of SEQ ID NO:32 in the second HRM is a mutation from a cysteine to a different amino acid.

6. The cell of claim 5, wherein the different amino acid is the same for the mutation relative to the amino acid sequence of SEQ ID NO:32 in the first HRM and the mutation relative to the amino acid sequence of SEQ ID NO:32 in the second HRM.

7. The cell of claim 3, wherein the different amino acid is serine, alanine, phenylalanine, or histidine.

8. The cell of claim 1, wherein the ALAS protein comprises an amino acid sequence having at least 90% sequence identity to the amino acid sequence of SEQ ID NO: 29.

9. The cell of claim 1, wherein the heme-binding protein is selected from the group consisting of a globin, a cytochrome, a cytochrome c oxidase, a ligninase, a catalase, and a peroxidase.

10. The cell of claim 1, wherein the first HRM has the amino acid sequence of any one of SEQ ID NOs: 33-36 except for a mutation relative to the amino acid sequence of any one of SEQ ID NOs:33-36.

11. The cell of claim 4, wherein the second HRM has the amino acid sequence of any one of SEQ ID NOs: 33-36 except for a mutation relative to the amino acid sequence of any one of SEQ ID NOs:33-36.

12. The cell of claim 1, wherein the ALAS protein comprises an amino acid sequence having at least 95% sequence identity to the amino acid sequence of SEQ ID NO: 29.

13. The cell of claim 1, wherein the cell is a bacterial cell.

14. The cell of claim 1, wherein the cell is a fungal cell.

15. The cell of claim 1, wherein the cell is an algal cell.

16. The cell of claim 1, wherein the cell is a mammalian cell.

17. The cell of claim 5, wherein the different amino acid in the second HRM is serine, alanine, phenylalanine, or histidine.

18. The cell of claim 5, wherein the different amino acid is different for the mutation relative to the amino acid sequence of SEQ ID NO:32 in the first HRM and the mutation relative to the amino acid sequence of SEQ ID NO:32 in the second HRM.

19. The cell of claim 6, wherein the different amino acid is serine, alanine, phenylalanine, or histidine.

\* \* \* \* \*